(12) United States Patent
Arnal et al.

(10) Patent No.: US 6,192,900 B1
(45) Date of Patent: Feb. 27, 2001

(54) METHOD OF CLEANING A DIALYZER HEADER

(75) Inventors: Kevin R. Arnal, Chanhassen; Robert G. Andrus, Plymouth; David A. Luhring, Savage; Jeffrey C. Toy, Plymouth, all of MN (US)

(73) Assignee: Minntech Corporation, Minneapolis, MN (US)

( * ) Notice: Subject to any disclaimer, the term of this patent is extended or adjusted under 35 U.S.C. 154(b) by 0 days.

(21) Appl. No.: 09/459,520

(22) Filed: Dec. 13, 1999

Related U.S. Application Data

(62) Division of application No. 09/369,826, filed on Aug. 6, 1999, now Pat. No. 6,050,278.
(60) Provisional application No. 60/128,550, filed on Apr. 9, 1999, and provisional application No. 60/101,624, filed on Sep. 24, 1998.

(51) Int. Cl.⁷ .............................. B08B 3/02; B01D 61/26
(52) U.S. Cl. ........................... 134/22.1; 134/22.18
(58) Field of Search ................... 134/22.1, 22.18, 134/34, 167 R, 177, 186; 210/321.69, 636, 646

(56) References Cited

U.S. PATENT DOCUMENTS

| | | |
|---|---|---|
| 2,846,973 | 8/1958 | O'Callaghan . |
| 3,753,493 | 8/1973 | Mellor .................................. 210/140 |
| 4,158,034 | 6/1979 | Riede et al. . |
| 4,166,031 | 8/1979 | Hardy . |
| 4,375,413 | 3/1983 | Geel et al. . |
| 4,444,597 | 4/1984 | Gortz et al. . |
| 4,517,081 | 5/1985 | Amiot et al. . |
| 4,673,506 | 6/1987 | Henne et al. . |
| 4,695,385 | 9/1987 | Boag . |
| 4,707,335 | 11/1987 | Fentress et al. . |
| 4,789,467 | 12/1988 | Lindsay et al. . |
| 4,857,181 | 8/1989 | Shouldice et al. ..................... 210/87 |
| 5,139,675 | 8/1992 | Arnold et al. . |
| 5,256,371 | 10/1993 | Pippert . |
| 5,268,144 | 12/1993 | Heilmann et al. . |
| 5,336,165 | * 8/1994 | Twardowski ......................... 210/636 |
| 5,585,003 | 12/1996 | Van Newenhizen . |
| 5,589,070 | 12/1996 | Maltais et al. . |
| 5,591,344 | 1/1997 | Kenley et al. . |
| 5,605,630 | 2/1997 | Shibata ................................ 210/646 |
| 5,647,984 | * 7/1997 | Hovland et al. ..................... 210/420 |
| 5,650,071 | 7/1997 | Brugger et al. . |
| 5,651,893 | 7/1997 | Kenley et al. . |
| 5,685,835 | 11/1997 | Brugger . |
| 5,759,489 | 6/1998 | Miura et al. . |
| 5,948,247 | * 9/1999 | Gillerfalk et al. ................... 210/194 |
| 6,022,512 | * 2/2000 | Tanaka et al. ....................... 210/636 |

* cited by examiner

Primary Examiner—Randy Gulakowski
Assistant Examiner—Saeed Chaudhry
(74) Attorney, Agent, or Firm—Barbara A. Wrigley

(57) ABSTRACT

A method of cleaning precleaning the header of a used dialyzer is provided. The method includes providing a precleaner header selectively coupled to a dialyzer header cap. The precleaner header includes a needle having an inlet in fluid communication with a source of cleaning fluid and an outlet in fluid communication with the header cap. An incoming source of cleaning fluid is introduced into the needle at a pressure above ambient pressure and an incoming source of air is introduced at a pressure above ambient pressure into the incoming cleaning fluid stream. The cleaning fluid containing air is discharged into the dialyzer header and cleans the dialyzer header by circulating therewith in. A waste stream is generated and drained from the dialyzer header through the precleaner header.

19 Claims, 43 Drawing Sheets

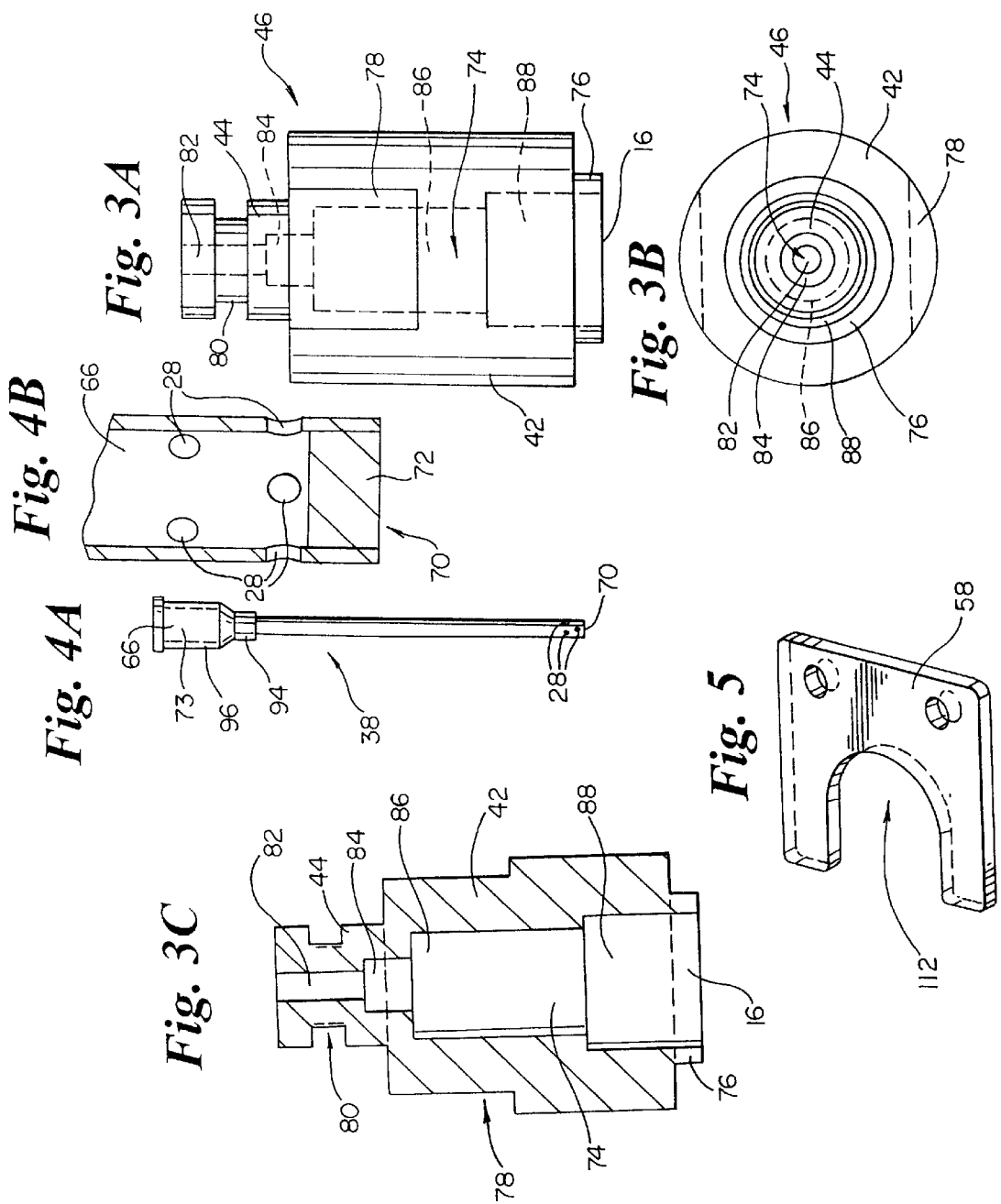

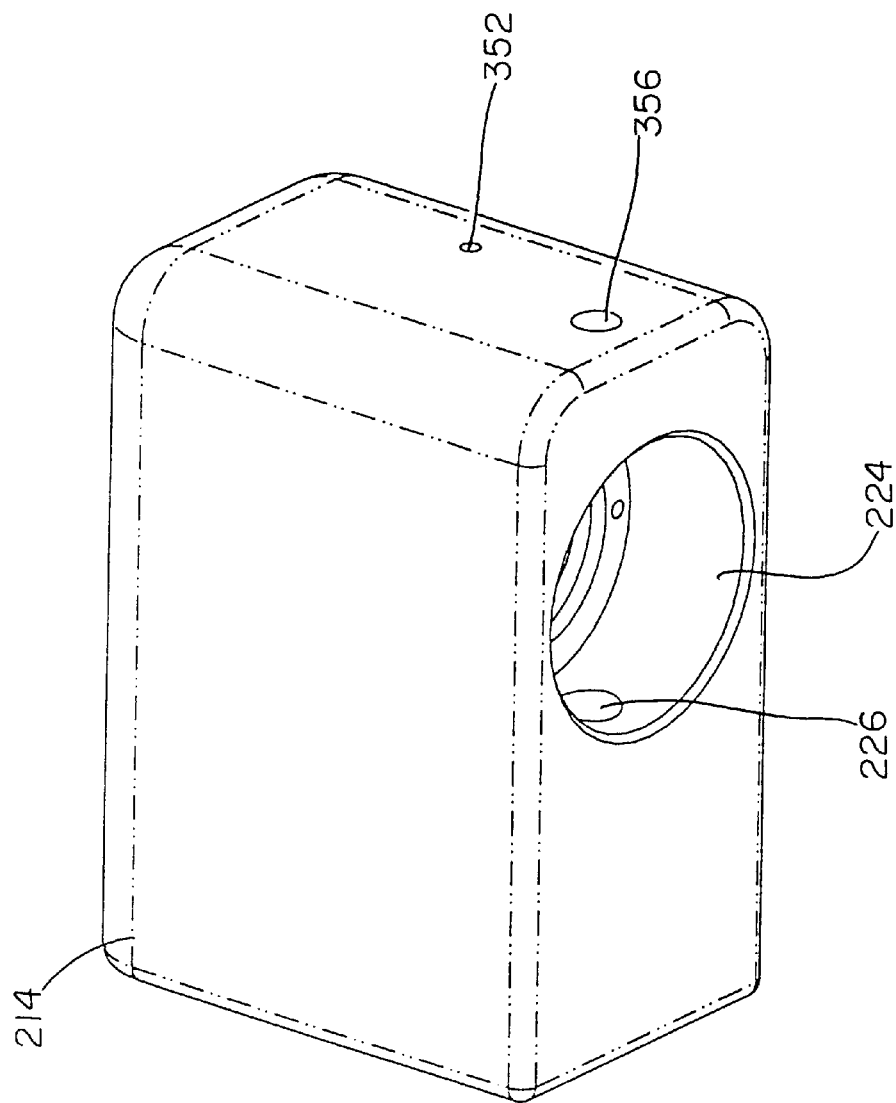

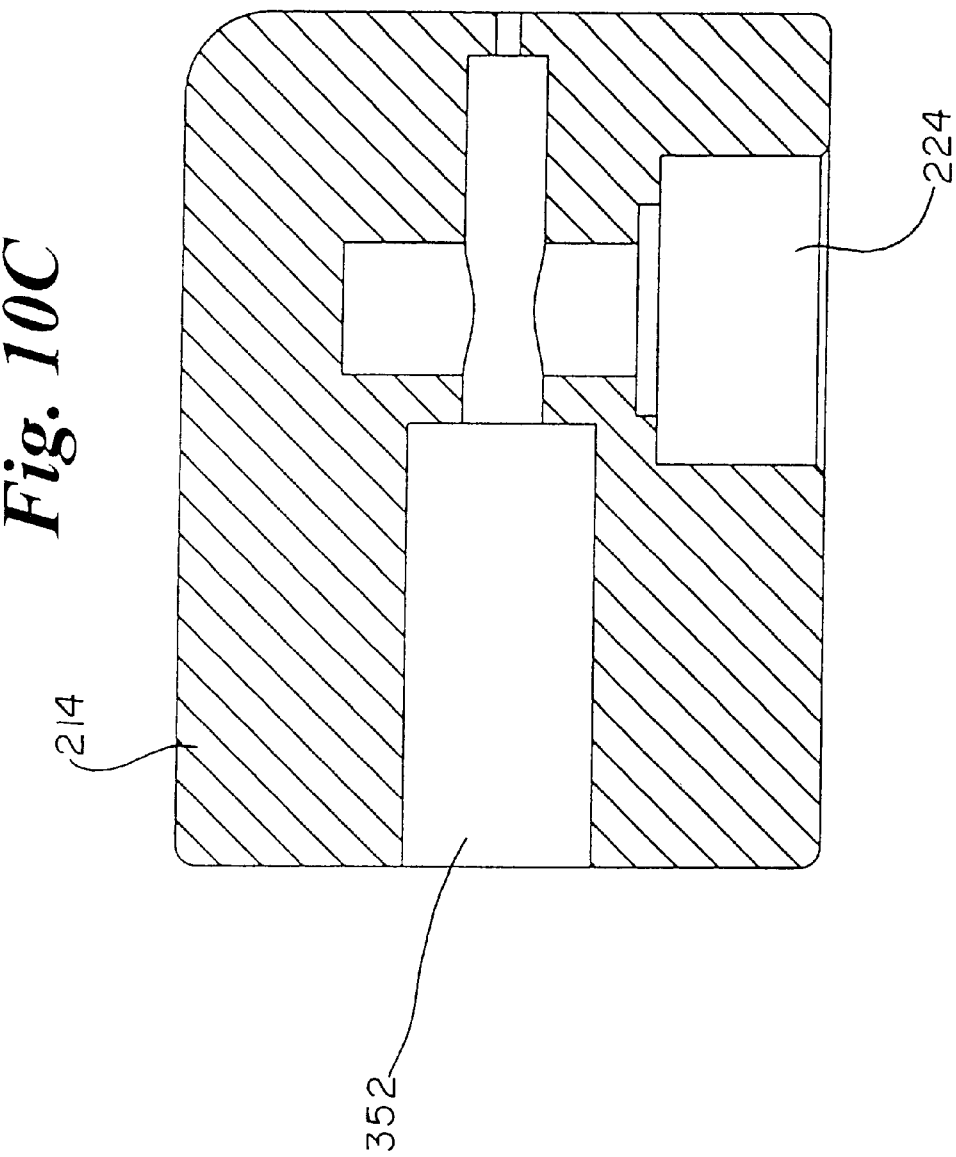

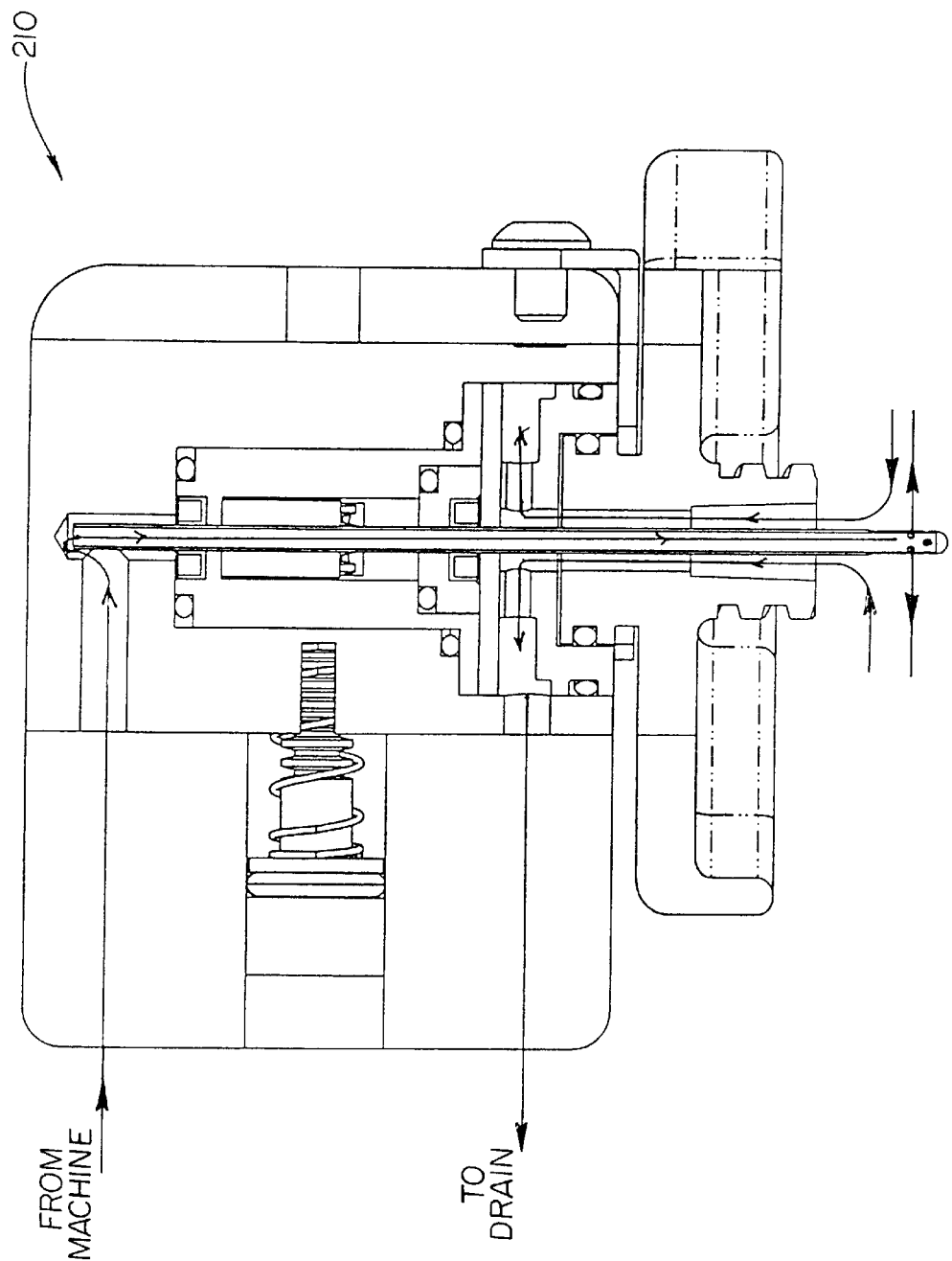

METHOD OF CLEANING A DIALYZER HEADER

This is a division of U.S. application Ser. No. 09/369,826 filed Aug. 6, 1999, now U.S. Pat. No. 6,050,278, which claims the benefit of U.S. Provisional Application No. 60/128,550, filed Apr. 9, 1999 and U.S. Provisional Application No. 60/101,624, filed Sep. 24, 1998.

BACKGROUND OF THE INVENTION

1. Field of the Invention

This invention is related generally to the field of reprocessing medical devices. In particular, it relates to a device and method for precleaning dialyzers and dialyzer headers including dialyzer header caps prior to reprocessing.

2. Description of the Related Art

Individuals requiring renal system support, or who have end-stage renal disease or acute or chronic renal failure, have kidneys that are temporarily or permanently incapable of removing products of metabolism and other substances from the blood for excretion in urine. Products of metabolism or metabolites typically include compounds such as urea, creatinine, natural biochemical metabolites, drug metabolites, and excess electrolytes. Individuals with end-stage renal disease may either undergo the replacement of a diseased kidney by transplantation of a healthy kidney, if available, or undergoing periodic hemodialysis (multiple weekly treatments) to reduce the concentration of harmful materials in the blood stream. Other individuals with trauma-induced acute renal failure need hemodialysis for brief periods of renal support.

Hemodialysis is a process in which solute molecules, which constitute undesirable waste products in human blood, are transported from the bloodstream across a hollow fiber membrane into a dialysis fluid concentrate. The aforementioned transport is accomplished by the difference in hydrostatic pressure across the membrane and the difference in chemical potential of each individual solute molecule across the membrane. Dialysis requires that membranes separating blood from dialysis fluid concentrate permit difflusional transfer of at least some of the molecular species present in blood into the fluid while effectively preventing any return contamination of blood or commingling of the blood and the dialysis fluid concentrate. Dialysis is a passive separation process with low operating costs using no external thermal or chemical energy sources. The basic hemodialysis separation obtained is between large cells and molecules, such as red blood cells, white blood cells, proteins, and small molecules such as urea, electrolytes, and other small molecule metabolites.

Hemodialysis machines control the rate of ultrafiltration while the dialyzer is the functional unit that provides a membrane capable of difflusion. Dialyzers utilize a hollow fiber membrane bundle of varying surface areas depending on the treatment modality. The generally accepted method of manufacturing hollow fiber filter dialyzers is to retain a rectilinear bundle of hollow fibers within a casing, immerse the longitudinal distal ends of the hollow fiber bundle into a potting compound which adheres to and abuts the inner surface of the casing occupying the interstitial void between the individual hollow fibers thus preventing blood contaminated with waste metabolites from coming into contact with the clean fluid concentrate or filtrate. A cross-sectional portion of the potting compound from both longitudinal ends of the potted fiber bundle is removed during the manufacturing process to provide access to the interior lumen of the individual hollow fiber membranes.

Each longitudinal end of the dialyzer is covered with a dialyzer header cap. The dialyzer header cap and the potting compound define the dialyzer header. Blood enters the dialyzer through the arterial dialyzer header cap, flows into the first dialyzer header, into the first end of the hollow fibers, through the hollow fibers, out the second end of the hollow fibers, into the second dialyzer header, and out the venous dialyzer header cap.

During dialysis, blood flows through the lumen of the hollow membrane while a dialysate fluid concentrate flows over and around the exterior surface of the hollow fiber membranes. As the blood flows through the lumen of the hollow fiber membrane, waste products from the blood diffuse through the hollow fiber membrane and into the dialysate fluid.

Everyday, dialysis centers reprocess used dialyzers so that they can be safely reused on the same patient. Reuse of dialyzers reduces healthcare costs by increasing the number of times each dialyzer may be reused before replacement. Although dialyzers can be reused on the same patient a significant number of times, dialysis centers set a predetermined maximum reuse limit as part of their dialysis procedures. However, most dialyzers fail before reaching the predetermined maximum use limit, which can vary anywhere from 10 to 100 times.

One of the major causes of premature failure is due to excessive volume loss or volume failure. Volume is used as a measure of dialyzer adequacy. Volume testing consists of measuring the total volume of the blood side of the dialyzer before it has been used and then comparing this first measurement to total blood side volume prior to each reuse.

Typically, each time a dialyzer is reused a portion of the total volume is lost. Loss of volume has been correlated to loss of mass flow transfer and loss of dialyzer efficacy. The dialyzer "fails" if the volume is less than 80% of the initial volume.

Blood clots, debris, proteins, lipids, fibrous biomasses, and other buildup within the dialyzer typically causes volume failure. The buildup also can cause blockage of the lumen of the hollow fibers. As hollow fibers become blocked or covered over repeated reuses, the total volume decreases. One factor causing loss of volume is the buildup of the aforementioned substances in the dialyzer headers including the openings to the hollow lumens. Once a hollow fiber is plugged, the reduced flow through the hollow fiber causes the other end to plug as well. Typically, once a hollow fiber is plugged, its volume is lost and further reuse is precluded.

Continual buildup may also cause secondary membrane formation. Proteins, lipids, and other such by-product masses may cause a membrane-like buildup, called a secondary membrane, to form in the dialyzer header and within the lumens of the hollow fiber membranes. This type of buildup can be difficult to remove, particularly after a number of reuses. Secondary membrane formation may cause further loss of volume and the loss of mass transfer.

Buildup in the dialyzer header, including secondary membrane formation, may also cause the loss of adequate access to the lumens of the hollow fibers for fiber cleaning. Before the lumens of the hollow fibers can be cleaned, any blockages at the ends of the hollow fibers have to be cleared away as much as possible. If the ends of the hollow fibers are plugged or partially blocked, the lumens cannot be properly flushed and cleaned. Failure to adequately remove buildup from the dialyzer header directly impacts the ability to flush and clean the hollow fibers. Once the dialyzer header has been adequately cleared of debris and buildup, the hollow fibers can be cleaned.

Continual failure to provide adequate and consistent removal of the buildup in dialyzers results in premature volume failure. As premature volume failures increase, the average number of reuses per dialyzer decreases. The average reuse number of dialyzers directly impacts healthcare costs. The average reuse of dialyzers is about 14 reuses; well short of the 25 to 35 times typically set as a maximum reuse limit.

Many dialysis technicians attempt to solve the aforementioned problems associated with reuse by manually precleaning the dialyzers before the dialyzers are sterilized and reused on patients.

In some cases, technicians remove the dialyzer header caps from the dialyzers to remove buildup, or place foreign objects into the dialyzer headers through the dialyzer header caps to clean out the buildup. These practices may result in cross-contamination or damage to the dialyzers.

If the dialyzer header caps are removed, the dialyzers are open to the clinic or hospital environment and blood may be accidentally spilled or sprayed on surrounding equipment, personnel or patients. In some cases, technicians flush open dialyzers at sinks, risking exposure to splashed or sprayed blood from the dialyzers. The exposed blood could be accidentally transferred to personnel, other dialyzers, or other patients, possibly spreading blood-borne pathogens. Transfer of blood to other patients' dialyzers could also result in adverse reactions.

Placing foreign objects into the dialyzer header caps to clean the dialyzer headers is also an undesirable practice. In many cases, using foreign objects to clean the dialyzer headers causes further blockage or damage. The foreign objects can force debris into the lumen openings of the hollow fibers or damage the hollow fibers and causing additional blockage.

Presently in clinical environments, precleaning dialyzers may include one or more of the following techniques:
  a) removing the dialyzer header caps and manually cleaning of the dialyzer headers;
  b) soaking of the dialyzers in sterilant;
  c) spraying the uncapped dialyzer headers with water or other chemicals; and
  d) other manual methods of loosening buildup such as placing foreign objects into the dialyzer headers.

These existing precleaning techniques result in low average reuse numbers due to premature volume failure caused by inadequate and inconsistent removal of buildup from the dialyzer headers. Some techniques also result in damage and further blockage of the dialyzers. Some techniques expose patients and technicians to cross contamination.

A new and useful precleaning apparatus and method is needed that overcomes the problems associated with conventional methods of precleaning dialyzers by providing i) consistent and adequate precleaning of dialyzers, ii) removal of debris and buildup from dialyzer headers including the lumen openings of the hollow fibers, iii) a sufficiently enclosed system to reduce cross contamination, and iv) a reduction in premature volume failure.

SUMMARY OF THE INVENTION

It is an object of the apparatus and method of the dialyzer precleaning system in accordance with the present invention to solve the problems outlined above that have heretofore inhibited the successful and efficient cleaning of dialyzers, dialyzer headers, and dialyzer header caps. More particularly, the apparatus and method of the dialyzer precleaning system in accordance with the present invention provides for consistent and adequate precleaning of dialyzers by removing the debris and buildup including secondary membrane formation frequently found in dialyzers and increases the number of reuses by reducing volume failure. The apparatus and method of the dialyzer precleaning system in accordance with the present invention provides for removal of debris and buildup from dialyzer headers including the openings of the lumens of the hollow fibers. The apparatus and method of the dialyzer precleaning system in accordance with the present invention provides for a sufficiently enclosed system to reduce cross contamination.

The apparatus and method in accordance with the present invention provides a device for selectively coupling a dialyzer header cap of a previously used dialyzer to a source of fluid for precleaning the previously used dialyzer.

The unique dialyzer precleaner header in accordance with the present invention broadly includes a housing, the housing defining a needle assembly receiving channel and a waste discharge channel therewith a waste discharge outlet in fluid communication with the waste discharge channel, the waste discharge channel in fluid communication with the needle assembly receiving channel, a coupling arm attached to the housing and detachably engageable with a dialyzer end cap; a needle and needle assembly received within the needle assembly receiving channel, a fluid inlet in fluid communication with the needle, and the needle defining at least one fluid discharge perforation.

The device in accordance with the present invention may also include a needle and/or a needle assembly that rotatably engages the needle assembly receiving channel so that the fluid discharge perforation may be rotated within the dialyzer header cap and the dialyzer header.

The apparatus and method in accordance with the present invention may also include a needle and/or a needle assembly that is retractably received at least partially within the needle assembly receiving channel to prevent breakage of the needle and/or the needle assembly during transport or nonuse. The needle and/or a needle assembly may also be retractably received at least partially within the needle assembly receiving channel to allow for different sized dialyzers.

The apparatus and method in accordance with the present invention may also include a needle and/or needle assembly with a plurality of fluid discharge perforations.

The apparatus and method of the present invention may also include a pneumatic connection and the needle may be rotated via pneumatic pulses to operate a rotator assembly including a piston and gear assembly.

The apparatus and method of the present invention may include a needle that is positioned in the dialyzer header by fluid pressure from the incoming stream.

The apparatus and method of the present invention may also include a coupling arm that is rotatable in relation to the housing.

The apparatus of the present invention may also include coupling arm assembly with a header spacer with a cross channel for fluidly connecting the dialyzer to the waste discharge channel.

The apparatus and method in accordance with the present invention provides a method of precleaning a previously used dialyzer. The method broadly includes providing a precleaner header selectively coupled to at least one dialyzer header cap of a previously used dialyzer; introducing an incoming stream into the precleaner header at a pressure above ambient pressure; causing the incoming stream to discharge into the dialyzer header and circulate therewith in; forming a waste stream within the dialyzer header; and draining the waste stream from the dialyzer header through the precleaner header.

The apparatus and method in accordance with the present invention may also include reverse flushing the dialyzer. Reverse flushing the dialyzer may occur during, before, or after causing the incoming stream to discharge into the dialyzer header.

The apparatus and method in accordance with the present invention may also include flushing the dialyzer using a cross flow arrangement. Flushing the dialyzer with a cross flow arrangement may occur before, or after causing the incoming stream to discharge into the dialyzer header.

The apparatus and method in accordance with the present invention may also include flushing the dialyzer from an arterial dialyzer header cap to a venous dialyzer header cap. Flushing the dialyzer from the arterial dialyzer header cap to a venous dialyzer header cap may occur before, or after causing the incoming stream to discharge into the dialyzer header.

The apparatus and method in accordance with the present invention may also occur in the order of 1) reverse flushing the dialyzer, 2) reverse flushing the dialyzer while introducing an incoming stream into the dialyzer header, 3) flushing the dialyzer using a cross flow arrangement, and 4) flushing the dialyzer from the arterial dialyzer header cap to the venous dialyzer header cap.

The apparatus and method of the present invention may also include priming the dialyzer, reverse ultrafiltration of the dialyzer, reverse ultrafiltratation of the dialyzer and simultaneously flushing the dialyzer through the precleaner header, through fiber flushing of the dialyzer, full flushing of the dialyzer, and/or disinfectant exposure of the dialyzer.

The apparatus and method of the present invention provides a dialyzer cleaning base unit for attachment to at least one precleaner header for simultaneously fluidly connecting a source of fluid and a waste discharge outlet to a dialyzer that includes a control panel for controlling the flow of fluid between the source of fluid and the dialyzer and the dialyzer and the waste discharge outlet.

The apparatus and method of the present invention provides a dialyzer cleaning system including at least one precleaner header for simultaneously fluidly connecting a source of fluid and a waste discharge outlet to a dialyzer header cap, and a control panel for controlling the flow of fluid between the source of fluid and the dialyzer and the dialyzer and the waste discharge outlet.

The apparatus and method of the present invention may also include at least one dialysate port connection for fluidly connecting the source of fluid to the dialyzer and for fluidly connecting the dialyzer to a drain.

The apparatus and method of the present invention may also include a cleaning fluid connection and/or a chemical connection.

The apparatus and method of the present invention may also provide a dialyzer cleaning position and a system cleaning/sanitizing position.

The apparatus and method of the present invention may also include a control panel that provides for a dialyzer clean cycle, a system clean cycle, a system sanitize cycle, and/or a system rinse cycle.

One advantage of the present invention is that it removes buildup of blood clots, debris, proteins, lipids, fibrous biomasses, and other buildup.

Another advantage is that the present invention breaks up buildup from inside the dialyzer and mechanically removes it via carrier solvating media.

Another advantage is that the present invention provides consistent dialyzer cleaning.

Another advantage is that the present invention is a sufficiently enclosed system to reduce cross contamination.

Another advantage is that the present invention removes secondary membrane.

Another advantage is that the present invention removes blockages from the ends of the hollow fibers.

Another advantage is that the present invention allows the precleaning of the hollow fibers.

Another advantage of the present invention is that a greater number of reuses are achieved from each dialyzer by maintaining dialyzer volumes.

These and other objects and advantages of the present invention will become apparent during the course of the following detailed description and appended claims. The invention may best be understood with reference to the accompanying drawings, wherein an illustrative embodiment is shown.

BRIEF DESCRIPTION OF THE DRAWINGS

FIG. 3A is a side view of the needle housing of the first embodiment of the precleaner header of the present invention.

FIG. 3B is a bottom view of the needle housing of the first embodiment of the precleaner header of the present invention.

FIG. 3C is a cross sectional view of the needle housing of the first embodiment of the precleaner header of the present invention.

FIG. 4A is a side view of the needle of the first embodiment of the precleaner header of the present invention.

FIG. 4B is a partial cross-sectional view of the distal end of the needle of the first embodiment of the precleaner header of the present invention.

FIG. 5 is a perspective view of the needle housing bracket of the first embodiment of the precleaner header of the present invention.

FIG. 10 is a perspective view of the housing of the second embodiment of the precleaner header of the present invention.

FIG. 10C is a cross sectional view through the center of the rotator channel of the housing of the second embodiment of the precleaner header of the present invention.

FIG. 17 is a partial cross sectional view of the inside of the of the second embodiment of the precleaner header of the present invention showing the fluid flow path.

DETAILED DESCRIPTION OF THE INVENTION

General Assembly

First Embodiment of Precleaner Header

Figure 1A:
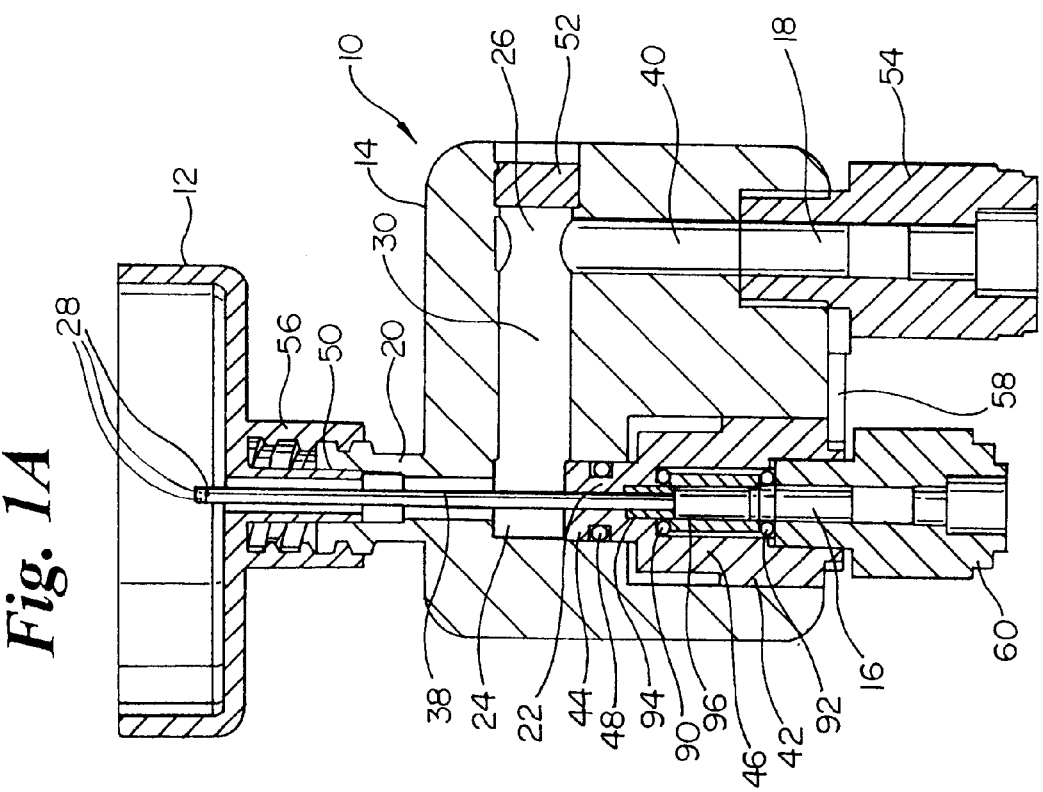
FIG. 1A is a cross sectional view of the first embodiment of the precleaner header attached to a dialyzer header cap in accordance with the present invention.
Figure 1B:
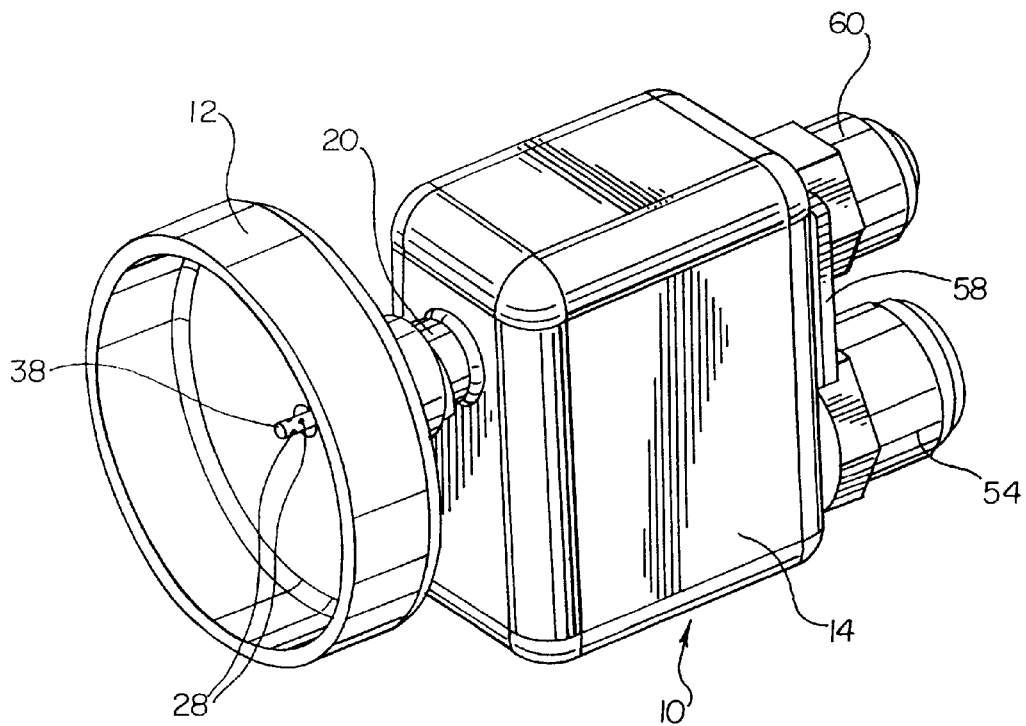
FIG. 1B is a perspective view of the first embodiment of the precleaner header attached to a dialyzer header cap in accordance with the present invention.
Figure 1C:
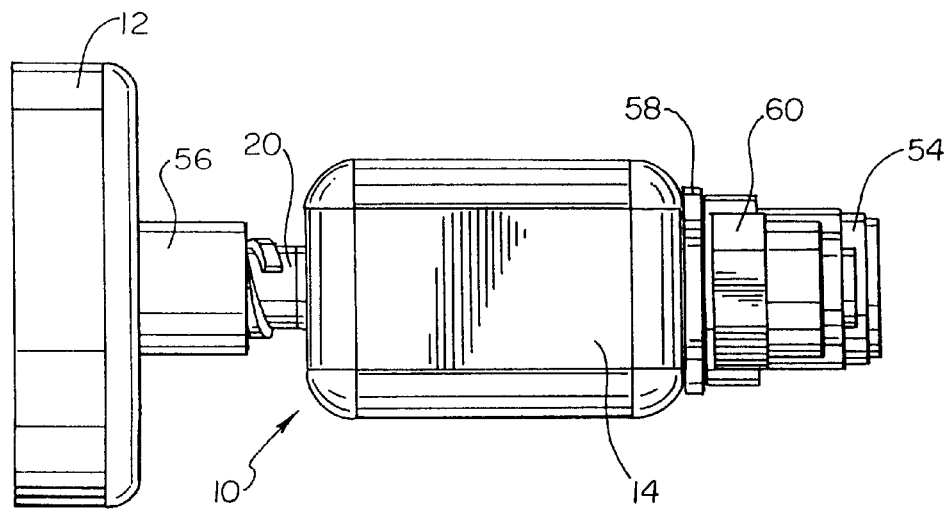
FIG. 1C is a side view of the first embodiment of the precleaner header attached to a dialyzer header cap in accordance with the present invention.

Referring to FIGS. 1A, 1B and 1C, the first embodiment of the dialyzer precleaner header 10 in accordance with the present invention is designed to be attached to a dialyzer header cap 12 and broadly includes a housing 14 with a coupling arm 20, a needle assembly 22, and a needle housing bracket 58, the housing 14 defines a needle assembly receiving channel 24 with a fluid inlet 16 and also defines a waste discharge channel 26 with a waste discharge outlet 18.

The housing 14 defines a needle assembly receiving channel 24 and a waste discharge channel 26. The fluid inlet 16 is in fluid communication with the needle assembly 22. The waste discharge outlet 18 is in fluid communication with the waste discharge channel 26. A coupling arm 20 is fixedly attached to the housing 14 and detachably engageable with the dialyzer header cap 12.

The needle assembly 22 is received within the needle assembly receiving channel 24. The needle assembly 22 defines at least one fluid discharge perforation 28, but preferably a plurality of fluid discharge perforations 28.

Housing

Figure 2:
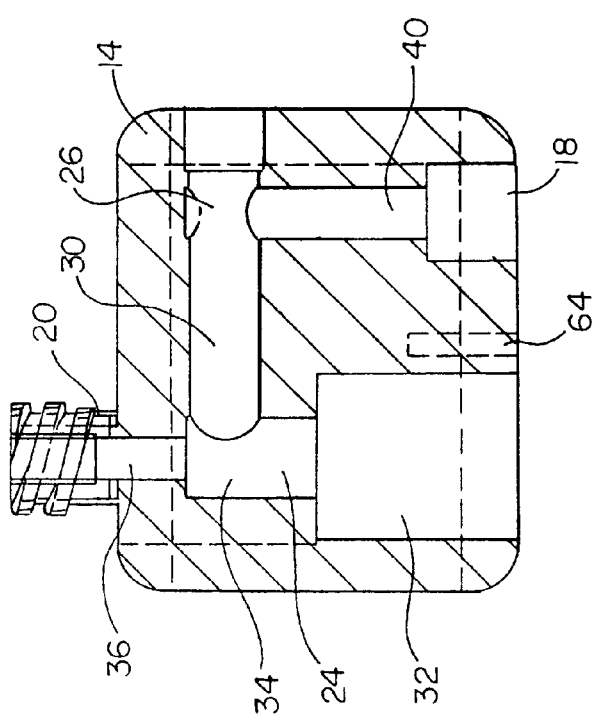
FIG. 2 is a cross sectional view of the housing of the first embodiment of the precleaner header of the present invention.

Referring to FIGS. 1A, and 2, the housing 14 defines a needle receiving channel 24 and a waste discharge channel 26. The needle receiving channel 24 and waste discharge channel 26 are in fluid communication with each other.

The needle assembly receiving channel 24 is generally a vertical cylindrical bore of varying diameter from the bottom side of the housing 14 and passing through the coupling arm 20 to the top side of the housing 14. The needle assembly receiving channel 24 consists of a base channel 32, a middle channel 34, and a needle channel 36.

The base channel 32 is generally a cylindrically shaped bore sized to receive the needle housing base 42 of the needle housing 46 and extends from the bottom of the housing 14 approximately halfway through the housing 14 and fluidly connecting to the bottom of the middle channel 34. The base channel 32 is in fluid communication with the middle channel 34.

The middle channel 34 is generally a cylindrically shaped bore sized to receive the needle housing tip 44 of the needle housing 46 and is located between the base channel 32 and the needle channel 36. The middle channel 34 is in fluid communication with base channel 32, needle channel 36, and cross channel 30. The middle channel 34 is also fluidly connected with waste discharge channel 26 by cross channel 30. The middle channel 34 is sized to allow the waste stream 104 from the dialyzer header cap 12 to flow through the needle channel 36 past the needle 38, through the middle channel 34, through the cross channel 30, through the vertical channel 40, and out the waste discharge outlet 18. The needle 38 is partially located in the needle channel 36. The middle channel 34 is also sized to receive the needle housing tip 44 in a fluid tight manner so that wastestream 104 is directed to the cross channel 30 and not back through the base channel 32 of the needle assembly receiving channel 24. The fluid tight connection may be achieved through the use of an O-ring 48 around the circumference of the needle housing tip 44.

The needle channel 36 is generally a cylindrically-shaped bore sized to allow the waste stream 104 to flow from the dialyzer header cap 12 through the needle channel 36 to the middle channel 34 and out of the precleaner header 10 as described above. The needle channel 36 is in fluid communication with middle channel 34 and the dialyzer header cap 12. The needle channel 36 is centered through the coupling arm 20 to allow waste stream 104 to return through the needle channel 36 to the waste discharge channel 26. The needle channel 36 is wider and tapered outwardly at the top end of the coupling arm 20 to mate with the inner luer flange 50 of the dialyzer cap 12.

The waste discharge channel 26 consists of a cross channel 30 and a vertical channel 40. The waste discharge channel 26 is generally a cylindrically-shaped bore of varying diameter. Cross channel 30 and vertical channel 40 are in fluid communication with each other. Cross channel 30 is in fluid communication with the middle channel 34 of the assembly receiving channel 24. Vertical channel 40 is also in fluid communication with waste discharge outlet 18.

The cross channel 30 is generally perpendicular to both the needle assembly receiving channel 24 and the vertical channel 40. The cross channel 30 fluidly connects the needle assembly receiving channel 24 with the remainder of the waste discharge channel 26. The cross channel 30 is located from the middle channel 34 of the needle assembly receiving channel 24 intersecting the top of the vertical channel 40 and ending at the side of the housing 14. The cross channel 30 intersects the middle channel 34 towards the top end of the middle channel 34 to allow room for the needle housing tip 44 the bottom of the middle channel 34. This allows waste stream 104 to pass into the cross channel 30 from the needle assembly receiving channel 24 without interference from the needle housing tip 44. The cross channel 30 intersects the vertical channel 40 at the top of the vertical channel 40. The cross channel 30 is fluidly sealed at the side of the housing 14 through either a permanent or a detachable plug 52. A detachable plug 52 would allow cleaning of the cross channel 30. However, a permanent plug 52 would reduce the number of access points for possible contamination.

The vertical channel 40 fluidly connects the cross channel 30 with the waste discharge outlet 18. The vertical channel 40 is generally parallel with the needle assembly receiving channel 24 and generally perpendicular to the cross channel 30. The vertical channel 40 is located between the cross channel 30 and the bottom of the housing 14. The vertical channel 40 intersects the cross channel 30 at a point between the middle channel 34 and the side of the housing 14. The location of the intersection should be far enough away from the side of the housing 14 to allow room for a plug 52 without interfering with the flow of waste stream 104 from the cross channel 30 to the vertical channel 40. The bottom of the vertical channel 40 may be enlarged to allow the insertion of a waste discharge outlet connector 54 at the waste discharge outlet 18.

The coupling arm 20 is located on the top of the housing 14 in vertical alignment with the needle assembly receiving channel 24. The coupling arm 20 is fixedly attached to the housing 14 and detachably engageable with the dialyzer header cap 12. The coupling arm 20 is may be integrally molded with the housing 14, or may be a separate piece that is detachable from the housing 14. The coupling arm 20 may be threaded to mate with the dialyzer header cap 12. The dialyzer header cap 12 may be attached to the coupling arm 20 so that the inner luer flange 50 of the dialyzer header cap 12 is located inside the coupling arm 20 in the needle channel 36 with the needle 38 of the needle assembly 22 located inside the inner luer flange 50. The outside of the inner luer flange 50 is drawn up against the inside of the coupling arm 20. The inside of the outer luer flange 56 of the dialyzer header cap 12 is drawn up against the outside of the coupling arm 20.

The housing 14 is preferably molded from any plastic or synthetic resin material which is sufficiently rigid and strong upon curing such as polycarbonate, polyester, or other suitable materials. The necessary channels may be drilled or molded into the housing 14.

Needle Housing Bracket

Referring to FIGS. 1A–1D and 5, the needle assembly 22 is held in place with a needle housing bracket 58. The needle housing bracket 58 keeps the needle assembly 22 from moving vertically out of the housing 14, but allows the needle assembly 22 to rotate. The needle housing bracket 58 is generally a C-shaped metal plate, preferably stainless steel. The needle housing bracket 58 is sized to fit partially over the needle assembly receiving channel 24 and around the fluid inlet connector 60 to retain the needle assembly 22 in the needle assembly receiving channel 24. The needle housing bracket 58 is attached to the housing 14 with two screws (not shown). The screws (not shown) are inserted through the needle housing bracket 58 and threaded into two screw holes 64 (FIG. 2). The screw holes 64 are defined in the housing 14 and located in the bottom of the housing 14 between the needle assembly receiving channel 24 and the waste discharge channel 26. The screw holes 64 are generally cylindrically-shaped bores located generally parallel to the needle assembly receiving channel 24 and the vertical channel 40 of the waste discharge channel 26.

Needle Assembly

Referring to FIGS. 1A, 3A–3C and 4A–4B, the needle assembly 22 consists of two main parts: a needle housing 46 and a needle 38. The needle housing 46 positions the needle 38 within the housing 14 and the dialyzer header cap 12. The needle 38 defines a hollow interior 66 with preferably a plurality of fluid discharge perforations 28 at the distal end 70 of the needle 38. The hollow interior 66 of the needle 38 is fluidly connected with the fluid inlet 16 by the needle housing channel 74. The hollow interior 66 of the needle 38 provides a passage way for the incoming stream 100 from the fluid inlet 16 through at least one fluid discharge perforation 28 in the distal end 70 of the needle 38 to the dialyzer header cap 12. The waste stream 104 returns along the outside of the needle 38, through the needle assembly receiving channel 24, and out the waste discharge channel 26. A first O-ring 48 provides a fluid seal between the needle housing 46 and the middle channel 34. First O-ring 48 prevents the waste stream 104 from leaking past the needle housing 46 through the needle assembly receiving channel 24. The needle 38 is located such that the needle base 73 is inside the needle housing channel 74.

The needle 38 and needle assembly 22 may also be constructed such that the needle 38 retracts from an extended position into a stored position. The stored position would position the needle 38 within the housing 14 to protect the needle 38 from damage while not in use. The needle 38 may be retractable into a stored position through the use of a spring or other bias means that is biased between the needle 38 and the needle housing 46. As an alternative, the entire needle assembly 22 could retract into a stored position in the needle assembly receiving channel 24. A spring could be biased between the needle assembly 22 and the housing 14. In both cases, fluid pressure from the incoming stream 100 would force the needle 38 or needle assembly 22 from a stored position into an extended position for normal use. The needle may also partially retract as shown in the second embodiment.

The needle 38 and needle assembly 22 may also be constructed such that the needle 38 automatically rotates during use. Fluid pressure from the incoming stream 100 may be used to force the needle 38 to rotate either through the use of fins or any other means using fluid pressure to cause the needle 38 or needle assembly 22 to rotate. The needle may rotate by fluid pressure such as air such as shown in the second embodiment.

Needle

Figure 6:
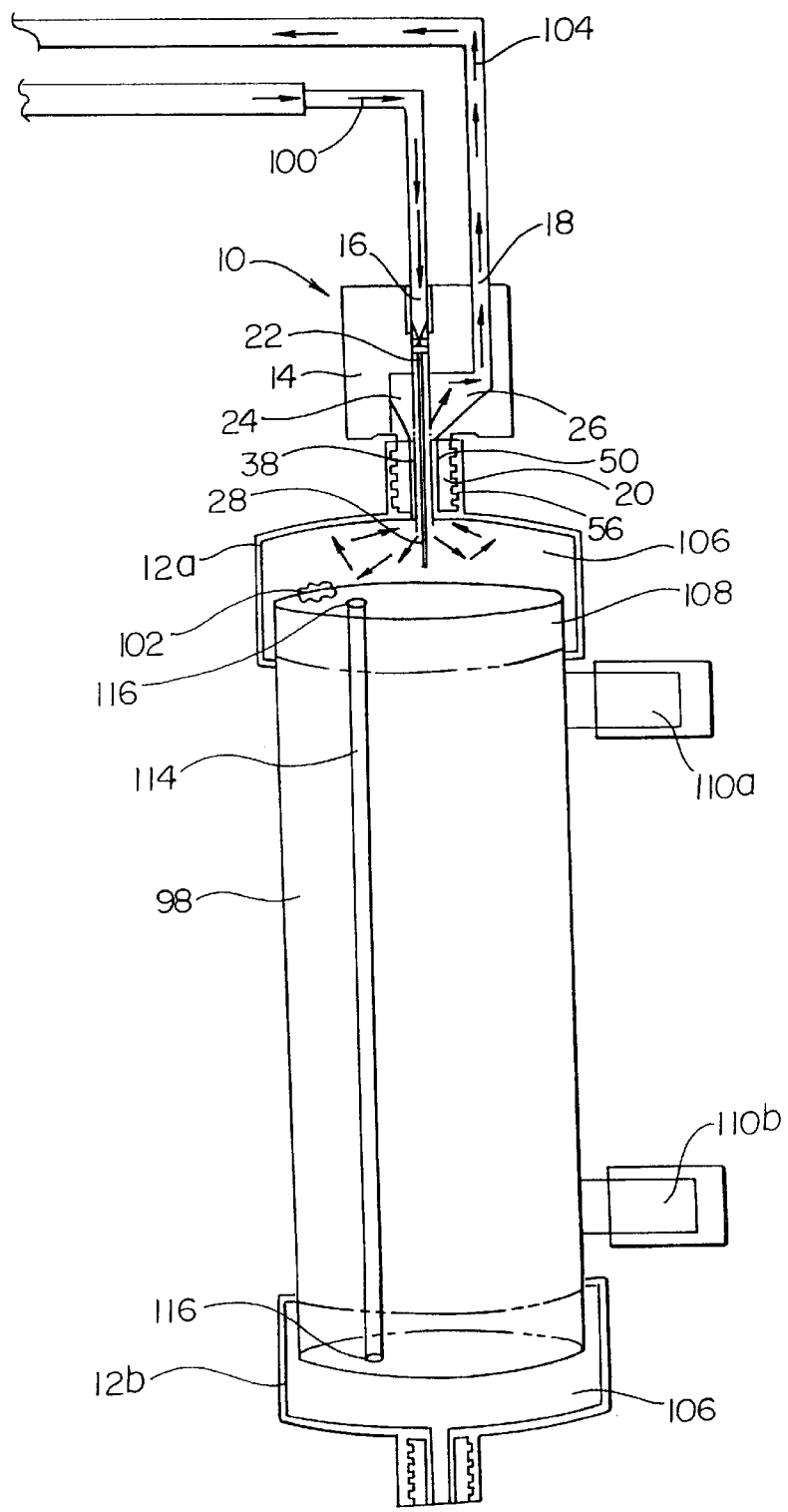
FIG. 6 is a cross sectional/schematic process view of the device of the present invention attached to a dialyzer.

Referring to FIGS. 1A, 4A–4B, the needle 38 defines a hollow interior 66. The needle 38 may be stainless steel or molded from any plastic or synthetic resin material which is sufficiently rigid and strong upon curing such as polycarbonate, polyester, or other suitable materials. The needle 38 is defined with at least one, but preferably a plurality of fluid discharge perforations 28 at the distal end 70 of the needle 38. The needle 38 may also be constructed from other materials known in the art. The needle 38 may be flexible so that the distal end 70 may randomly move about the header 106 when the incoming stream 100 is passed through the needle 38. The distal end 70 of the needle 38 is sized to fit through the inner luer flange 50 of the dialyzer header cap 12 and into the interior of a dialyzer header cap 12. Referring to FIG. 6, the dialyzer header cap 12 and the potting compound 108 of the dialyzer 98 define a dialyzer header 106. The needle 38 should be of sufficient length to extend from the needle housing 46 through the needle assembly receiving channel 24, through the coupling arm 20 and into the dialyzer header cap 12 and the dialyzer header 106. The distal end 70 of the needle 38 should extend into the dialyzer header cap 12 and dialyzer header 106. The needle 38 should sufficiently extend into the dialyzer header cap 12 and dialyzer header 106 so that the incoming stream 100 exiting from the fluid discharge perforations 28 in the needle 38 can sufficiently clean the interior of the dialyzer header cap 12 and dialyzer header 106. The needle 38 is preferably about 2.57 inches in length with an inside diameter of about 0.063 inches and an outside diameter of about 0.083 inches. The fluid discharge perforations 28 are preferably 0.02 inch in diameter with four fluid discharge perforations 28 located 0.055 inch from the distal end 70 and four more fluid discharge perforations 28 located 0.115 inch from the distal end 70 of the needle 38. The fluid discharge perforations 28 are preferably evenly spaced about the circumference of the needle 38 at 90 degrees from each other with the two rows offset by 45 degrees from each other. The distal end 70 of the needle 38 is plugged with a needle plug 72, either stainless steel or a suitable plastic or synthetic resin material.

The needle also has a needle base 73. The needle base 73 is preferably stainless steel or a suitable plastic or synthetic resin material with a narrow portion 94 and a wider portion 96. The hollow interior 66 of the needle 38 is defined through the needle base 73 of the needle 38.

Needle Housing

Referring to FIGS. 1A, 2, 3A–3C and 4A–4B, the needle housing 46 positions the needle 38 within the housing 14, the dialyzer header cap 12, and the dialyzer header 106 and provides a fluid connection between the needle 38 and the fluid inlet 16. The needle housing 46 is generally cylindrically-shaped with a needle housing channel 74 defined vertically through the center of the needle housing 46. The needle housing channel 74 is generally a vertical cylindrically shaped bore through the center of the needle housing 46. The needle housing 46 is molded from any plastic or synthetic resin material which is sufficiently rigid and strong upon curing such as polycarbonate, polyester, or other suitable materials. The necessary channels may be drilled or molded into the needle housing 46.

The needle housing 46 generally consists of three sections: The needle housing base 42, the needle housing tip 44 and the needle housing bottom lip 76.

The needle housing base 42 is generally sized and shaped to fit into the base channel 32 of the housing 14. The length of the needle housing base 42 is approximately the same as the length of the base channel 32. The top of the needle housing base 42 is positioned against the top of the base channel 32. The bottom of the needle housing base 42 is positioned adjacent to the bottom of the base channel 32.

The needle housing base 42 also may define planar surfaces 78 molded or ground into the side of the needle housing base 42. These planar surfaces 78 provide wrench gripping surfaces for easier threading and attachment of a fluid inlet connector 60 to the needle housing 46. The planar surfaces 78 are located along the sides of the needle housing base 42 and extend approximately half the length of the needle housing base 42 from the top of the needle housing base 42.

The needle housing tip 44 is located on top of the needle housing base 42 and is shaped to fit into the middle channel 34 of the housing 14. The needle housing tip 44 is integrally molded with the needle housing 46. The needle housing tip 44 is generally cylindrical and has a recessed groove 80 about its circumference approximately midway along the length of the needle housing tip 44. The recessed groove 80 is sized to receive a first O-ring 48. The needle housing tip 44 in conjunction with the first O-ring 48 provides a fluid seal between the middle channel 34 and the needle assembly 22.

The needle housing bottom lip 76 is located at the bottom of the needle housing 46. The needle housing bottom lip 76 is designed to provide a smaller circumference edge so that the needle housing bracket 58 may hold the needle housing 46 in place. The length of the needle housing bottom lip 76 is approximately the same as the width of the needle housing bracket 58. The needle housing bottom lip 76 is designed to fit in the C-shaped opening 112 of the needle housing bracket 58. The diameter of the needle housing bottom lip 76 is therefore less than the C-shaped opening 112 of the needle housing bracket 58.

The needle housing channel 74 is a vertical cylindrical channel of varying diameter through the center of the needle housing 46. The needle housing channel 74 provides fluid communication between the needle 38 and the fluid inlet 16. There are four different areas to the needle housing channel 74, an upper portion 82, a second portion 84, a third portion 86, and a bottom portion 88. The upper portion 82 of the needle housing channel 74 is designed to partially receive a portion of the main length of the needle 38. The second portion 84 is designed to receive the top narrow portion 94 of the needle base 73 of the needle 38. The third portion 86 is designed to receive the wider portion 96 of the needle base 73 of the needle 38. The bottom portion 88 is designed to receive the fluid inlet connector 60. A second O-ring 90 may be placed around the circumference of the needle base 73 at the shoulder created between the narrow portion 94 and the wider portion 96 of the needle base 73. This second O-ring 90 contacts the top of the third portion 86 of the needle housing channel 74. Second O-ring 90 provides a fluid tight seal between the needle base 73 and the needle housing channel 74. Second O-ring 90 keeps the waste stream 104 from the needle assembly receiving channel 24 from passing through the needle housing channel 74. A third O-ring 92 may be placed between the bottom of the needle base 73 and the fluid inlet connector 60. The third O-ring 92 is located at the top of the bottom portion 88 of the needle housing channel 74. The third O-ring 90 provides a fluid seal between the needle base 73 and the fluid inlet connector 60 keeping the incoming stream 100 from leaking into the needle assembly receiving channel 24.

Fluid Inlet Connector

Referring to FIGS. 1A–1C, the fluid inlet connector 60 is located at the fluid inlet 16. The fluid inlet 16 is the opening located at the bottom of the needle housing channel 74. The fluid inlet connector 60 is in fluid communication with the needle housing 46 through the needle housing channel 74. The fluid inlet connector 60 is preferably threadably attached to the needle housing 46. The fluid inlet connector 60 is preferably of standard construction and ¼×⅛ NPT in size. The fluid inlet connector 60 is designed to provide quick access to an incoming stream supply line (not shown). The incoming stream 100 may also contain a gas to enhance cleaning. Preferably, the incoming stream 100 is a pulsating stream of water and air.

Waste Outlet Connector

Referring to FIGS. 1A–1C, the waste discharge outlet connector 54 is located at the waste discharge outlet 18. The waste discharge outlet 18 is the opening located at the bottom of the waste discharge channel 26. The waste discharge outlet connector 54 is in fluid communication with the waste discharge outlet 18 through the waste discharge channel 26. The waste discharge connector 54 is preferably threadably attached to the housing 14. The waste outlet connector 54 is preferably of standard construction and ⅜×¼ NPT in size. The waste outlet connector 54 is designed to provide quick access to a waste discharge hose line (not shown).

Second Embodiment of Precleaner Header

The second embodiment of the dialyzer precleaner header 210 is shown in FIGS. 7 to 17. As shown in FIGS. 7, 8, 8A, and 9, particularly FIGS. 7 and 8A, the dialyzer precleaner header 210 in accordance with the present invention is designed to be attached to a dialyzer header cap 12 (See FIG. 18) and broadly includes a housing 214, a needle assembly 222, a rotator assembly 219, a coupling arm assembly 358, a bracket 258, a fluid inlet connector 390, a waste discharge connector 392, and an air connector 394.

Housing

The housing 214 is shown in further detail in FIGS. 10, 10A, 10B, and 10C. The housing 214 may be molded from any plastic or synthetic resin material which is sufficiently rigid and strong upon curing such as polycarbonate, polyester, or other suitable materials. Preferably, the housing 214 is molded from DELRIN® resin. The necessary channels may be drilled or molded into the housing 214. The housing 214 is a generally rectangular block with rounded edges and also has several channels defined within the housing 214. The channels include a needle assembly receiving channel 224, a rotator assembly channel 352, a fluid supply channel 354, a waste discharge channel 226, and a bracket screw hole 356. The housing 214 also defines a fluid inlet 216 for the fluid supply channel 354, and a waste discharge outlet 218 for the waste discharge channel 226.

Needle Assembly Receiving Channel

The needle assembly receiving channel 224 is a generally cylindrical bore of varying diameter for receiving the needle assembly 222 and the coupling arm assembly 358. The needle assembly receiving channel 224 extends vertically almost entirely through the housing 214. The fluid supply channel 354 intersects with and is fluidly connected to the top of the needle assembly receiving channel 224, top being the direction away from the dialyzer 98. The rotator assembly channel 352 intersects with the middle of the needle assembly receiving channel 224. The rotator assembly channel 352 receives the rotator assembly 318 so that the piston 350 of the rotator assembly 318 mates with the gear 334 of the needle assembly 222. The rotator assembly channel 352 is off centered in relation to the needle assembly receiving channel 224 so that the piston 350 mates with the gear 334. The needle assembly receiving channel 224 also intersects and is fluidly connected to the waste discharge channel 226 near the bottom of the needle assembly receiving channel 224.

Figure 9:
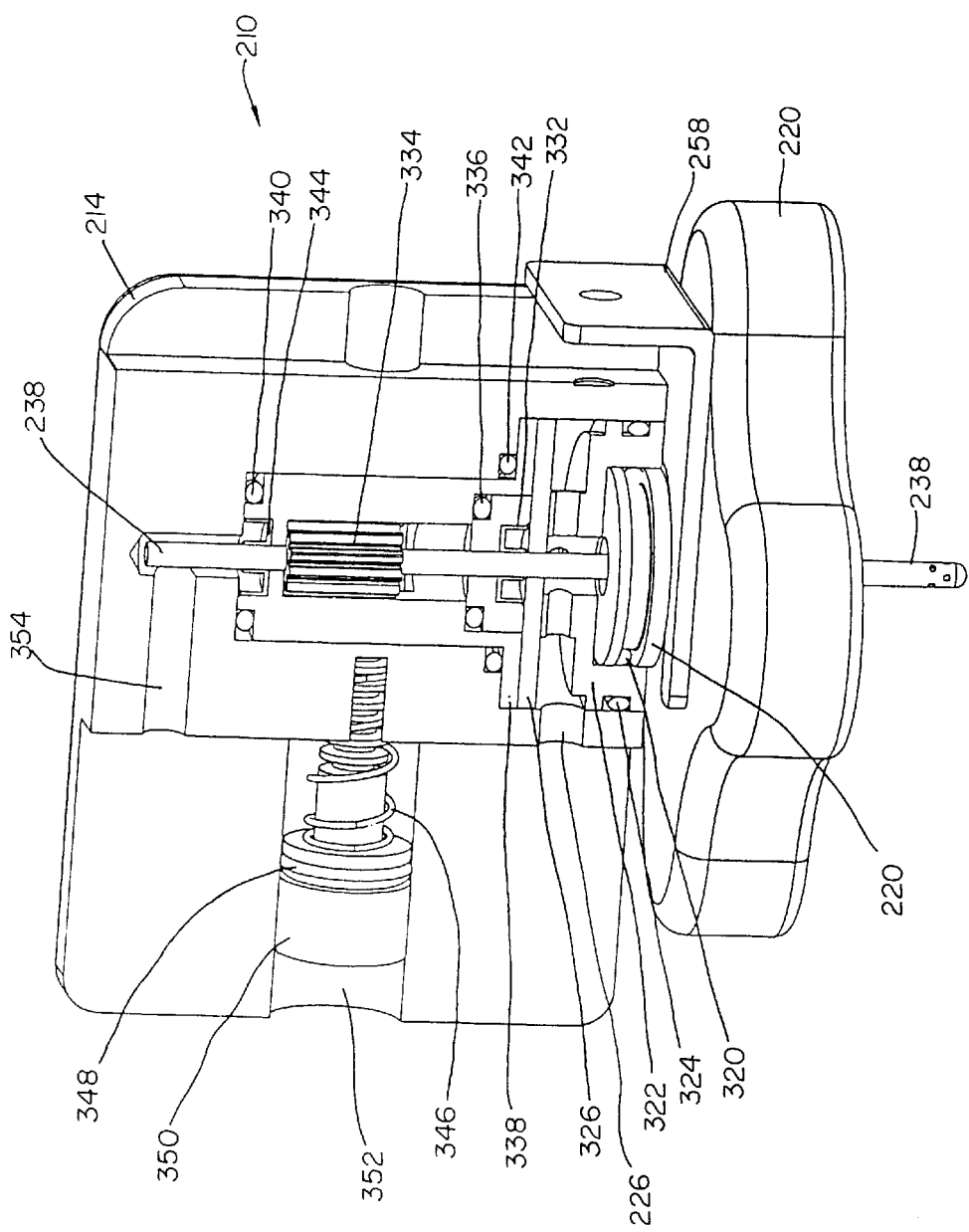
FIG. 9 is a partial perspective view of the second embodiment of the precleaner header of the present invention.

As shown in FIG. 9, the needle assembly receiving channel 224 is sized to receive the needle assembly 222 and the coupling arm assembly 358.

Rotator Assembly Channel

As shown in FIG. 10C, The rotator assembly channel 352 is a generally horizontal cylindrical bore of varying diameter extending through the housing 214. The opening at the distal end of the rotator assembly channel 352, the end away from the air connector 394, may be reduced in size for appearance as shown in FIGS. 10 and 10C, or may be the same size as the piston portion for machining convenience as shown in FIGS. 8A and 9. The rotator assembly channel 352 is off centered from the needle assembly receiving channel 224 so that the piston 350 of the rotator assembly 318 mates with the gear 334 of the needle assembly 222. The rotator assembly channel 352 is designed to receive the rotator assembly 318.

Fluid Supply Channel & Fluid Inlet

Figure 10A:
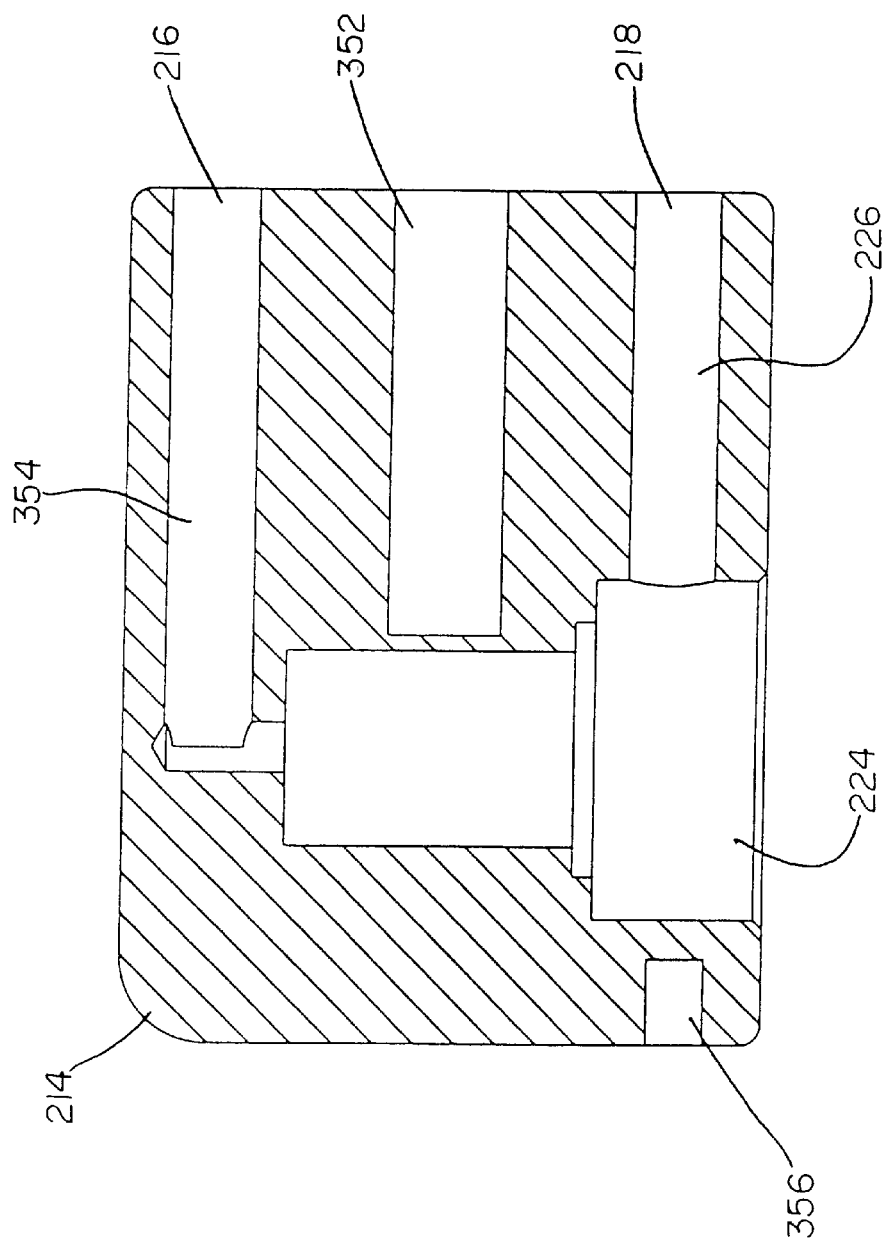
FIG. 10A is a cross sectional view through the center of the needle assembly channel of the housing of the second embodiment of the precleaner header of the present invention showing the various channels.
Figure 10B:
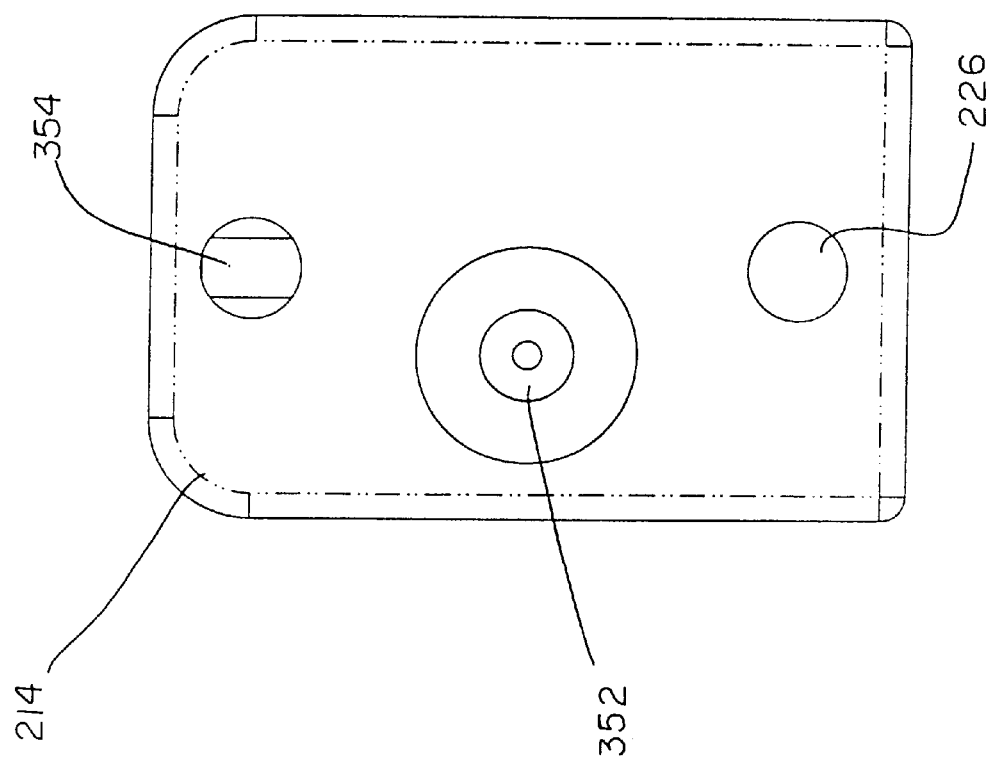
FIG. 10B is an end view of the housing of the second embodiment of the precleaner header of the present invention.

As shown if FIG. 10A, the fluid supply channel 354 extends from the side of the housing 214 to near the top of the needle assembly receiving channel 224. The fluid supply channel 354 is a generally horizontal cylindrical bore with a diameter of about 0.146 inches. The fluid inlet 216 is the opening of the fluid supply channel 354 at the side of the housing 214. The fluid supply channel 354 fluidly connects the fluid inlet 216 to the needle assembly receiving channel 224.

Waste Discharge Channel & Waste Discharge Outlet

As shown in FIG. 10A, the waste discharge channel 226 extends from the side of the housing 214 to near the bottom of the needle assembly receiving channel 224. The waste discharge channel 226 is a generally horizontal cylindrical bore with a diameter of about 0.146 inches. The waste discharge outlet 218 is the opening of the waste discharge channel 226 at the side of the housing 214. The waste discharge channel 226 fluidly connects the needle assembly receiving channel 224 to the waste discharge outlet 218.

Bracket Screw Hole

The bracket screw hole 356 is a generally horizontal cylindrical bore located towards the bottom of the side of the housing 214. The bracket screw hole 356 is sized to receive the bracket screw 360.

Needle Assembly

Figure 8:
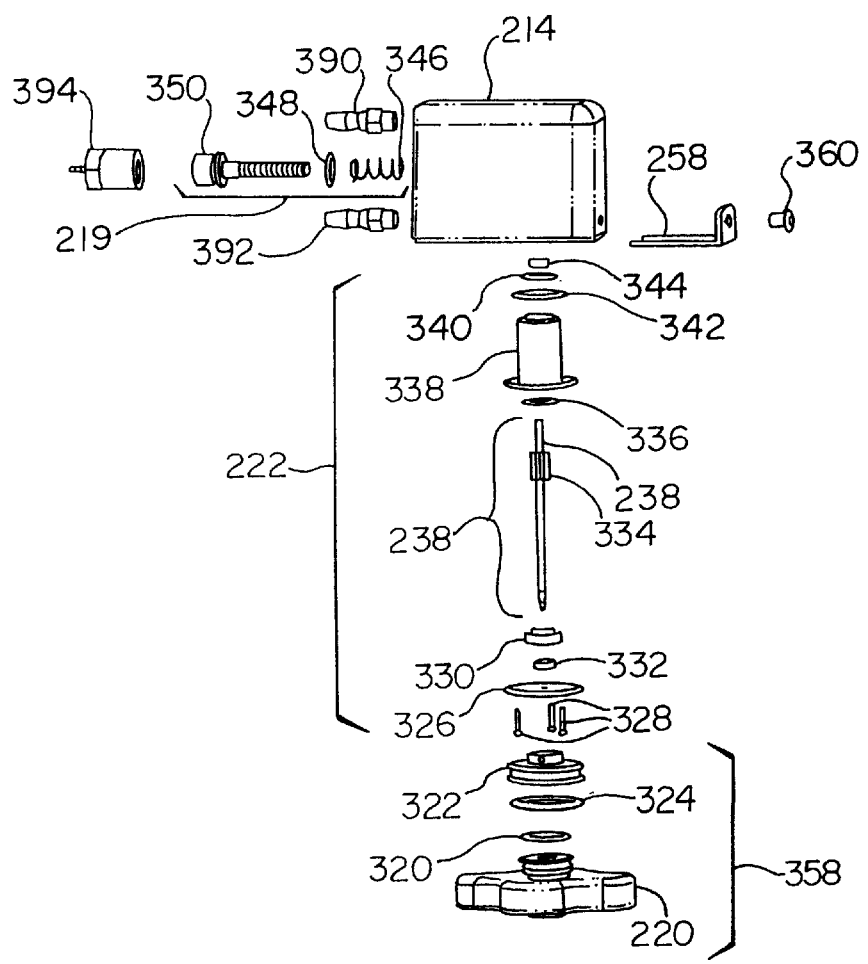
FIG. 8 is an exploded view of the second embodiment of the precleaner header of the present invention.
Figure 8A:
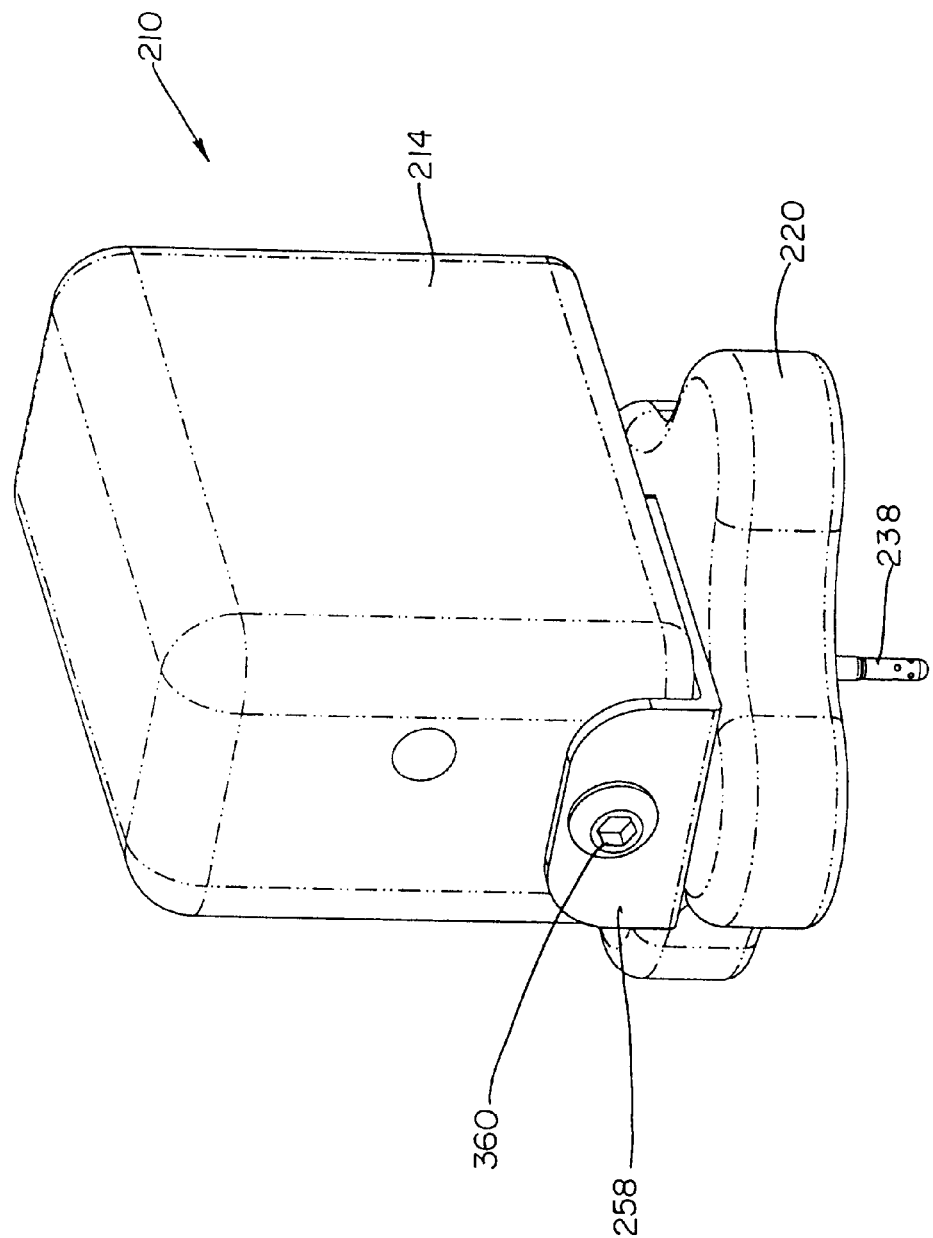
FIG. 8A is a perspective view of the second embodiment of the precleaner header of the present invention.

The needle assembly 222, as shown in FIG. 8, is comprised of several parts including an upper seal 344, a first O-ring 340, a second O-ring 342, a gear sleeve 338, a third O-ring 336, a needle 238 with an attached gear 334, a lower seal housing 330, a lower seal 332, a bolt plate 326, and bolt plate screws 328.

Needle and Gear

Figure 11:
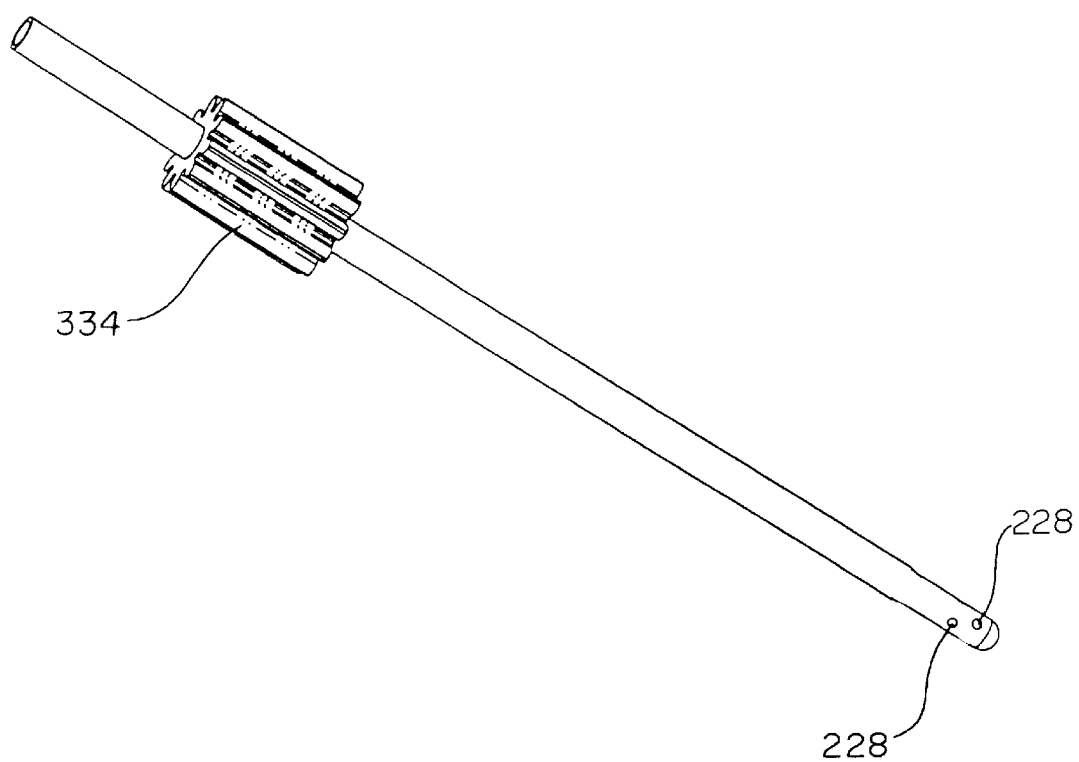
FIG. 11 is a perspective view of the needle of the second embodiment of the precleaner header of the present invention.

The needle 238, as shown in FIG. 11, is preferably manufactured from 304 stainless steel with a hollow interior with one open end and one perforated end. The needle 238 is approximately 2.75 inches long with an outside diameter of 0.083 to 0.095 inches, preferably 0.095 inches and an inside diameter of 0.064 to 0.085 inches, preferably 0.085 inches. The needle 238 has a plurality of fluid discharge perforations 228 located near the perforated end. There may be two rows of four discharge perforations 228 each with a diameter of 0.023 inches or preferably, two rows of two perforations 228 with the top row of perforations 228 having a diameter of 0.032 inches and the bottom row of holes having a diameter of 0.028 inches. If four perforations are used, the perforations 228 in each row are preferably located 90 degrees apart with the two rows offset by 45 degrees. If two rows of two perforations 228 are used, the perforations in each row are preferably located 180 degrees apart with the rows offset by 90 degrees. The inside of the perforated end of the needle 238 preferably has an inverted cone to reduce turbulent flow in the tip of the needle 238. The gear 334 is welded to the needle about 0.475 to 0.500 inches, preferably 0.500 inches from the open end of the needle 238. The gear 334 is designed to mate with the piston 350. The piston 350 and gear 334 combination transfers the reciprocal motion of the piston 350 created by pulsating fluid such as air, into rotational motion of the needle 238. As fluid is pulsated into the rotator assembly channel 352, the needle 238 rotates back and forth.

Gear Sleeve

Figure 15:
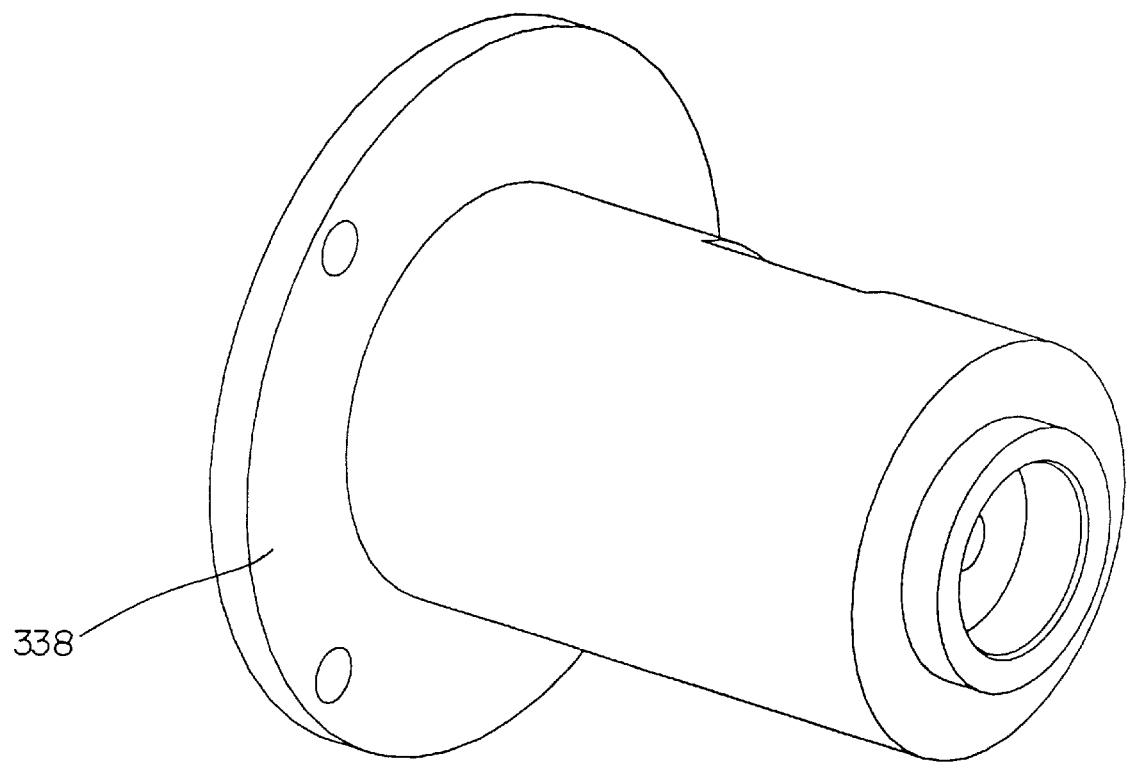
FIG. 15 is a perspective view of the gear sleeve of the second embodiment of the precleaner header of the present invention.
Figure 15A:
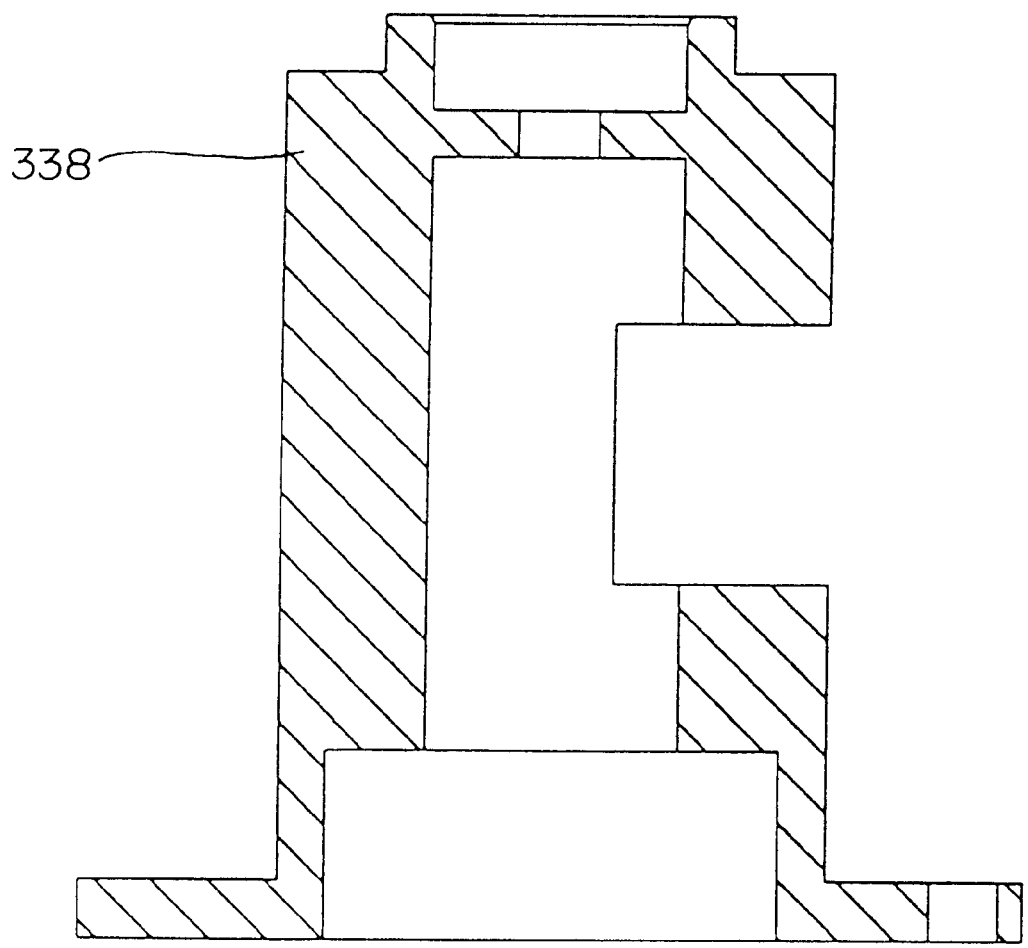
FIG. 15A is a cross sectional view of the gear sleeve of the second embodiment of the precleaner header of the present invention.

The gear sleeve 338, as shown in FIGS. 15 and 15A, is a generally cylindrical hollow tube with a flange. The gear sleeve 338 holds the needle 238 and gear 334 in vertical alignment while allowing the needle 238 to rotate about and translate along its vertical axis. The gear sleeve 338 is designed to receive the needle 238 and gear 334 inside the hollow portion of the gear sleeve 338. The flange includes screw holes for attachment of the gear sleeve 338 inside the needle assembly receiving channel 224 of the housing 214. The gear sleeve 338 is also designed to receive the lower seal housing 330 inside the flange end of the hollow portion. The gear sleeve 338 also has a cutout portion so that the piston 350 has access to the gear 334. The gear sleeve 338 is designed to receive the needle 238 and gear 334 such that the gear may translate vertically within the gear sleeve 338.

Bolt Plate and Bolt Plate Screws

As shown in FIG. 8, the bolt plate 326 is a flat cylindrical disk designed to secure the needle assembly 222 in the housing 214. The bolt plate 326 has three screw holes spaced about the perimeter of the bolt plate 326 and an opening for the needle 238 through the center of the bolt plate 326. The screw holes are designed to mate with screw holes in the gear sleeve 338 and the housing 214. The screw holes are not equally spaced so that the cutout in the gear sleeve 338 may be consistently properly aligned with the rotator assembly 219.

Lower Seal Housing

Figure 16:
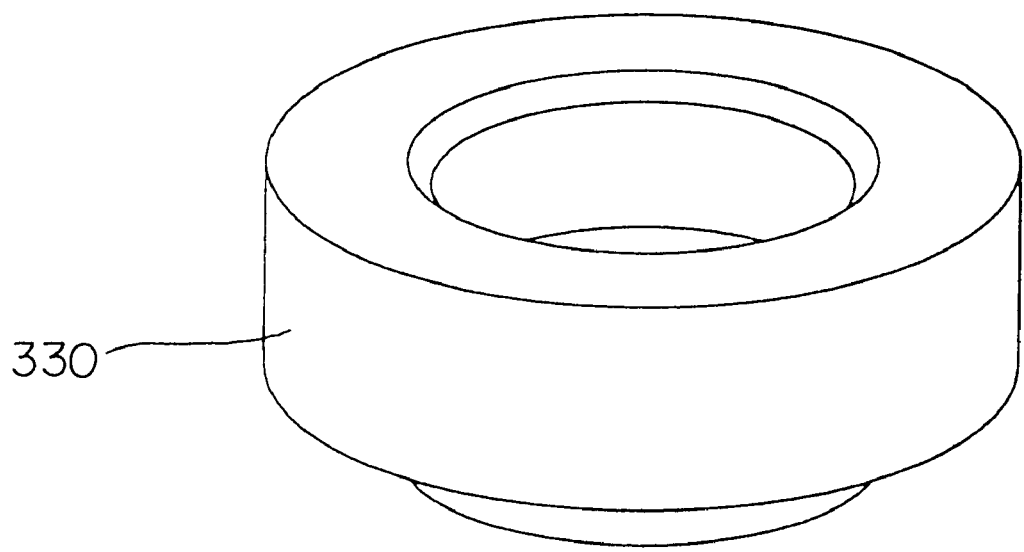
FIG. 16 is a perspective view of the lower seal housing of the second embodiment of the precleaner header of the present invention.
Figure 16A:
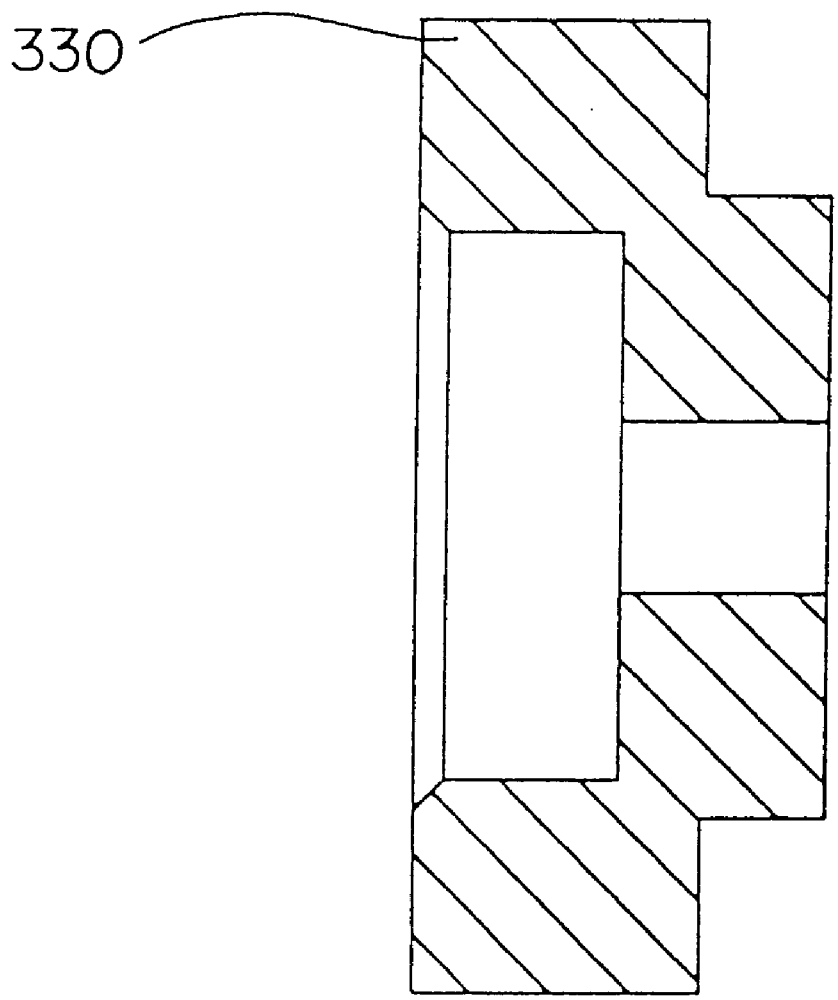
FIG. 16A is a cross sectional view of the lower seal housing of the second embodiment of the precleaner header of the present invention.

As shown in FIGS. 16 and 16A, the lower seal housing 330 is a generally hollow cylindrical disk. The lower seal housing 330 is sized to be received within the gear sleeve 338 as shown in FIG. 9. The lower seal housing 330 provides a lower limit for the translational movement of the gear 334 and needle 238 and also provides a recess for receiving the lower seal 332. The lower seal housing 330 is held in place between the bolt plate 326 and the gear sleeve 338.

Upper Seal and Lower Seal

As shown in FIGS. 8 and 9, the upper seal 344 and lower seal 332 are generally cylindrically shaped disks with a hole through the center of the seals 344, 332 sized to receive the needle 238. The upper seal 344 is sized to be received between the gear sleeve 338 and the housing 214. The lower seal 332 is sized to be received in the lower seal housing 330 between the lower seal housing 330 and the bolt plate 326. The seals 344, 332 provide wear surfaces and fluid seals around the needle 238.

O-rings First Through Third

As shown in FIGS. 8 and 9, The first, second, and third O-rings 340, 342, 336 provide fluid seals between the needle 238, needle assembly 222 and the housing 214. The O-rings 340, 342, 336 are typical O-rings used in the medical industry. The first O-ring 340 provides a fluid tight seal between the top of the gear sleeve 338 and the housing 214, keeping fluid from leaking down the needle assembly receiving channel 224 into the rotator assembly channel 352. The second O-ring 342 provides a fluid tight seal between the flange of the gear sleeve 338 and the housing 214, keeping waste fluid from leaking up the needle assembly receiving channel 224 into the rotator assembly channel 352. The third O-ring 336 provides a fluid tight seal between the bottom seal housing 330 and the gear sleeve 338, keeping waste fluid from leaking up the needle assembly receiving channel 224 into the rotator assembly channel 352.

Rotator Assembly

The rotator assembly 219, as shown in FIGS. 8 and 9, includes a piston 350, a sixth O-ring 348 and a spring 346.

Figure 12:
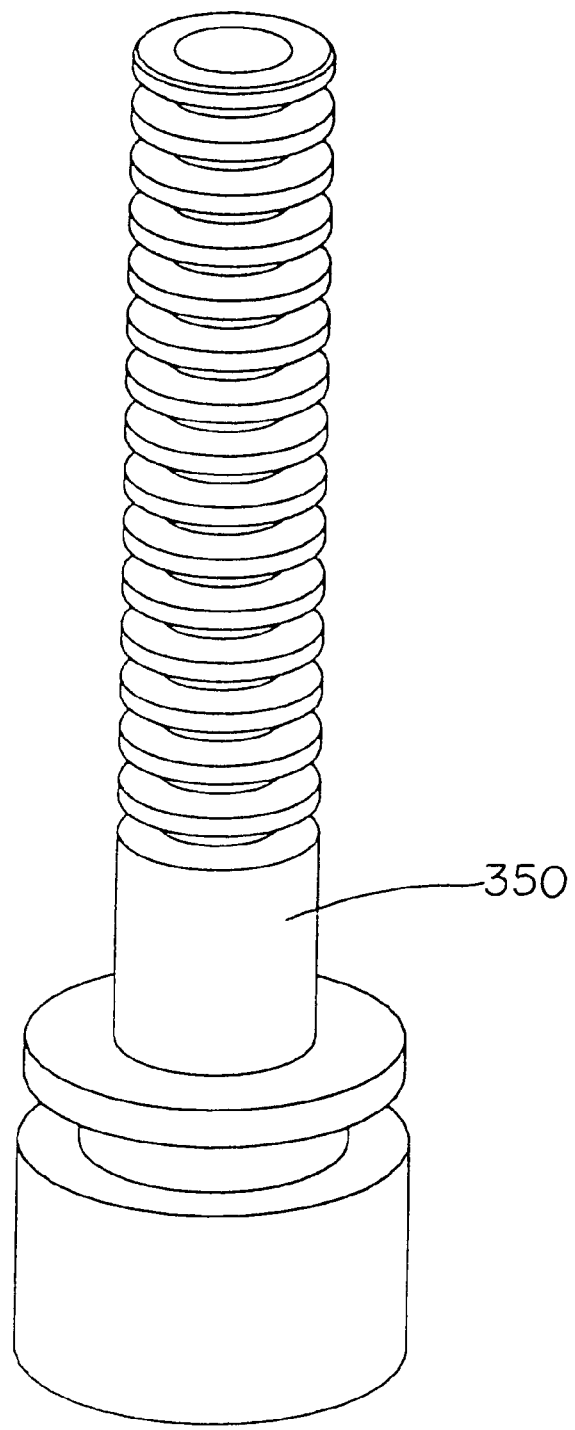
FIG. 12 is a perspective view of the piston of the second embodiment of the precleaner header of the present invention.

The rotator assembly is sized to be received in the rotator assembly channel 352. The rotator assembly 219 is designed to mate with the gear 334 of the needle assembly 222 so that the translational movement of the piston 350 is transferred into rotational movement of the needle 238. The piston 350 is reciprocated in the rotator assembly channel 352 by pulsating air applied to the rotator assembly channel 352. The spring 346 is compressed as the force from the air pressure pushes against the spring 346, moving the piston 350 to a compressed position. When the air pressure is reduced, the force of the compressed spring 346 returns the piston 350 to the extended position. As shown in FIG. 12, the piston 350 is made from 316 stainless steel and has a plurality of teeth defined along the shaft of the piston 350. The teeth circumscribe the shaft of the piston 350 and are transverse to the axis of the piston 350 and are designed to mate with the teeth of the gear 334 of the needle assembly 222 as shown in FIGS. 9 and 17. The piston 350 has a groove in the base of the piston 350 for receiving a sixth O-ring 348. The sixth O-ring 348 is sized to fit the groove and provide a fluid tight seal between the piston 350 and the rotator assembly channel 352. The spring 346 is sized to bias between the base of the piston 350 and the housing 214. The spring 346 is a coil-type spring and is sized to fit over the shaft of the piston 350. The piston 350 may cycle at any reasonable frequency, but preferably from about 0.5 to about 2 Hz and most preferably about 1 Hz.

Coupling Arm Assembly

The coupling arm assembly 358, as shown in FIGS. 8 and 9, includes a coupling arm 220, a fourth O-ring 320, a fifth O-ring 324, and a header spacer 322.

Figure 13:
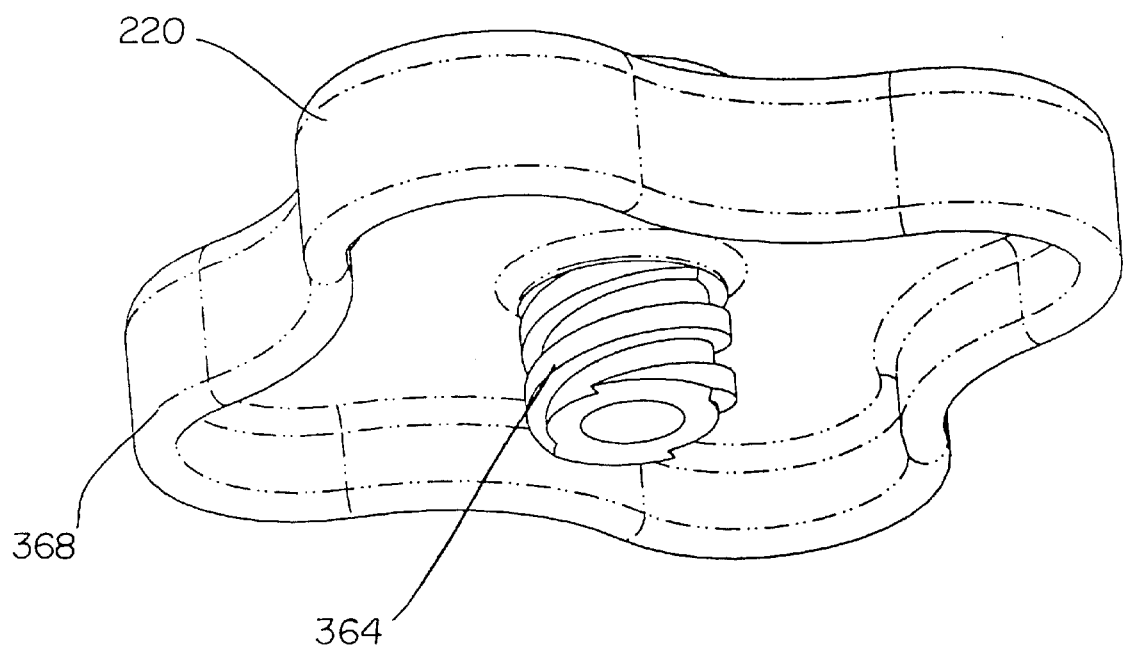
FIG. 13 is a perspective view of the coupling arm of the second embodiment of the precleaner header of the present invention.
Figure 13A:
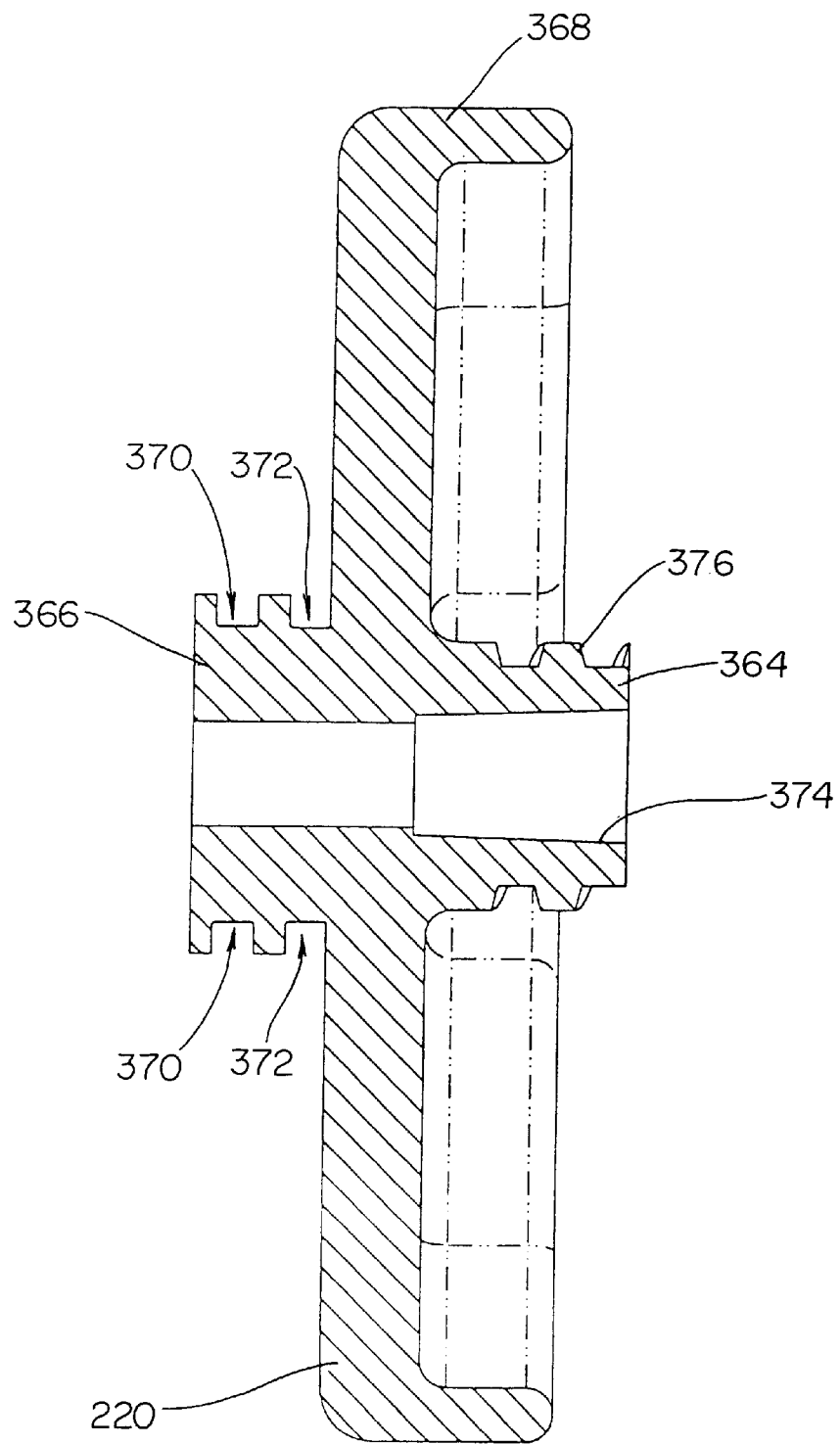
FIG. 13A is a cross sectional view of the coupling arm of the second embodiment of the precleaner header of the present invention.
Figure 13B:
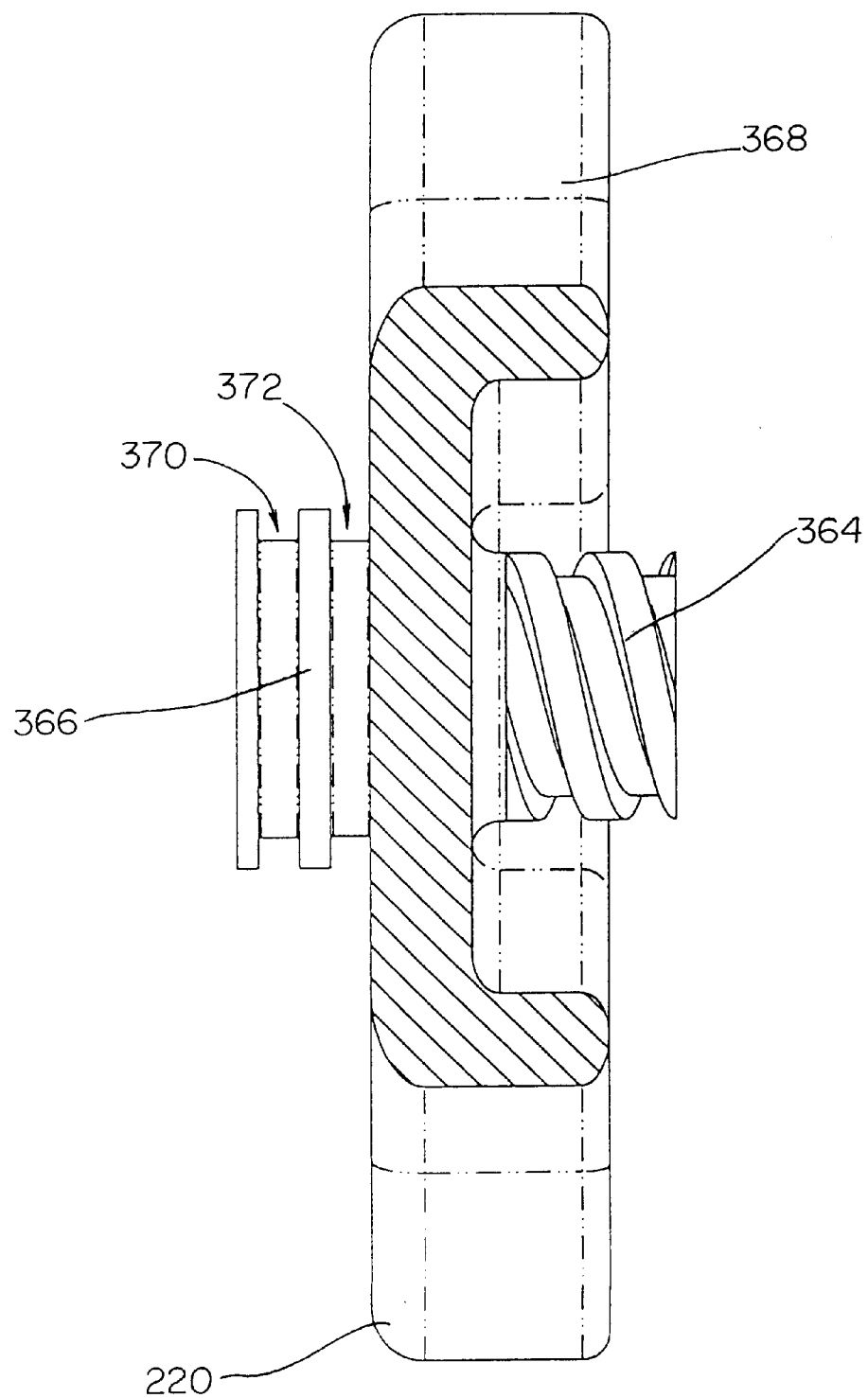
FIG. 13B is a partial cross sectional view of the coupling arm of the second embodiment of the precleaner header of the present invention showing the dialyzer connection.

The coupling arm 220, as shown in FIGS. 13, 13A, and 13B, is designed to releasably connect a dialyzer 98 to the precleaner header 210. The coupling arm 220 has a dialyzer neck 364, an insertion neck 366, and a handgrip 368. The dialyzer neck 364 and insertion neck 366 generally form a hollow cylinder with the handgrip 368 generally forming a ring circumscribing the middle of the cylinder. The insertion neck 366 is sized to be received in the needle assembly receiving channel 224. The insertion neck 366 has two generally parallel grooves 370, 372 defined about the outside circumference of the insertion neck 366. The distal groove 370 is sized for receiving the fourth O-ring 320. The proximal groove 372 is sized for receiving the bracket 258.

The dialyzer neck 364 is sized to connect to a dialyzer header cap 12. The dialyzer neck 364 has an inside 374 and an outside 376. The outside 376 is threaded to mate with the outer luer flange 56 of the dialyzer header cap 12 and the inside 374 is tapered to receive the inner luer flange 50 of the dialyzer header cap 12.

The handgrip 368 is a wheel-like grip designed to be rotated by hand. The handgrip 368 is integrally molded with the insertion neck 366 and the dialyzer neck 364. The handgrip 368 provides a gripping point for easy rotation of the coupling arm 220 to threadably attach the coupling arm 220 to the dialyzer header cap 12. The handgrip 368 also provides a gripping point for rotating and aligning the coupling arm 220 and attached dialyzer 98 in relation to the precleaner header 210.

Fourth O-ring

The fourth O-ring 320, as shown in FIGS. 8 and 9, is sized to be received in the distal groove 370 of the insertion neck 366. The fourth O-ring provides a fluid seal between the coupling arm 220 and the header spacer 322.

Header Spacer

Figure 14:
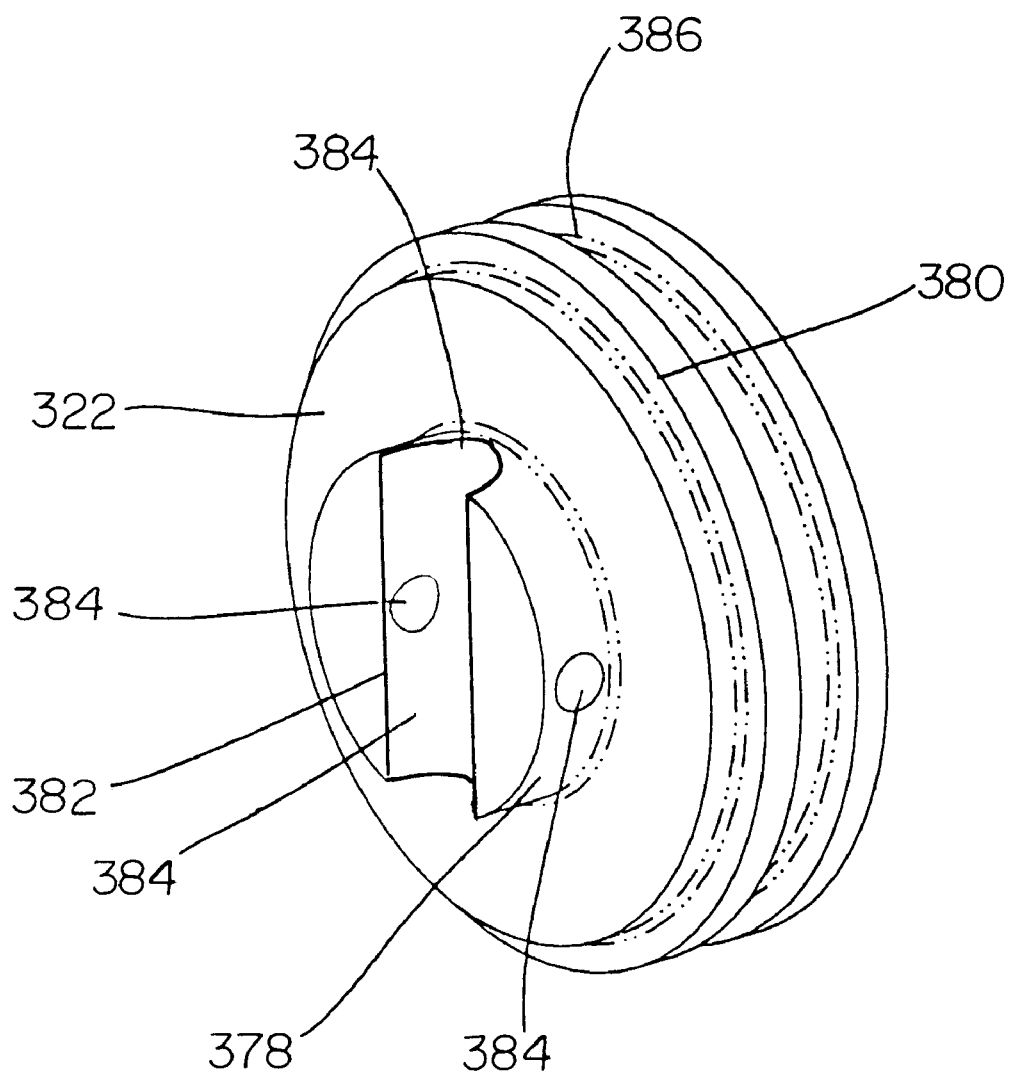
FIG. 14 is a perspective view of the header spacer of the second embodiment of the precleaner header of the present invention.
Figure 14A:
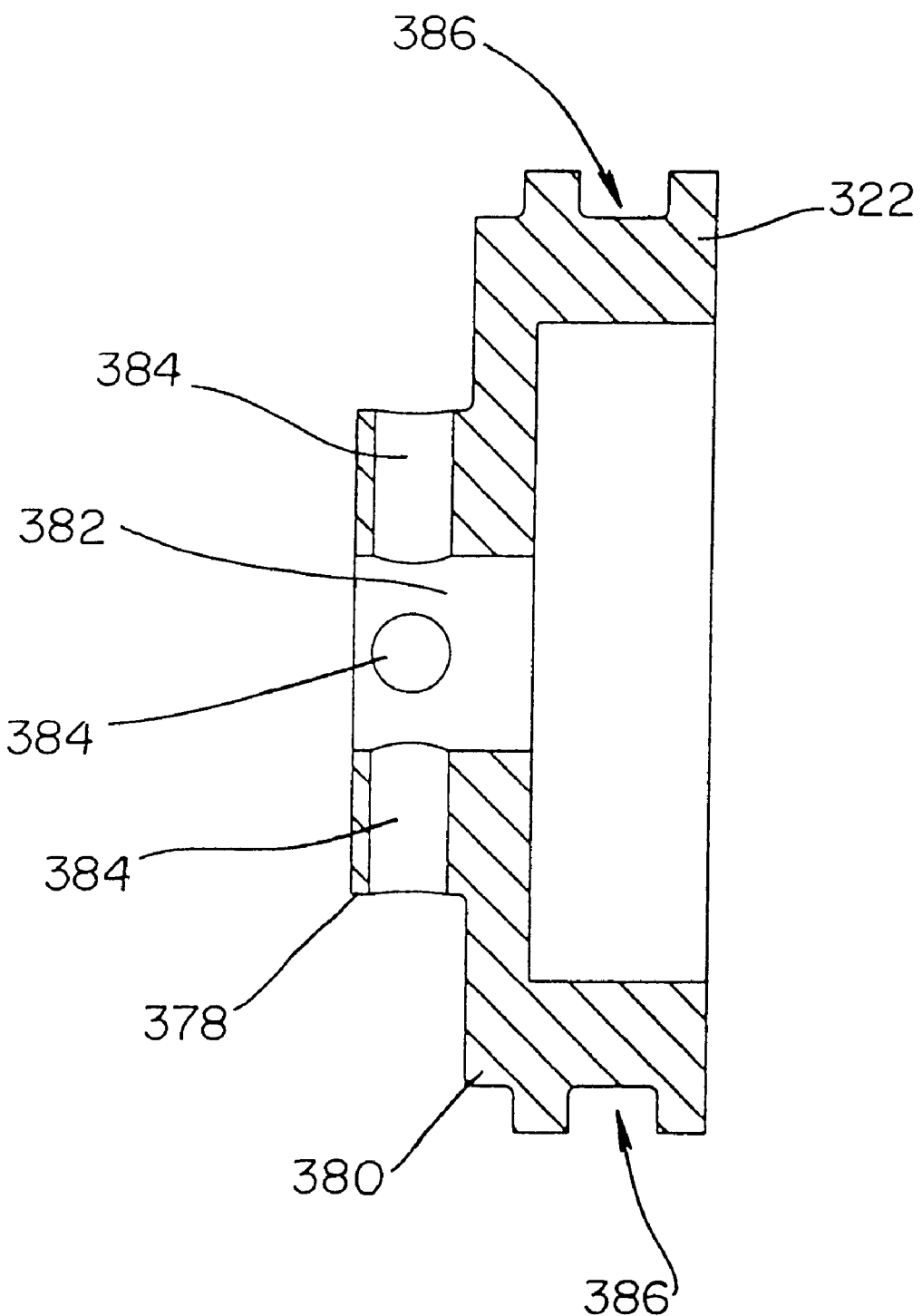
FIG. 14A is a cross sectional view of the header spacer of the second embodiment of the precleaner header of the present invention.

The header spacer 322, as shown in FIGS. 14 and 14A, is generally a hollow cylinder with a narrow section 378 and a wide section 380 with a needle channel 382 and one or more cross channels 384. The needle channel 382 is a generally cylindrical bore of varying diameter through the center of the header spacer 322. The header spacer 322 also defines a cross channel 384 that pass through the center of the narrow section 378 of the header spacer 322 perpendicular to the longitudinal axis of the cylinder. The cross channel 384 fluidly connects the needle channel 382 to the waste discharge channel 226. The cross channel 384 may be a cylindrical bore or preferably, a U-shaped groove. The header spacer 322 provides a pathway for the waste stream 104 to pass from the dialyzer 98 to the waste discharge channel 226. The needle channel 382 at the wide section 380 of the header spacer 322 is sized to receive the coupling arm 220. The fourth O-ring 320 provides a fluid tight seal between the coupling arm 220 and the header spacer 322. The coupling arm 220 and the header spacer 322 may be formed as one integral piece, eliminating the need for the fourth O-ring 320. However, a separate header spacer 322 allows the cross channel 384 in the header spacer 322 to be aligned with the waste discharge channel 226 without affecting the orientation of the dialyzer 98 and the coupling arm 220 to the precleaner header 210. The wide section 380 of the header spacer 322 is sized to be received in the needle assembly receiving channel 224. The header spacer 322 defines a groove 386 circumscribing the outside of the wide section 380 of the header spacer 322 for receiving the fifth O-ring 324. The fifth O-ring 324 provides a fluid tight seal between the header spacer 322 and the housing 214.

Fifth O-ring

The fifth O-ring 324, as shown in FIGS. 8 and 9, is sized to be received in the groove 386 defined circumscribing the wide section 380 of the header spacer 322. The fifth O-ring 324 provides a fluid seal between the header spacer 322 and the housing 214.

Bracket

Figure 7:
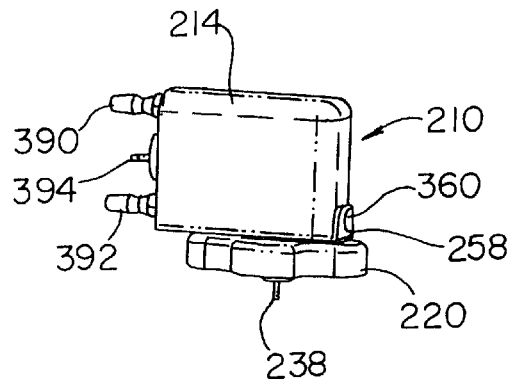
FIG. 7 is a perspective view of a second embodiment of the precleaner header of the present invention.

The bracket 258 as shown in FIGS. 7–9, is attached to the housing 214 by inserting a bracket screw 360 through a screw hole in the bracket 258 and into bracket screw hole 356. The bracket 258 is preferably a stainless steel plate bent into an L-shape. The bracket 258 has a screw hole near one end and a C-shaped opening near the other end. The C-shaped opening is sized to receive the proximal groove 372 of the insertion neck 366 of the coupling arm 220. The bracket 258 is attached to the housing 214 by the bracket screw 360. The C-shaped end retains the coupling arm 220 in the needle assembly receiving channel 214.

Base Unit

Figure 18:
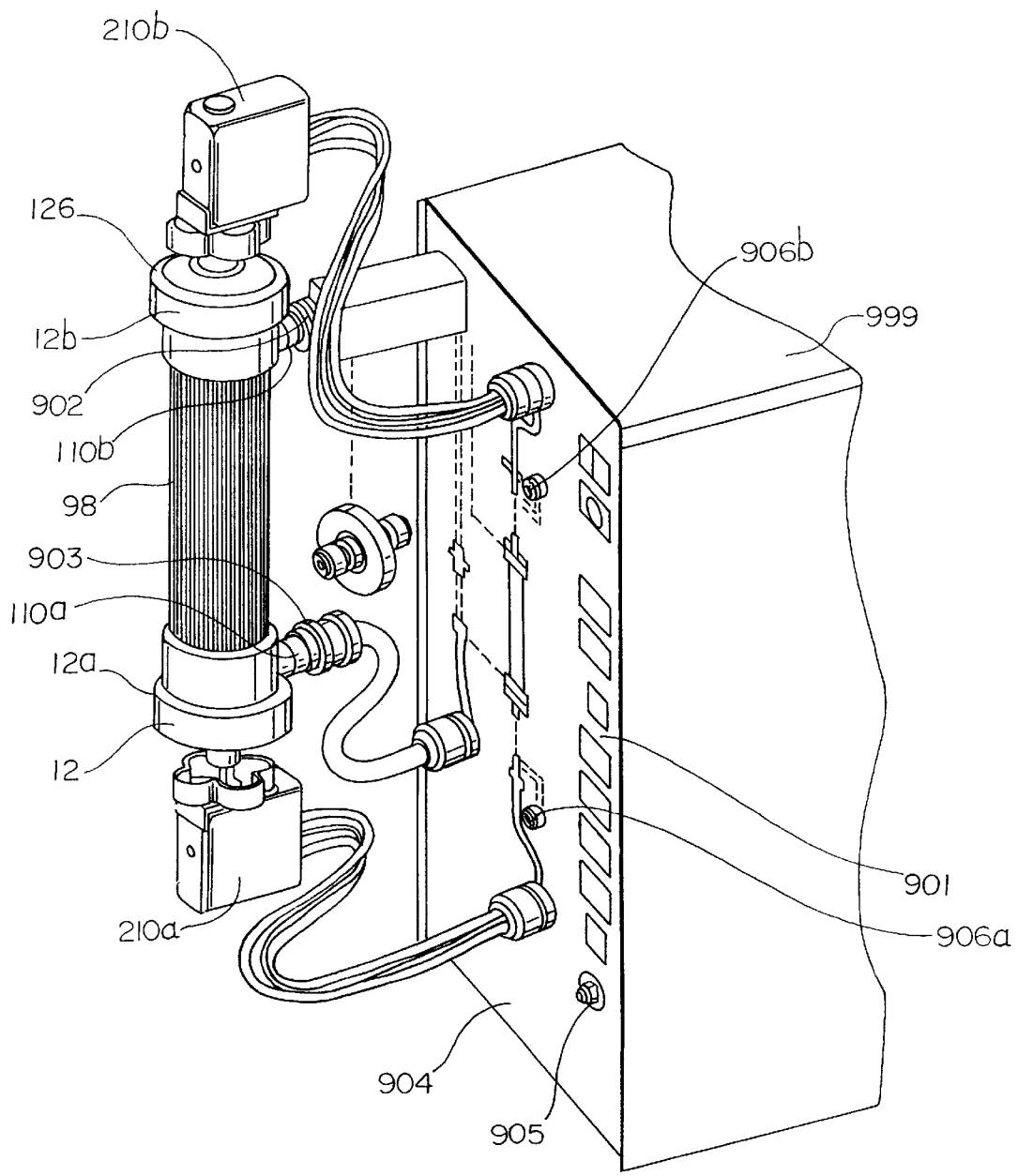
FIG. 18 is a perspective view of the front of the base unit of the present invention connected to a dialyzer.
Figure 19:
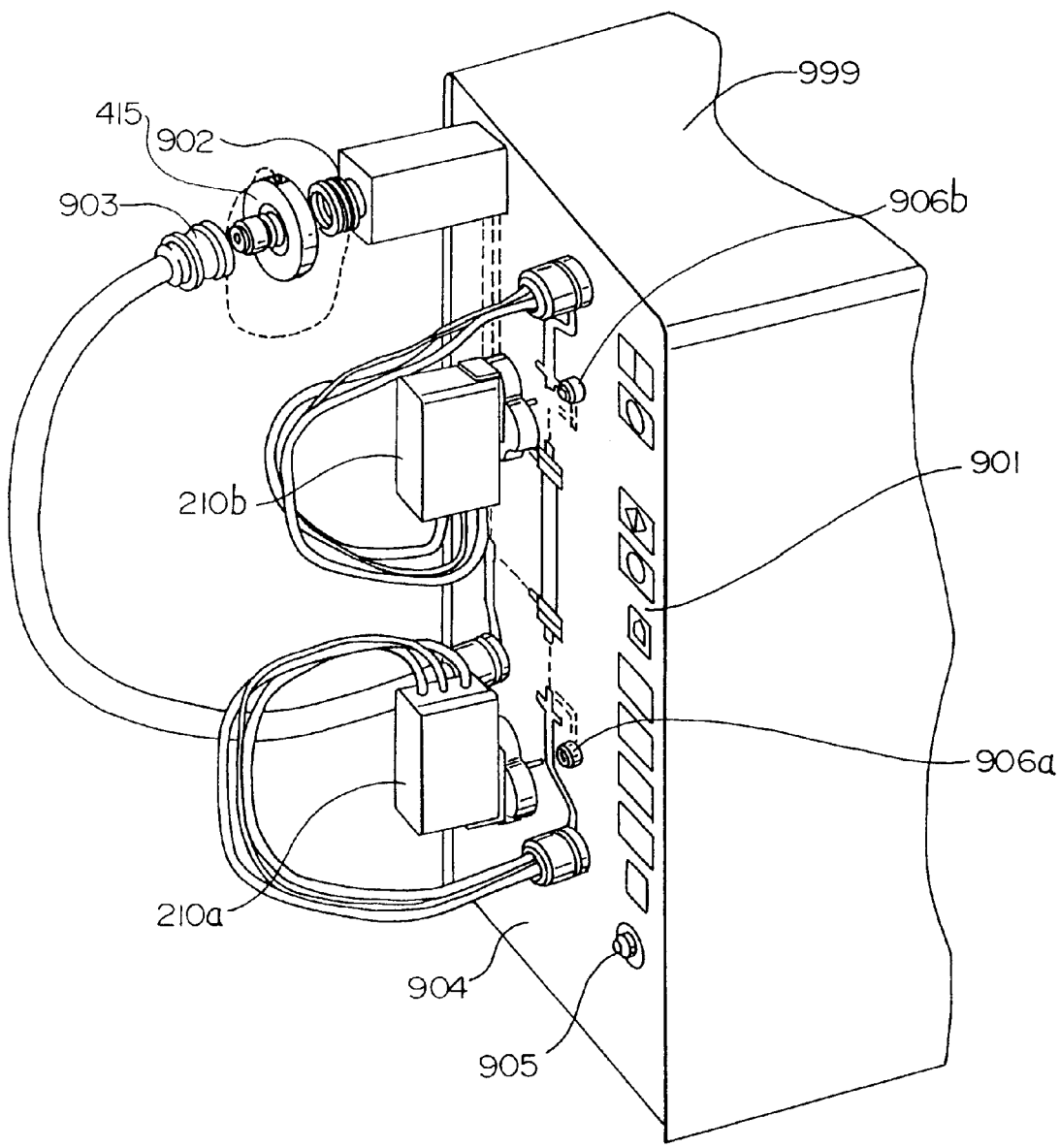
FIG. 19 is a perspective view of the front of the base unit of the present invention without a dialyzer.

The base unit 999, as shown in FIGS. 18 to 38, provides automation of the fluid flows to clean the used dialyzer 98. FIGS. 18 and 19 show the front 904 of the base unit 999 including a pair of precleaner headers 210. The front 904 of the base unit 999 includes a control panel 901, an arterial dialysate port connection 903, and a venous dialysate port connection 902. The front 904 of the base unit 999 also includes a cleaner attachment port 905 and precleaner header needle ports 906. The cleaner attachment port 905 is for attachment of a cleaning fluid attachment line 907 during cleaning of the base unit 999. The precleaner header needle ports 906 are for placement of the precleaning headers 210 when the device is not attached to a dialyzer 98.

Figure 20:
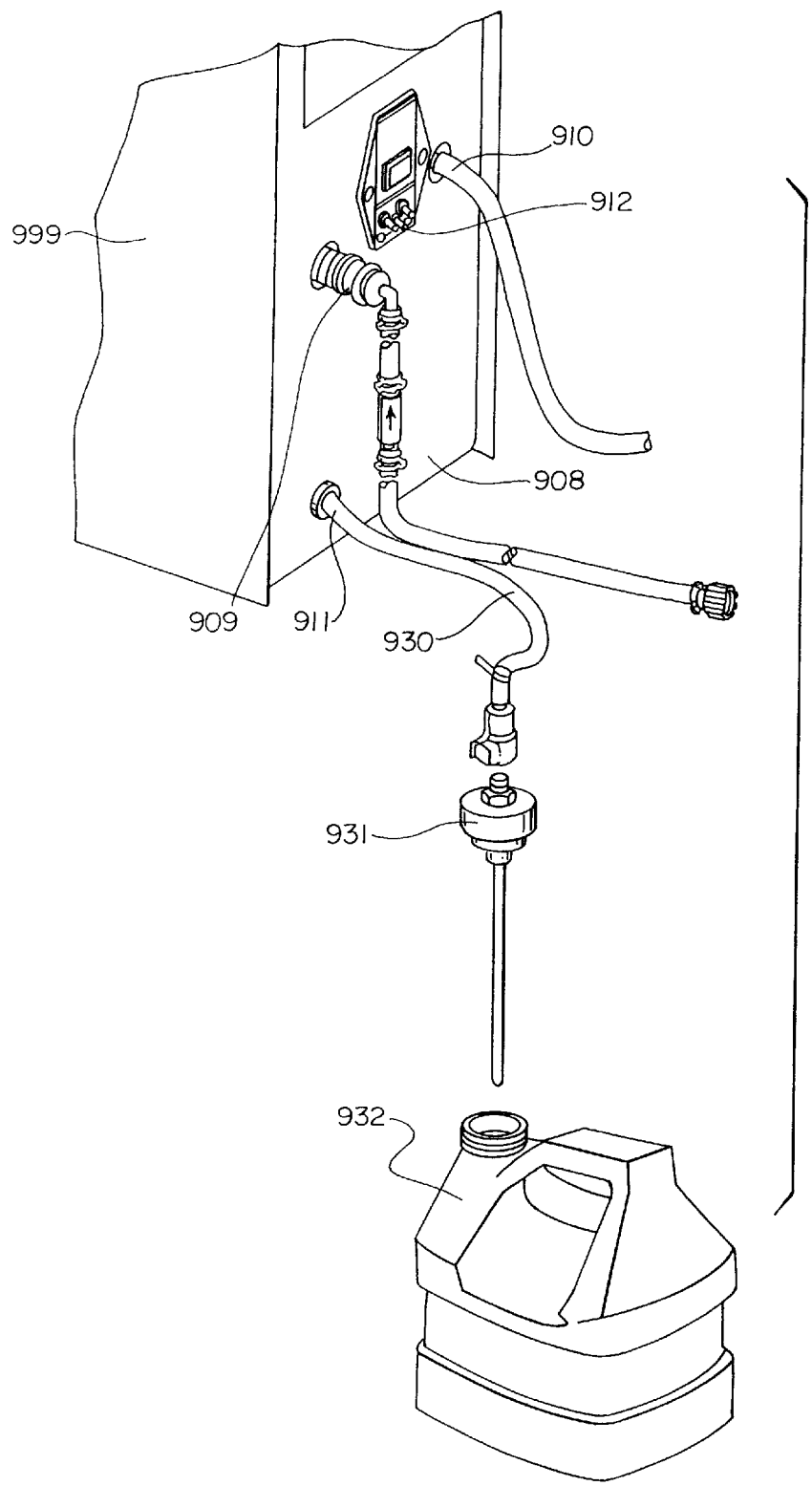
FIG. 20 is a perspective view of the back of the base unit of the present invention.

As shown in FIG. 20, the back 908 of the base unit 999 includes a water inlet port 909, a waste outlet port 910, a chemical port 911, and a electrical power connection 912. FIG. 20 also shows a chemical uptake line 930, a chemical cap 931, a bottle of chemical 932. The chemical is preferably Renaclear™ disinfectant.

Figure 21:
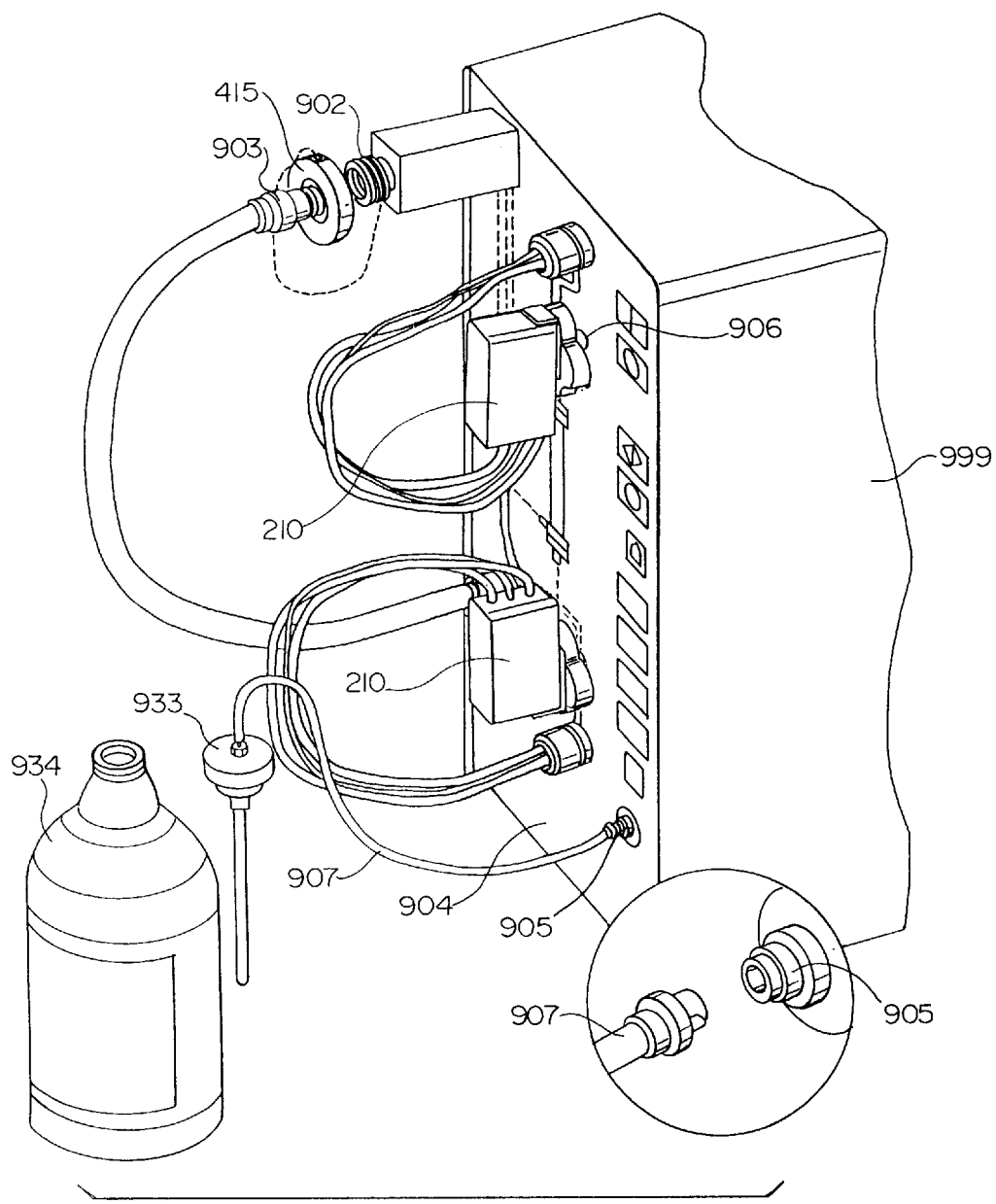
FIG. 21 is a perspective view of the front of the present invention in a storage or cleaning position.

As shown in FIG. 21, the front 904 of the base unit 999 includes a cleaner attachment port 905 and a cleaning fluid attachment line 907. The cleaning fluid attachment line 907 includes a cleaning fluid cap 933 that attaches to the cleaning fluid 934. The cleaning fluid 934 is preferably "for industrial use" Formula 409® cleaner.

Figure 23:
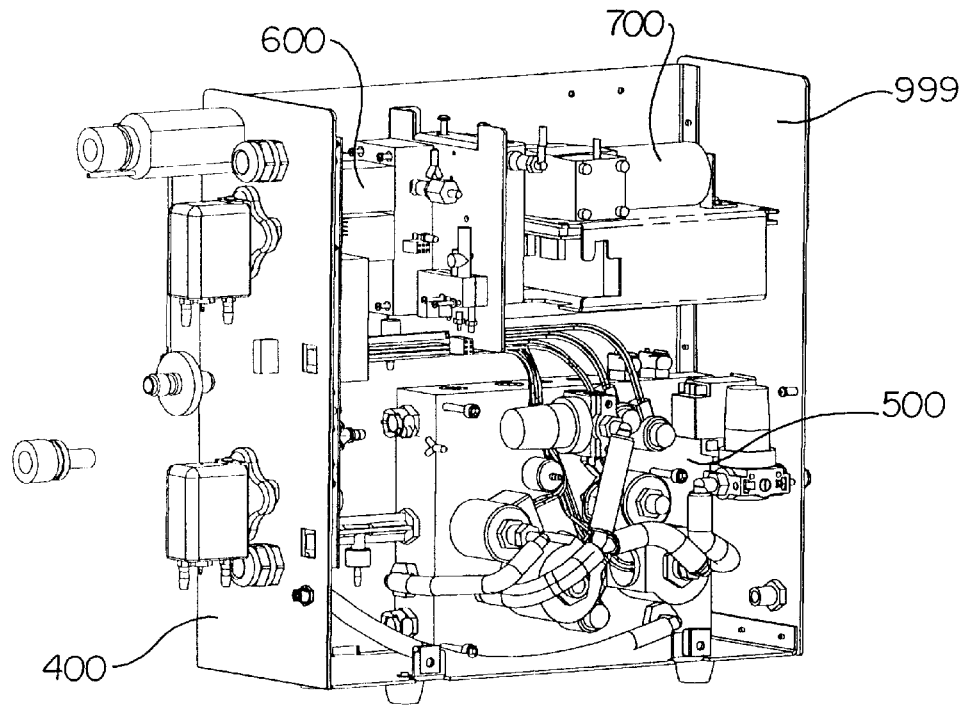
FIG. 23 is a perspective view of the base unit of the present invention without the cover and some connecting tubing showing the inside of the side and back of the base unit.
Figure 24:
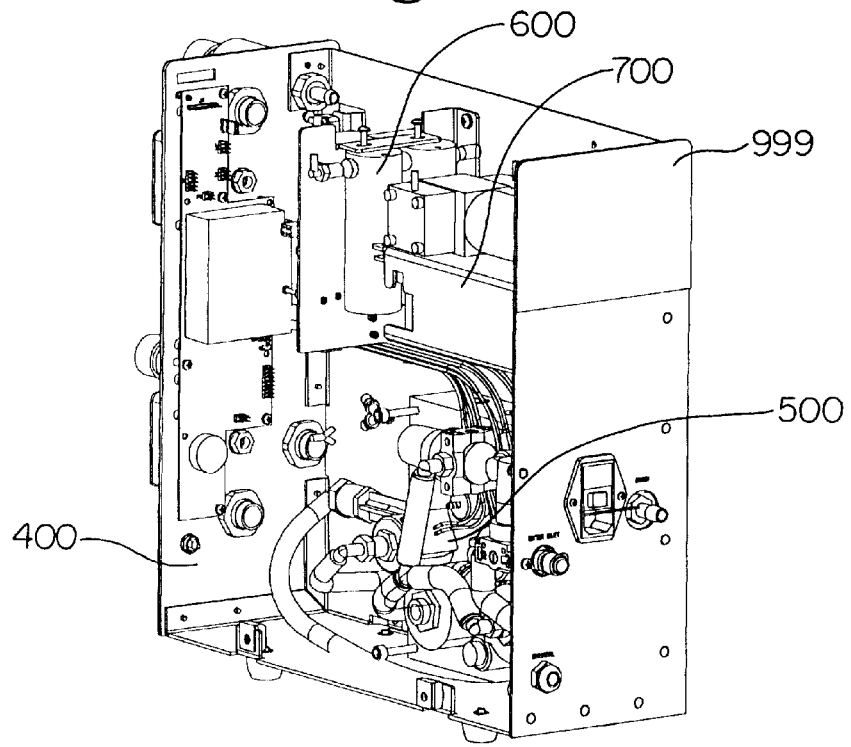
FIG. 24 is a perspective view of the base unit of the present invention without the cover and some connecting tubing showing the inside of the side and front of the base unit.
Figure 25:
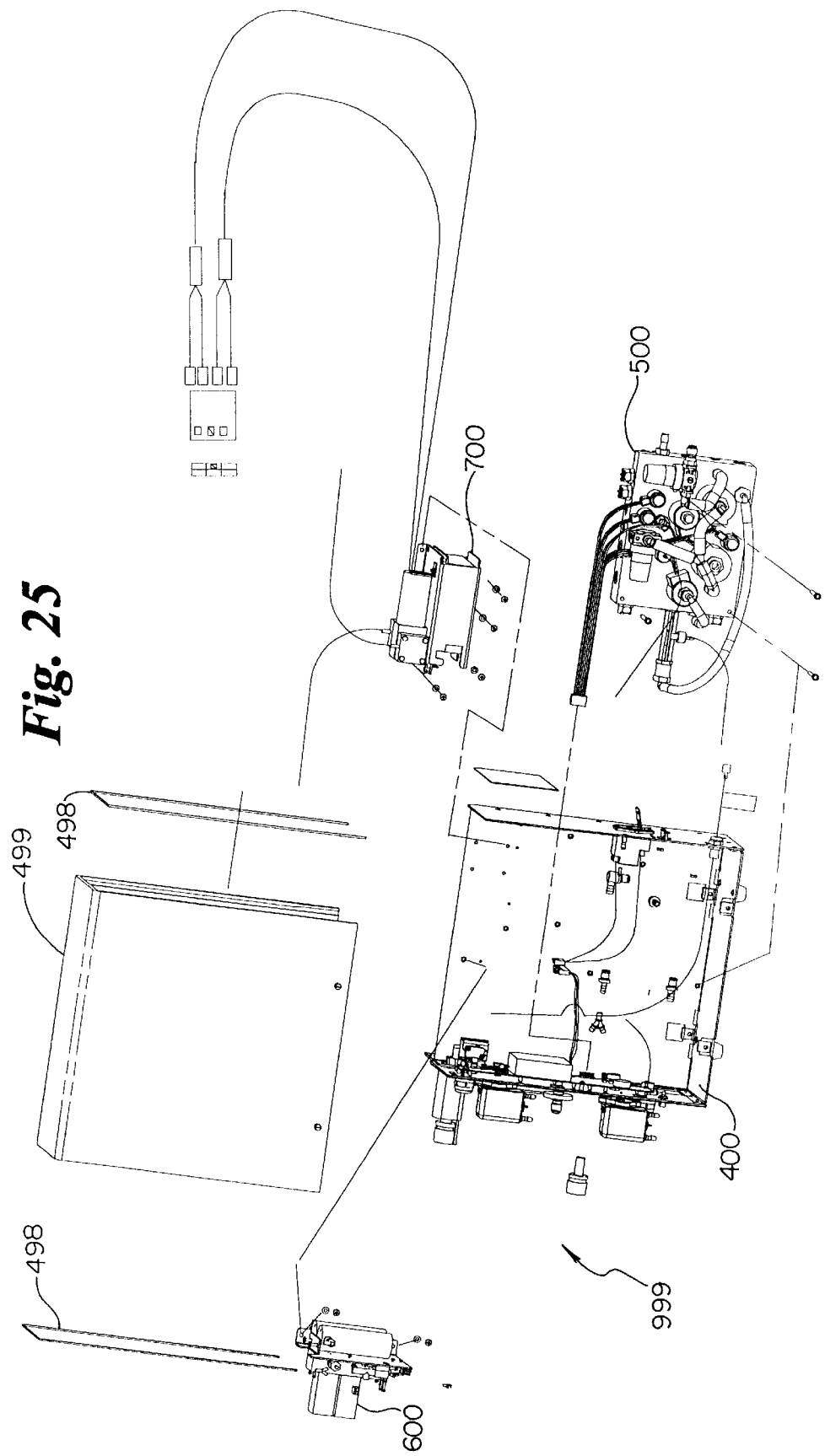
FIG. 25 is a perspective exploded view of the base unit of the present invention.

As shown in FIGS. 23, 24, and 25, the base unit 999 includes a chassis assembly 400, a cover 499, cover rails 498, a manifold assembly 500, a compressor assembly 700, a chemical uptake/air filter assembly 600, and various connecting tubes and wires (some not shown for clarity).

Chassis Assembly

The chassis assembly 400 as shown in FIGS. 26–31, includes a rectangular metal box 401 with various attachments. The box 401 has a front panel 461, a side panel 462, a back panel 463 and a bottom panel 464. A front mask switch 402 is attached to the outside of the front panel 461 of the box 401. Various other fittings and attachments are attached to and through the front panel 461 of the box 401 including a cleaning port fitting 403, two interlock panel fittings 404 held in place with two washers 405 and two hex nuts 406, three bushings 407 including three strain relief collars 408, and a dialyzer holder assembly 490. The dialyzer holder assembly 490 includes an interlock rod 409 a dowel pin 410, a dialyzer holder post 411, a dialyzer connector 412, a post nut 413, a holder post screw 414, a male/male adapter or shunt 415, two post clamp screws 416, an end coupling chain 418, an end coupling screw 419, and a post clamp 420.

As shown in FIGS. 26, 27, 28, and 30, an interlock switch assembly 480 is attached on the inside of the top left side of the side panel 462 of the box 401. The interlock switch assembly includes a switch 421, held in place with two screws 423 and two washers 422, a cable conductor 424, a housing 425, a receipt 426, and heat shrink tubing 427.

As shown in FIGS. 26, 27, 28, and 31, a plug assembly 470 is attached to the middle of the inside of the back panel 463 of the box 401 and includes two fuses 431 and a socket power entry module 429 held in place with two screws 430.

Figure 26:
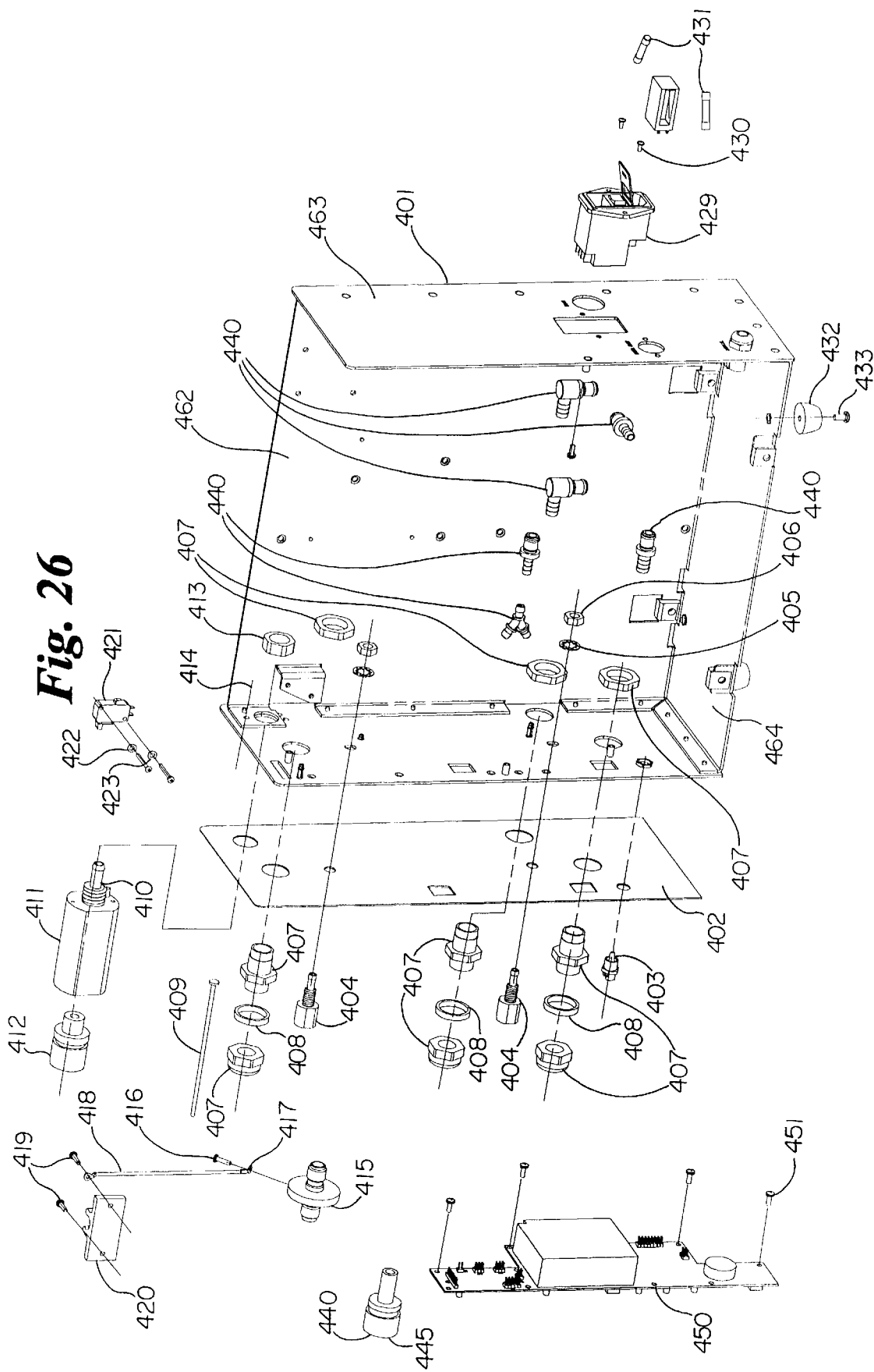
FIG. 26 is a perspective exploded view of the chassis assembly of the base unit of the present invention.
Figure 28:
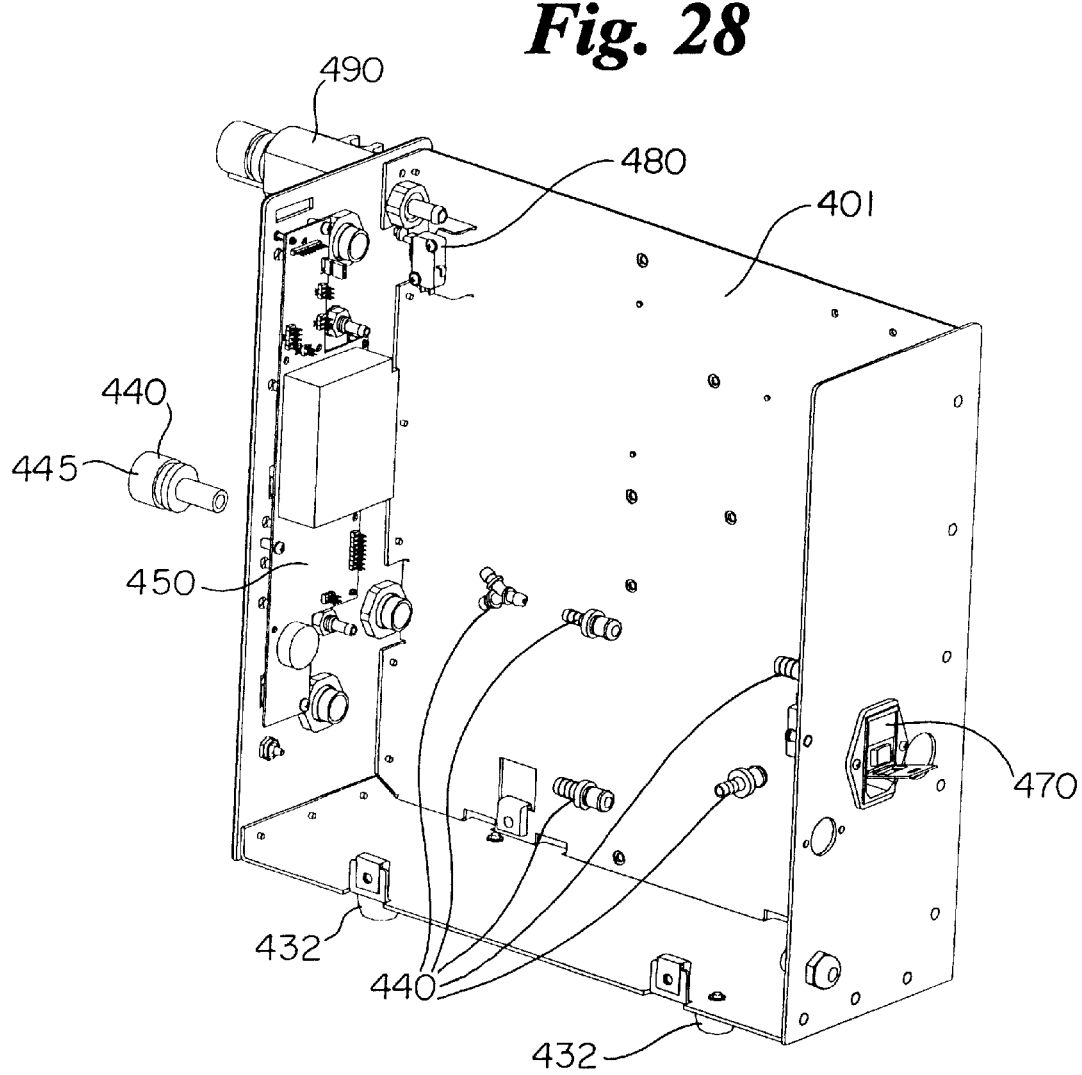
FIG. 28 is a perspective view of the inside of the side and front of the chassis assembly of the base unit of present invention.

As shown in FIGS. 26 and 28, four rubber feet 432 are attached to the outside of the bottom panel 464 of the box 401 with four screws 433.

Figure 27:
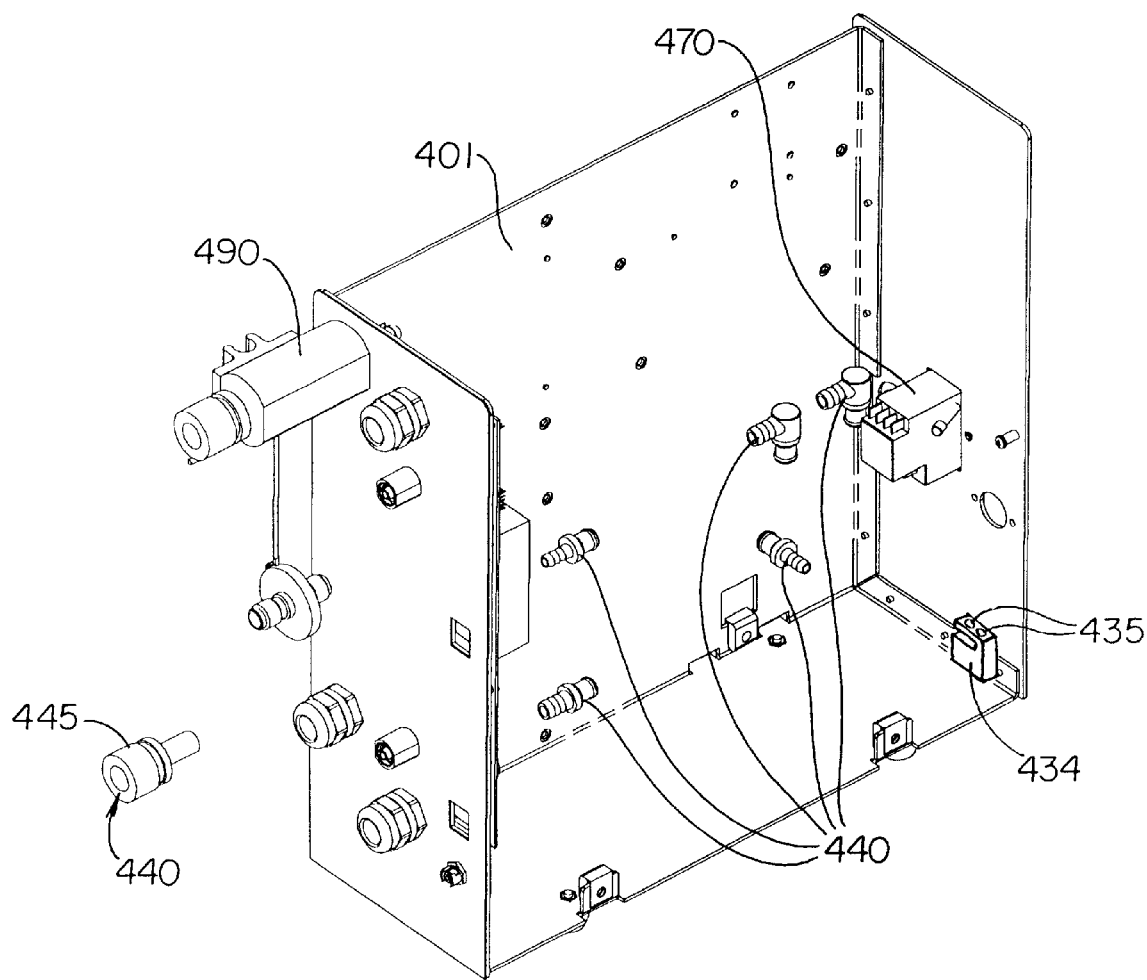
FIG. 27 is a perspective view of the chassis assembly showing the inside of the side and back of the chassis assembly of the base unit of the present invention.

As shown in FIG. 27, an uptake hose strain relief 434 is attached to the bottom of the inside of the back panel 463 of the box 401 with two screws 435.

Figure 29:
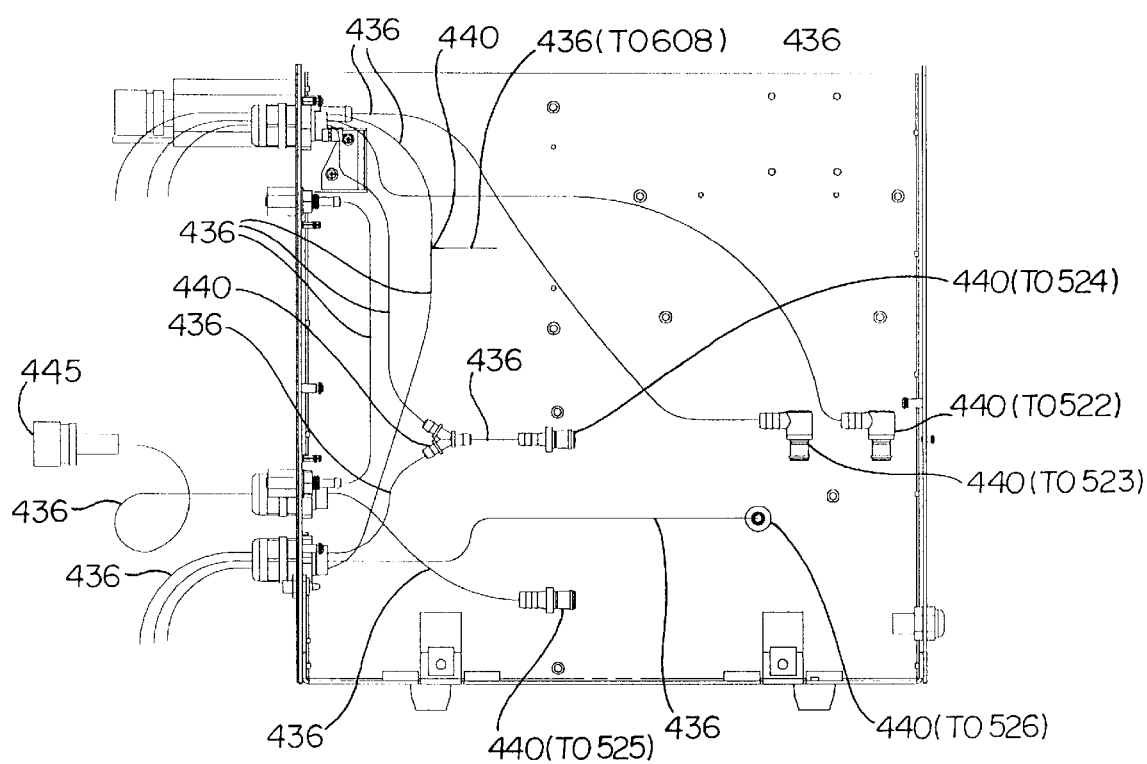
FIG. 29 is a tubing diagram of the base unit of the present invention.
Figure 30:
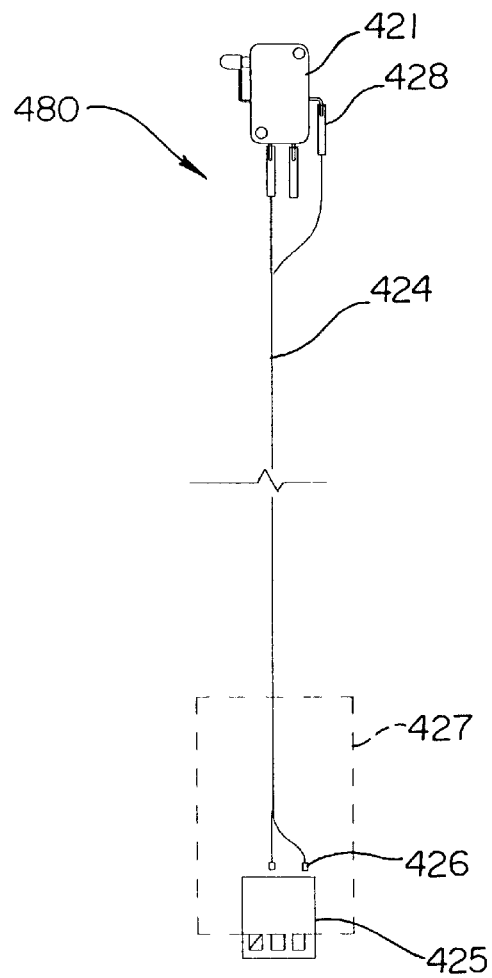
FIG. 30 is a side view of the interlock switch assembly of the chassis assembly of the base unit of the present invention.
Figure 31:
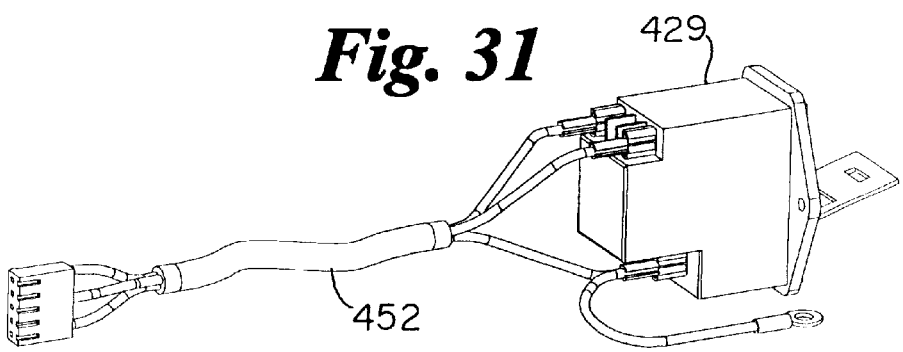
FIG. 31 is a perspective view of the plug assembly of the chassis assembly of the base unit of the present invention.

Various tubing 436 and connectors 440 are used including 1/16 inch PVC tubing, 1/4 inch PVC tubing, 3/16 inch PVC tubing, 3/8 inch PVC tubing, a 3/16 Y barb, a 3/8 Barb X Colder Coupler L, a 1/4 Barb X Colder Coupler L, two 1/4 Barb X Colder couplers, a 3/8 Barb X Colder Coupler, a dialyzer connector Barb type, and a 1/16 Barb T. Dialyzer connector 445 is attached via tubing as shown in FIG. 29.

As shown in FIGS. 26 and 28, attached to the inside front of the box 401 is a front panel circuit board 450 held in place with five screws 451. Internal power is supplied from the plug assembly 470 through internal power cable 452 to the power supply 702.

Chemical Uptake/Air Filter Assembly

Figure 32:
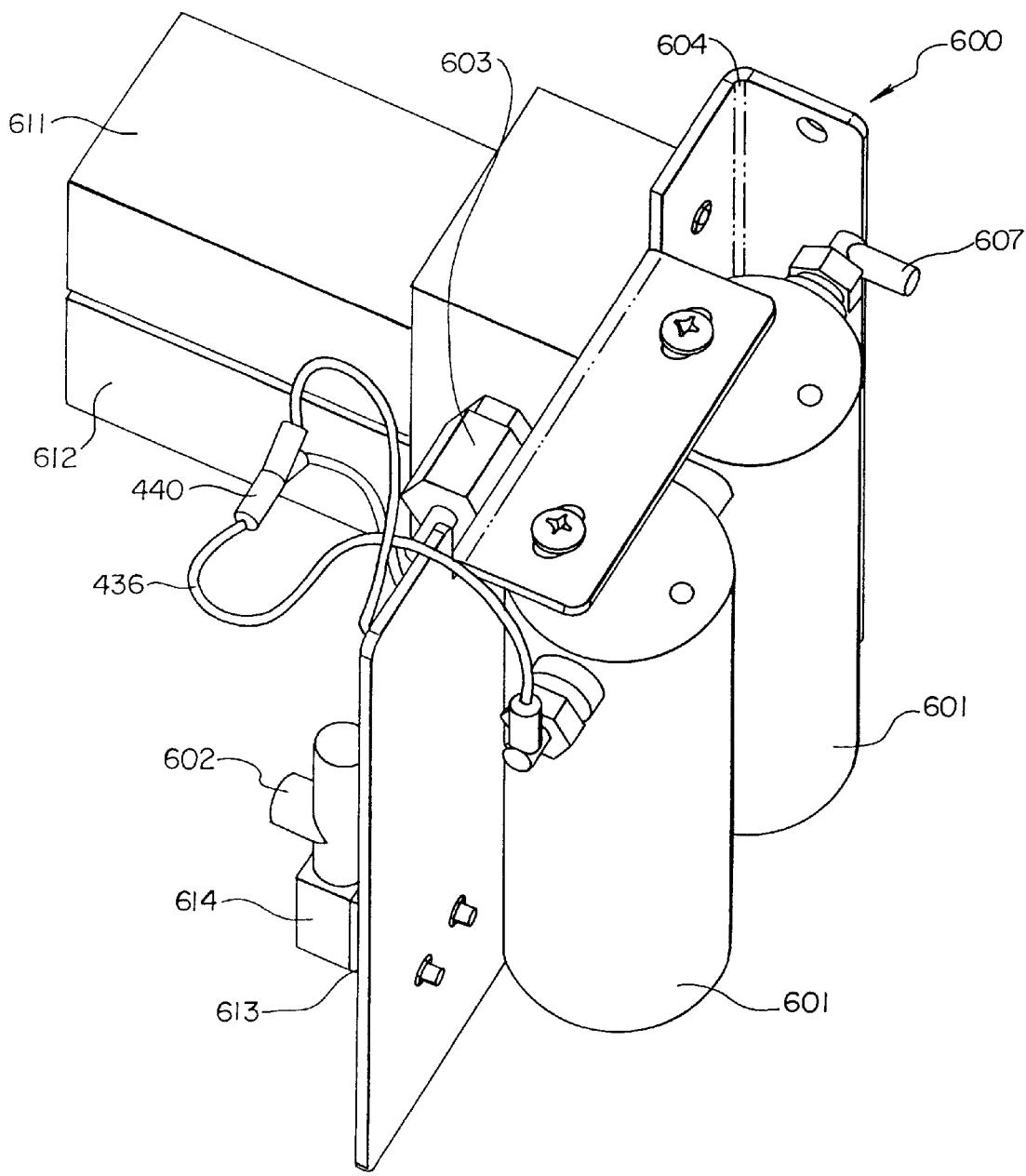
FIG. 32 is a top perspective view of the chemical uptake/air filter assembly of the base unit of the present invention.
Figure 33:
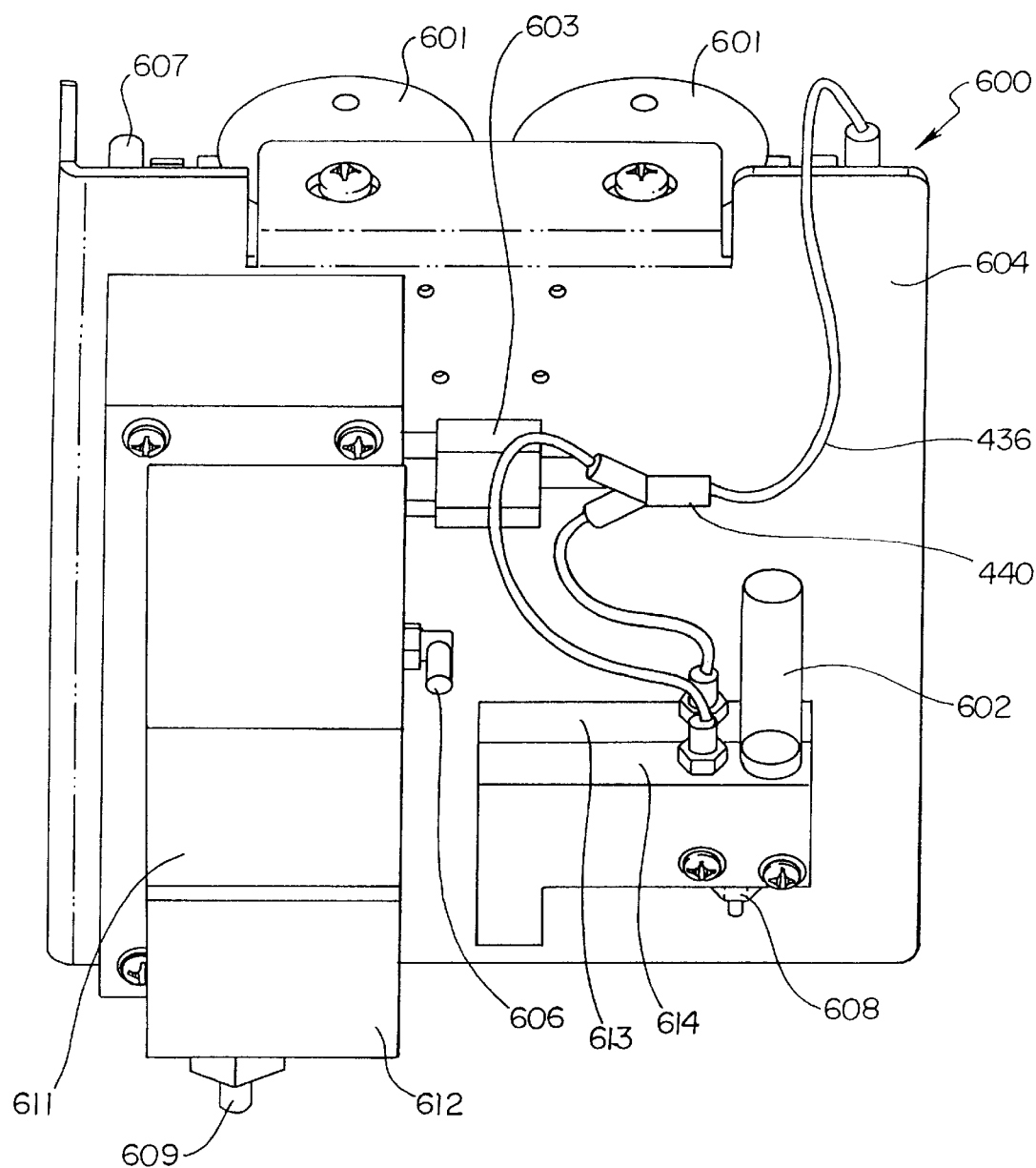
FIG. 33 is a side perspective view of the chemical uptake/air filter assembly of the base unit of the present invention.
Figure 33A:
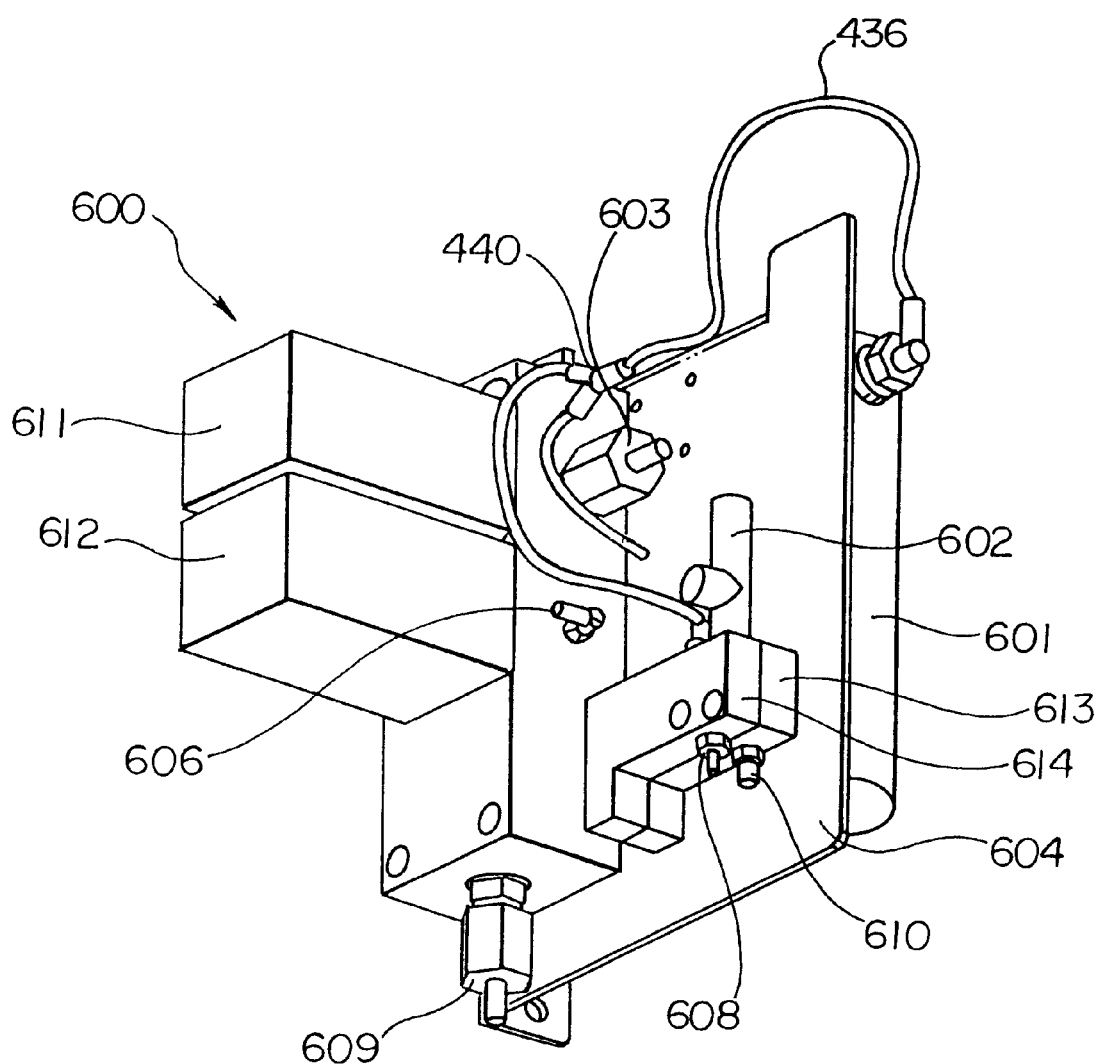
FIG. 33A is a bottom perspective view of the chemical uptake/air filter assembly of the base unit of the present invention.
Figure 35:
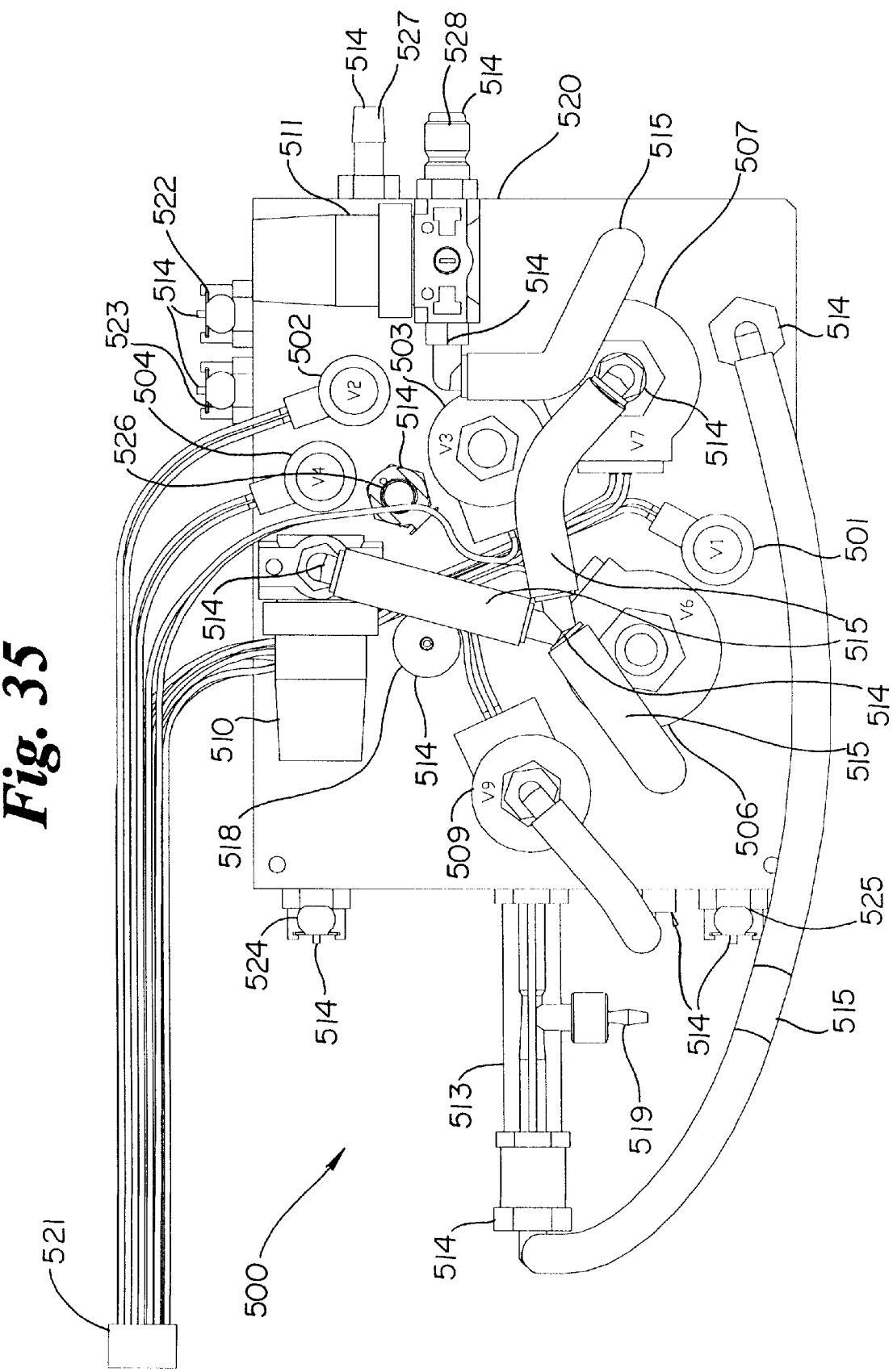
FIG. 35 is a side view of the manifold assembly of the base unit of the present invention.

As shown in FIGS. 23–25, the chemical uptake/air filter assembly 600 is attached to upper left corner of the side panel 462 of the box 401. As shown in FIGS. 32, 33, and 33A, the chemical uptake/air filter assembly 600 includes two air filters 601, a needle valve 602, a chemical uptake connection 603, a bracket 604, and attachment screws (not shown), a cleaner uptake connection 606, a compressor connection 607, a header connection 608, a venturi connection 609, a manifold connection 610, fluid (V10) valve 611, fluid (V5) valve 612, air (V8) valve 613, and air (V11) valve 614. The air (V11) valve 614 takes air from the compressor 703 through the air filters 601 and delivers a pulsating air stream to the precleaner headers 210 to drive the rotator assembly 219. Air (V11) valve 614 is opened to pressurize the tubing and depress the piston 350 of the rotator assembly. The needle valve 602 works with air (V11) valve 614 to bleed off air pressure, in turn, releasing the piston 350 and, therefore, rotating the needle 238. The air (V11) valve 614 is preferably a Mac 111B-501BAAA valve. The header connection 608 is attached to the outlet of air (V11) valve 614 and is connected to each precleaner header 210 by tubing. The air (V8) valve 613 also receives air via the filters 601 from the compressor 703. Air (V8) valve 613 is preferably a Mac 111B-501BAAA valve. As shown in FIG. 33A, manifold connection 610 is connected to the bottom of air (V8) valve 613 and is connected to the manifold assembly 500 to manifold air inlet 518 as shown in FIG. 35. Chemical 932 is received via tubing through chemical port 911 (FIG. 20), and is attached to chemical uptake connection 603, which is attached to fluid (V10) valve 611. Cleaning fluid 934 is received via tubing through cleaner attachment port 905 (FIG. 21), and is attached to fluid (V5) valve 612. Fluid from valves 611 and 612 is discharged through venturi connection 609. Tubing connects venturi connection 609 to the fluid uptake 519 of the venturi 513 of the manifold assembly 500 (FIG. 35). Fluid valves 611 and 612 are preferably Allied 4280-06-8243 valves.

Compressor Assembly

Figure 34:
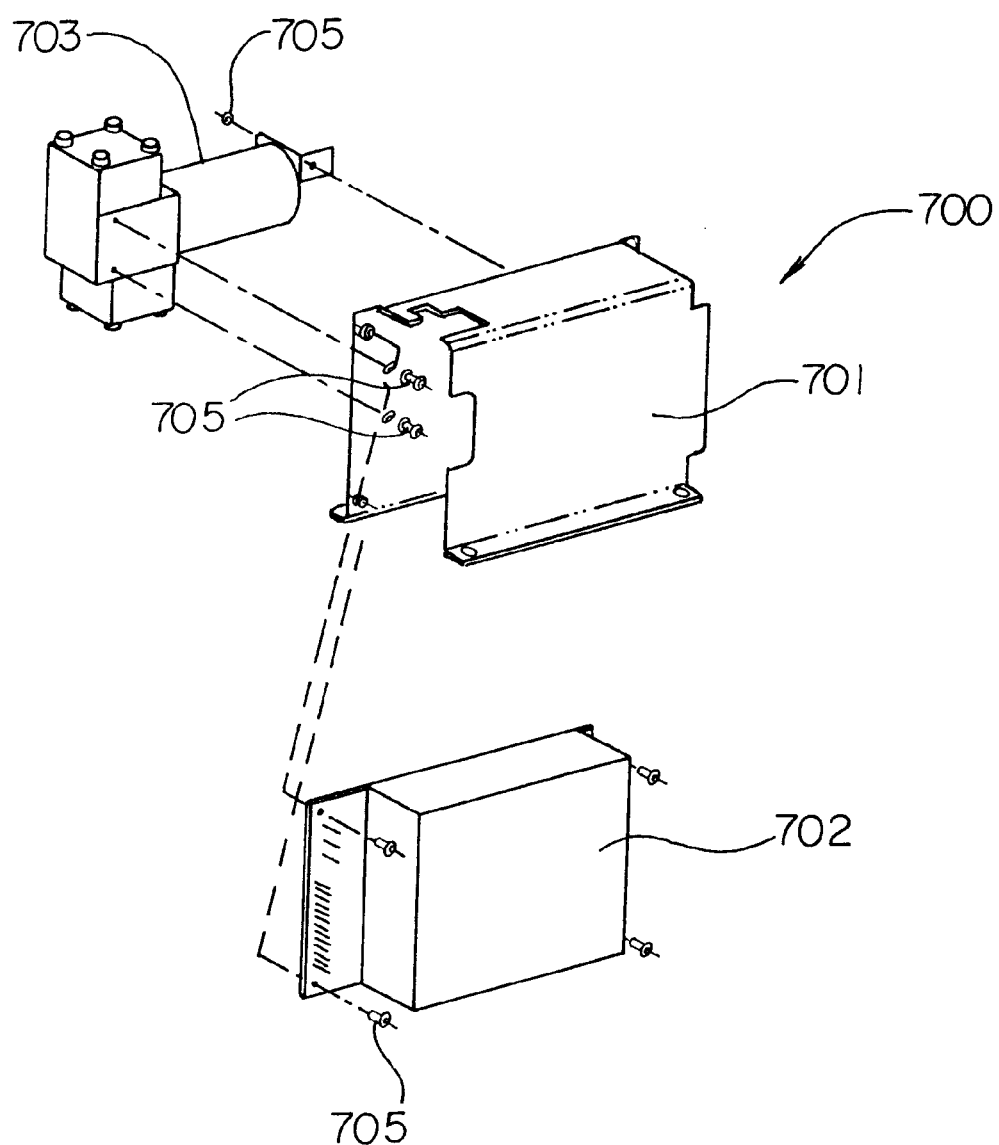
FIG. 34 is a exploded perspective view of the compressor assembly of the base unit of the present invention.

As shown in FIGS. 23–25, the compressor assembly 700 is attached to the upper right corner of the inside of side panel 462 of the box 401. As shown in FIG. 34, the compressor assembly 700 includes a bracket 701, a power supply 702, a compressor 703, and screw assemblies 705. The compressor 703 provides air via tubing to the air filters 601 of the chemical uptake/air filter assembly 600. The compressor 703 is preferably a Thomas 7011-0042 or a KNF 1030. The power supply is preferably a Power One MAP110-1024.

Manifold Assembly

Figure 36:
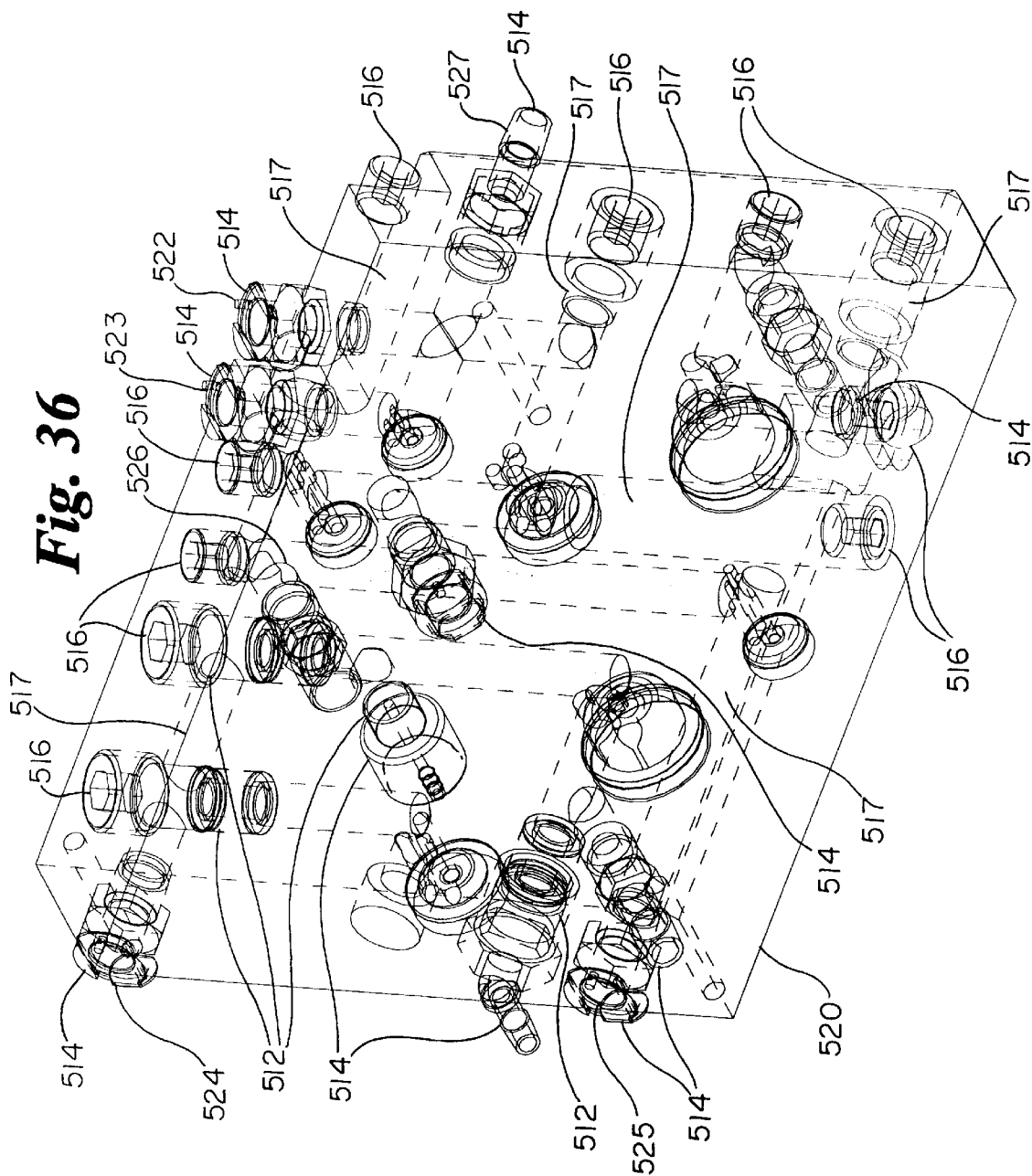
FIG. 36 is a perspective see through view of the manifold block and connectors of the manifold assembly of the base unit of the present invention.
Figure 37:
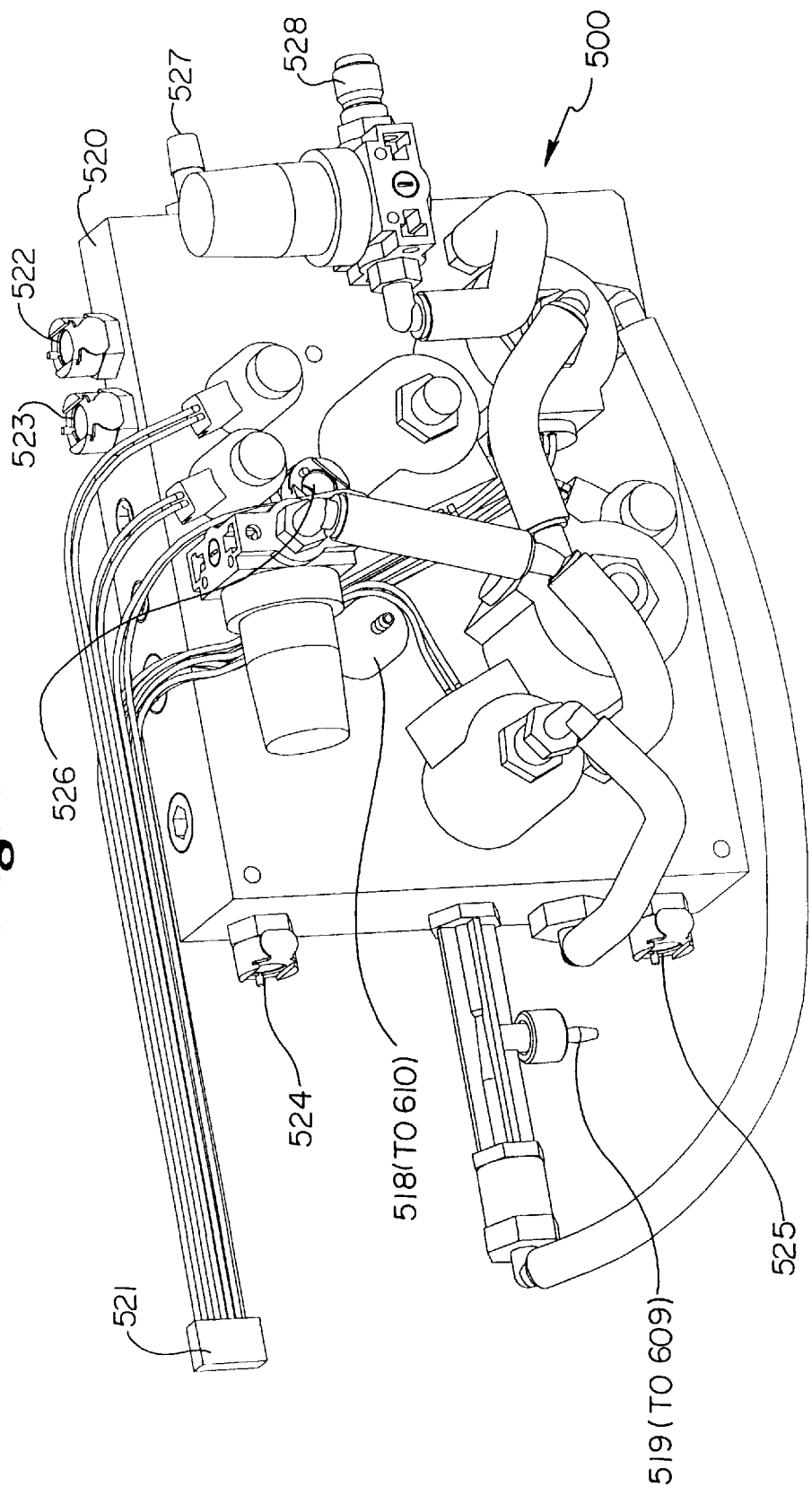
FIG. 37 is a perspective view of the manifold assembly of the base unit of the present invention.

As shown in FIGS. 23–25, the manifold assembly 500 is attached to the inside of the bottom center of the back panel 463 of the box 401. As shown in FIGS. 35–37, the manifold assembly 500 includes seven valves (501, 502, 503, 504, 506, 507, and 509), two regulators 510 and 511, check valves 512, a venturi 513, and various connectors 514, tubing 515, plugs 516, a manifold air inlet 518, a fluid uptake 519, an electrical connector 521 and a manifold block 520.

Figure 38:
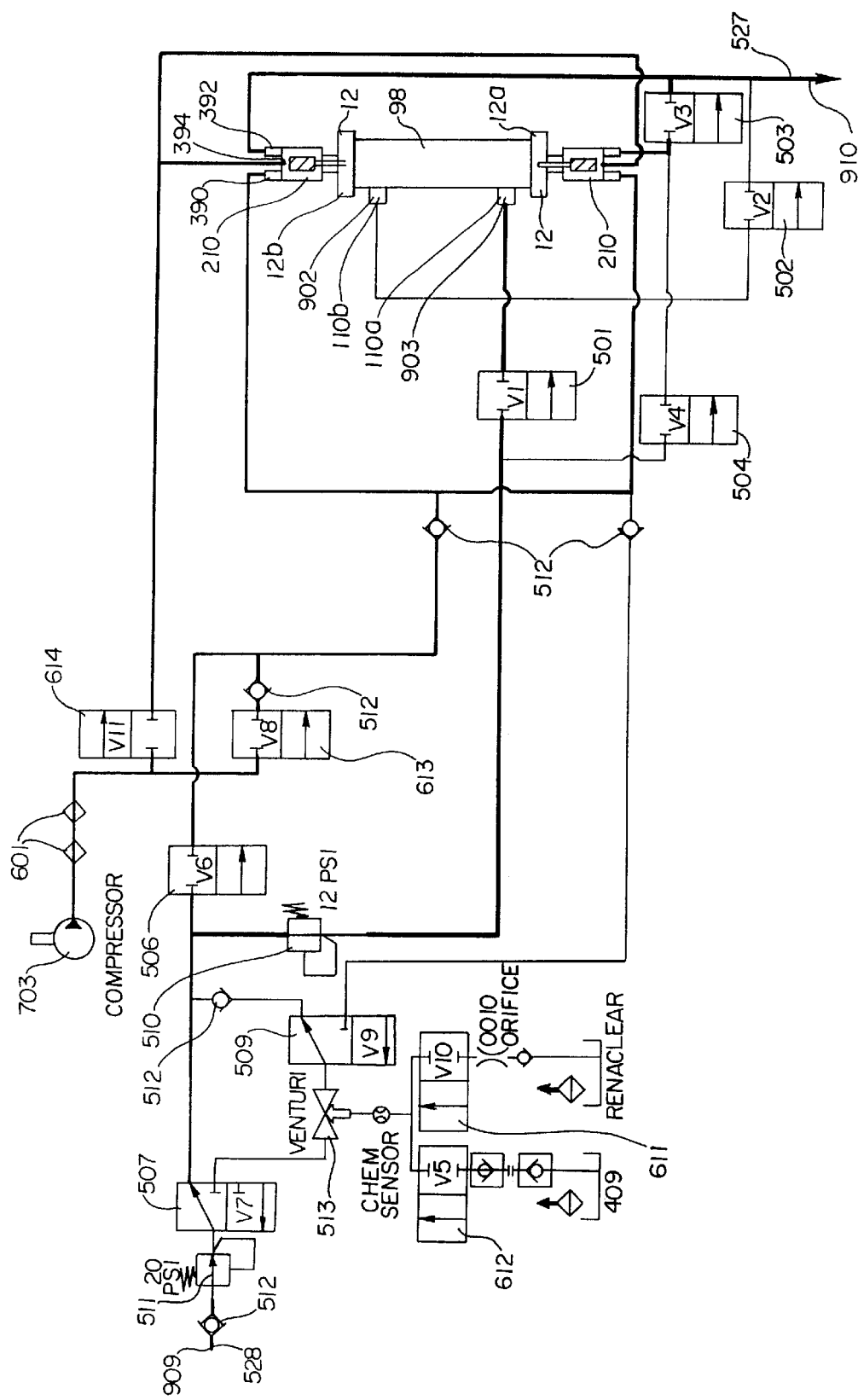
FIG. 38 is a schematic drawing of the air and liquid paths of the present invention.

Valve 501 is preferably an Allied 2W131-X31-L7D6 valve. Valve 502 is preferably an Allied 2W131-X31-L7D6 valve. Valve 503 is preferably an Allied 2823C-X05-LAF6 valve. Valve 504 is preferably an Allied 2W131-X32-L8E6 valve. Valve 506 is preferably an Allied 22231-X02-LCJ6 valve. Valve 507 is preferably an Allied 32251-X02-LCJ6 three-way valve. Valve 509 is preferably an Allied 3825C-X01-L9F6 three-way valve. Regulator 510 is preferably a Watts R25-02BK 0–50 psi regulator. Regulator 511 is preferably a watts R25-02AK 0–25 psi regulator. Check valve 512 is preferably Smart check valve models 150-PPA-1/2#-H or 312/302-PPA-1/2#-H. Venturi 513 is preferably a Mazzei injector model 283. The connectors 514 are preferably Colder couplers model PLCX100-04-12, Hansen fittings or various sized tubing connectors. The tubing 515 is preferably PVC tubing of 1/4, 3/16, or 1/16 inch inside diameter. The plugs 516 are sized to fit into the channels 517 formed in the manifold block 520. Channels 517 are defined in the manifold block 520 to fluidly connect the various valves and lines to each other as schematically shown in FIG. 38. As shown in FIGS. 29, 33A, and 37, manifold air inlet 518 attaches via tubing to manifold connection 610 (not shown on FIG. 29). Fluid uptake 519 of the venturi 513 is connected via tubing to venturi connection 609. Electrical connector 521 is attached to the panel circuit board 450. Upper header connector 522 is connected by tubing to the waste discharge connector 392 of the upper precleaner header 210. Venous dialyzer connector 523 is connected by tubing to the venous dialyzer port 902. Header connector 524 is attached by tubing to the fluid inlet connector 390 of both of the precleaner headers 210. Arterial dialyzer connector 525 is connected by tubing to arterial dialyzer port 903. Lower header connector 526 is connected by tubing to the waste discharge connector 392 of the lower precleaner header 210. As shown in FIG. 20, drain connector 527 projects through the back panel 463 of the box 401 (the back 908 of the base unit 999) and provides the waste outlet port 910 and is connected to a drain. Water inlet 528 projects through the back panel 463 of the box 401 and provides the water inlet port 909 and is connected to a water supply.

In Operation

The precleaner headers 10, 210 are preferably used in conjunction with a dialyzer reprocessing device or base unit 999, but may also be used separately. Preferably, both the arterial dialyzer header cap 12a and the venous dialyzer header cap 12b may be connected to two separate precleaner headers 10, 210 or alternatively, each dialyzer header 106 of the dialyzer 98 may be processed separately.

In operation, the precleaner header 10, 210 is preferably connected to i) a source for an incoming stream 100 by the fluid inlet connector 60, 390, ii) a waste drain for the waste stream 104 by the waste discharge connector 54, 392, and iii) a dialyzer 98 by the coupling arm 20, 220. The incoming stream 100 flows through the fluid inlet connector 60, 390, through the needle assembly 22, 222, through the needle 38, 238, out the fluid discharge perforation 28, 228, into the dialyzer header cap 12 and dialyzer header 106, cleaning the buildup 102 from the dialyzer header cap 12 and the dialyzer header 106 including the lumen openings 116 and the hollow fibers 114, forming a waste stream 104. The waste stream 104 flows from the dialyzer header 106, through the dialyzer header cap 12, into the needle assembly receiving channel 24, 224, through the waste discharge channel 26, 226, through the waste discharge outlet connector 54, 392, to a waste drain.

Referring to FIGS. 1A, 6, 17, and 39, the present invention includes a method of precleaning a dialyzer header cap 12 and dialyzer header 106 of a previously used dialyzer 98 comprising: providing a precleaner header 10, 210 selectively coupled to at least one dialyzer header cap 12 of the previously used dialyzer 98, introducing an incoming stream 100 into the precleaner header 10, 210 at a pressure above ambient pressure, causing the incoming stream 100 to discharge into the dialyzer header cap 12 and dialyzer header 106 of the previously used dialyzer 98 and circulate therewith in, and draining the waste stream 104 from the dialyzer header cap 12 through the precleaner header 10, 210.

The incoming stream 100 is preferably a pulsating stream. The pulses may be created by varying the pressure of the incoming stream or by introducing a gas into a liquid. The pulsating stream is preferably a combination of liquid and gas. Various cleaners, sterilants or saline may be used in the incoming stream 100. However, water, Renaclear™ disinfectant, and air or just water and air are the preferred combinations.

The incoming stream 100 may be a carrier solution comprised of a solvent, a comiscible non-solvent, or a combination of both. The incoming stream 100 may act as a dispersing carrier, as a solvating carrier, or a combination of both. The incoming stream 100 may contain solvated chemicals. During flushing, the incoming stream 100 may be saline. The use of saline instead of water may reduce hemolysis, which may help reduce further buildup 102. Chemicals, detergents, and sterilants may also be used in the incoming stream 100.

Initial flushing may either be a reverse flushing pattern or an arterial header cap 12a to venous header cap 12b flow pattern. This initial flushing removes the majority of the remaining blood from the dialyzer 98 and may use saline. The majority of clotting and debris 102 forms at the venous end of the dialyzer 98 due to water depletion of the blood as it passes through the dialyzer 98. Therefore, an arterial header cap 12a to venous header cap 12b flow pattern reduces the amount of debris forced into or through the hollow fibers 114.

The method and device facilitate removal of buildup 102 from the dialyzer 98. The incoming stream 100 enters the dialyzer header cap 12 and removes the buildup 102 including blood clots, proteins, lipids, fibrous biomass, and other buildup including secondary membrane and forms a waste stream 104. Depending upon the chemicals used in the incoming stream 100 and type of dialyzer 98, the frequency of the pulse and the percentage of each substituent can be optimized to provide the most efficient cleaning.

The incoming stream 100 is most preferably operated at a frequency of about 7.8 Hz and a duty cycle of about 33%. The duty cycle is based on time, with air being injected during 33% of the cycle time. The incoming stream 100 is preferably operated at a frequency of 2 to 20 Hz. Frequencies below 2 Hz reduce the rate of cleaning to a point similar to a solid steam. Frequencies above 20 Hz become less effective due to lower spray pulse volume. The incoming stream 100 is preferably operated at a duty cycle of 15% to 60%. Duty cycles less than 15% result in a rate of cleaning similar to a solid stream and duty cycles greater than 60% result in loss of delivery of adequate solution and excessive drying. The preferred frequency and duty cycle is at least partially dependent on the particular needle geometry, water pressure, air pressure, and header cap configuration.

The method may also include rotating or retracting the incoming stream 100 within the dialyzer header cap 12 and dialyzer header 106. The pressure of the incoming stream 100 may be up to 20 psi with an effective pressure on the hollow fibers 114 of approximately 3 psi.

The method of the present invention may also include a process for precleaning a dialyzer 98 as follows:

a) Reverse flush the dialyzer 98 with solution. The solution may be the same as previously described for the incoming stream 100. Preferably the solution is at 10–12 psi for 60 seconds. Although higher pressures would be more effective, dialyzer manufacturers typically recommend that the pressure differential at the hollow fibers 114 not exceed about 12 psi. Although longer flushing may be beneficial, most of the cleaning occurs in the first 60 seconds and minimal additional cleaning occurs after 60 seconds. Reverse flushing is typically accomplished by flowing solution into one or both dialysis ports 110a and 110b of dialyzer 98, around the outsides of the hollow fibers 114 through the sides of the hollow fibers 114, into the lumen of the hollow fibers 114, into both dialyzer headers 106, and out the dialyzer header caps 12. Reverse flushing removes buildup 102 from the dialyzer 98, particularly the dialyzer header 106 without forcing buildup 102 into the lumen openings 116 or the hollow fibers 114.

b) Reverse flush the dialyzer 98 with solution (the same as in step a)) and introduce an incoming stream 100 into the dialyzer header 106. Preferably the incoming stream 100 is at 20 psi for 90 seconds. Preferably the incoming stream 100 is introduced into both dialyzer headers 106 at the same time. The effective pressure on the hollow fibers 114 caused by the incoming stream 100 is approximately 3 psi. Providing a counter pressure within the hollow fibers 114 allows the incoming stream 100 to remove buildup 102 from the dialyzer header 106 without forcing buildup 102 into the lumen openings 116 or the hollow fibers 114. This step removes the blockages from the lumen openings 116 of the hollow fibers 114. Although higher pressures would be more effective, dialyzer manufacturers typically recommend that the pressure differential at the hollow fibers 114 not exceed about 12 psi. Although longer flushing may be beneficial, most of the cleaning occurs in the first 90 seconds and minimal additional cleaning occurs after 90 seconds.

c) Flush dialyzer 98 with solution using a cross flow arrangement. Preferably, the solution pressure of both flows is 10–12 psi and the dialyzer 98 is flushed for 60 seconds. The cross flow arrangement typically consists of two simultaneous flows. Flowing solution into the arterial dialyzer head cap 12a through the hollow fibers 114 and out the venous dialyzer head cap 12b and flowing solution into the venous dialysate port 110b and out the arterial dialyzer port 110a. These flow directions are the same as the flows encountered during dialysis. This flow arrangement provides a balanced pressure at the hollow fibers 114, which helps remove buildup 102 from the hollow fibers 114. This step precleans the hollow fibers 114. Although higher pressures would be more effective, dialyzer manufacturers typically recommend that the pressure differential at the hollow fibers 114 not exceed about 12 psi. Although longer flushing may be beneficial, most of the cleaning occurs in the first 60 seconds and minimal additional cleaning occurs after 60 seconds.

d) Straight flush dialyzer 98 with solution. Preferably, flush at a pressure of 10–12 psi for 60 seconds. Straight flushing consists of flowing solution into the arterial dialyzer header cap 12a through the lumens of the hollow fibers 114 and out the venous dialyzer header cap 12b. This step helps restore any collapsed fibers after flushing the dialyzer using a cross flow arrangement. Although higher pressures would be more effective, dialyzer manufacturers typically recommend that the pressure differential at the hollow fibers 114 not exceed about 12 psi. Although longer flushing may be beneficial, most of the cleaning occurs in the first 60 seconds and minimal additional cleaning occurs after 60 seconds.

The above dialyzer precleaning method is preferably completed in the order of step a) to d). However, other combinations are also effective. For example step a) could be skipped and step b) could be operated longer to make up for step a). The preferred order emphasizes removing blockages from the lumen openings 116 of the hollow fibers with step a) and b) without forcing buildup 102 into the lumen openings 116 of the hollow fibers 114 which could occur. For example, if step d) were to occur prior to step a) or b), buildup 102 in the arterial dialyzer header cap 12a would be forced into the hollow fibers 114. Step c), which precleans the hollow fibers 114, is preferably conducted after the blockages are removed from the lumen openings 116 of the hollow fibers 114 through step a) and b). However, step c) could be completed prior to step a) and b) or after step d). Any debris or buildup 102 that is inadvertently forced into the hollow fibers 114 as a result of step c) can be removed later, particularly by step b).

Chemicals, detergents, or sterilants may also be used in the incoming stream 100 or solutions of step a) through d). However, some may have a tendency to bind the buildup 102 to the dialyzer 98 instead of helping to remove them or be difficult to completely flush from the dialyzer 98.

The method of the present invention may also include a process for precleaning a dialyzer 98 as follows:

The dialyzer cleaning system utilizes four main operational cycles, dialyzer cleaning, system cleaning, system sanitizing and system rinsing. Dialyzer cleaning is the main cycle, and is the only cycle conducted with a dialyzer attached. System cleaning is used to clean the system, preferably on a weekly basis. System sanitizing is a cycle that exposes the system to disinfectant, this operation is preferably conducted daily. System rinse is used to rinse the system after either system cleaning or system sanitizing.

Dialyzer Precleaning

In each of the steps below, the solution may be the same as previously described for the incoming stream 100. Preferably the solution is at 10–12 psi if provided to the dialysis ports 110a, 110b, or the waste discharge outlet 18, 218; or 15–20 psi if provided through the needle 38, 238 which provides an effective pressure on the hollow fibers 114 of approximately 3 psi. Although higher pressures would be more effective, dialyzer manufacturers typically recommend that the pressure differential at the hollow fibers 114 not exceed about 12 psi. Although longer flushing may be beneficial, most of the cleaning occurs in the first 30 to 60 seconds and minimal additional cleaning occurs after 60 to 90 seconds.

a) Dialysate and needle fill. This step primes the system by filling the dialyzer 98 and the precleaner header 10, 210 with solution. Priming the system is preferably accomplished by flowing solution into both dialyzer ports 110a, 110b and both header caps 12a, 12b through the needle 38, 238 and out the header caps 12a, 12b through the waste discharge channel 26, 226 and the waste discharge outlet 18, 218. This step is preferably about 5–10 seconds, most preferably about 6 seconds.

b) Reverse Ultra Filtration. Reverse flush the dialyzer 98 with solution. Preferably the flow is for about 30–90 seconds, and most preferably about 60 seconds. Reverse Ultra Filtration is typically accomplished by flowing solution into one or both dialysis ports 110a and 110b of dialyzer 98, around the outsides of the hollow fibers 114 through the sides of the hollow fibers 114, into the lumen of the hollow fibers 114, into both dialyzer headers 106, and out the dialyzer header caps 12. Reverse flushing removes buildup 102 from the dialyzer 98, particularly the dialyzer header 106 without forcing buildup 102 into the lumen openings 116 or the hollow fibers 114. Preferably, reverse ultra filtration is accomplished by flowing solution into arterial dialysis port 110a and out the waste discharge outlets 18, 218 of both precleaner headers 10, 210.

c) Reverse Ultra Filtration and Header. Reverse flush the dialyzer 98 with solution (the same as in step b)) and at the same time introduce an incoming stream 100 into the dialyzer header 106. Preferably the flow is for 30 to 120 seconds, and most preferably 90 seconds. Providing a counter pressure within the hollow fibers 114 allows the incoming stream 100 to remove buildup 102 from the dialyzer header 106 without forcing buildup 102 into the lumen openings 116 or the hollow fibers 114. This step removes the blockages from the lumen openings 116 of the hollow fibers 114. Preferably, reverse ultra filtration and header flow is accomplished by simultaneously flowing solution into the arterial dialysis port 110a and through the needles 38, 238 of the precleaner headers 10, 210. Preferably, solution flows out both precleaner headers 10, 210 through the waste fluid outlet 18, 218.

d) Through Fiber. Straight flush dialyzer 98 with solution. Preferably, the flow is for 30 to 90 seconds, most preferably 30 seconds. Straight flushing consists of flowing solution into the arterial dialyzer header cap 12a through the lumens of the hollow fibers 114 and out the venous dialyzer header cap 12b. Preferably through fiber flushing is accomplished by flowing solution into the arterial precleaner header 10, 210 via the waste discharge outlet 18, 218 through the lumens of the hollow fibers 114 into the venous dialyzer header cap 12b, and through the waste discharge outlet 18, 218 of the venous precleaner header 10, 210.

e) Full Flush. Flush dialyzer 98 with solution using a unidirectional flow arrangement. Preferably, the solution is flushed for 30 to 90 seconds, most preferably about 30 seconds. The full flush arrangement typically consists of two simultaneous flows. Flowing solution into the arterial dialyzer head cap 12a through the hollow fibers 114 and out the venous dialyzer head cap 12b and flowing solution into the arterial dialysate port 110a and out the venous dialyzer port 110b. This flow arrangement provides a balanced pressure at the hollow fibers 114, which helps remove buildup 102 from the hollow fibers 114. This step precleans the hollow fibers 114. Preferably, full flushing is accomplished by simultaneously flowing solution into the arterial dialysis port 110a and into the arterial precleaner header 10, 210 via the waste discharge outlet 18, 218. Solution is discharged out the venous dialysis port 110b and out the venous precleaner header 10, 210 via the waste discharge outlet 18, 218.

f) Disinfectant Exposure. Flush dialyzer 98 with disinfectant or sanitizing solution. Preferably, the solution is flushed 30 to 90 seconds, most preferably 30 seconds. The disinfectant exposure typically consists of flowing disinfectant solution through both precleaner headers 10, 210 and both dialyzer headers caps 12a, 12b. Preferably, disinfectant exposure is accomplished by flowing disinfectant solution into the arterial dialysis port 110a and through the needles 38, 238 of the precleaner headers 10, 210. Preferably, disinfectant solution flows out both precleaner headers 10, 210 through the waste fluid outlet 18, 218. Preferably, the disinfectant solution is Renaclear™ disinfectant.

System Clean

The system clean cycle is preferably conducted about once per week to clean the dialyzer cleaning system. The system clean cycle preferably uses "For Industrial Use Only" Formula 409® cleaner. The system clean cycle consists of cleaning around the needles 238, cleaning the needles 238, and cleaning of all lines. Preferably, the cleaner should remain in the system for 8 hours.

System Sanitize

The system sanitize is preferably conducted at the end of each day to sanitize the system. The system sanitize cycle exposes the system to disinfectant, preferably Renaclear™ disinfectant. The system sanitize cycle consists of exposing disinfectant to the shunts, exposing disinfectant to the needles, and exposing disinfectant to all lines. Preferably, the disinfectant should remain in the system for 6 hours.

System Rinse

The system rinse cycle is preferably conducted after each sanitize cycle and each clean cycle after the necessary dwell times. The system rinse cycle consists of rinsing the shunts, rinsing the needles, and rinsing all lines.

System Operation

The present invention cleans blood and debris from hollow fiber dialyzers before reprocessing. The system has two header cleaners 10, 210 that attach to the header caps 12 of the dialyzer 98. The header cleaners 10, 210 clean the dialyzer headers 106 and blood path with a special cleaning injector or needle 38, 238. At the same time, the invention pumps fluid through the dialysis ports 110a, 110b to clean the rest of the dialyzer 98. Dialyzers 98 cleaned with the invention still require reprocessing before use.

The invention is controlled via the front panel 901. On the right side of the panel 901 are a series of buttons for operation of the device. The following is a summary of descriptions of the buttons.

On button 950—Turns the system on. The LED on the button will light when the system is on.

Off button 951—Turns the system off.

Start Dialyzer Clean button 952—Starts the dialyzer clean cycle.

Stop Dialyzer Clean button 953—Stops, or interrupts, the dialyzer clean cycle.

Add Chemical indicator 954—Flashes when the system cannot detect disinfectant (during a dialyzer clean or system sanitize cycle) or cleaner (during a system clean cycle).

System Clean button 955—Starts the system clean cycle.

System Sanitize button 956—Starts the system sanitize cycle.

System Rinse button 957—Starts the system rinse cycle.

System Stop button 958—Stops, or interrupts, the system clean, rinse, or sanitize cycle.

Disconnect Chemical indicator 959—Flashes when cleaner is still connected to the system and the system is not running a clean cycle.

The On button 950 has an LED light, or indicator, in the upper right hand corner. This indicator remains lit while the machine is on. Each 'cycle button' 952, 955, 956, 957 also has an LED indicator in the upper right hand corner. The indicator on a cycle button will light when that cycle is running. The indicator will typically flash when the system needs operator input to complete the cycle.

The system will preferably sound or otherwise provide an alarm when a cycle has ended or operator action is required. There are two types of audible alarms: cycle complete alarms and action alarms. The cycle complete alarm is a continuous, 2 second tone that sounds when the running cycle ends. The action alarm is a double beep that sounds three times to alert that further steps are required to finish the cycle.

Cleaning a Dialyzer

Connecting the Dialyzer

The following steps describe how to attach a dialyzer 98 to the system for cleaning. The dialyzer 98 is connected to the system with the venous (blue) end (12b, 110b, 902) up.

Preferably, the lower, arterial connections (12a, 903, 110a) are hooked up first and the upper, venous connections (12b, 110b, 902) are hooked are up last. A series of dotted lines are pictured on the front panel 901 of the system to indicate proper connection of the system cleaning lines. The invention is shown in FIG. 18 in the proper connection of the front panel cleaning lines.

The dialyzer is preferably connected to the system as follows: a) Position the dialyzer 98 with the venous header cap 12b up; b) Remove the arterial blood port cap (not shown); c) Connect the arterial, or lower, header cleaner 210a to the arterial end (12a) of the dialyzer 98 and tighten the header cleaner 210 by turning the thumb wheel or coupling arm 220; d) Remove the arterial dialysate port cap (not shown); e) Connect the lower dialysate connector 903 to the lower (arterial) dialysate port 110a; f) Remove the venous dialysate port cap (not shown); g) Insert the upper (venous) dialysate port 110b of the dialyzer 98 into the upper dialysate connector 902; h) Remove the venous blood port cap (not shown); i) Connect the venous, or upper, header cleaner 210b to the (venous) blue end (12b) of the dialyzer 98 and tighten the header cleaner 210b by turning the thumb wheel or coupling arm 220; j) The dialyzer port caps may be processed using typical reprocessing protocol. Preferably, the port caps may be disinfected by immersion in fresh 1% Renalin® Solution or full-strength Actril® solution for a minimum of 30 minutes.

Running the Dialyzer Clean Cycle

Before running the dialyzer clean cycle, check the system to confirm that all dialyzer connections are secure and that the LED on the On button 950 is lit, indicating the system is ready for use.

To clean the dialyzer press the Start Dialyzer Clean button 952. The LED on the button will go on and remain lit during this cycle. The cycle will start and will take about 4 minutes to run. When the cycle is finished, a two-second cycle compete alarm will sound and the LED on the Start Dialyzer Clean button 952 will turn off. Remove the dialyzer 98 from the system by following the steps outlined below. The dialyzer 98 will then be ready for reprocessing.

The dialyzer clean cycle may be stopped by pressing the Stop Dialyzer Clean button 953. The dialyzer may be removed from the machine, or press the Start Dialyzer Clean button 952 to restart the cycle. If desired, the dialyzer clean cycle may be repeated.

To disconnect the dialyzer 98 after cleaning: a) Disconnect the venous, or upper, header cleaner 210b from the venous end (12b) of the dialyzer 98; b) Loosen the header cleaner 210 by turning the thumb wheel or coupling arm 220; c) Place a disinfected port cap (not shown) over the venous blood port; d) Remove the upper (venous) dialysate port 110b of the dialyzer 98 from the upper dialysate connector 902; e) Place a disinfected port cap (not shown) over the dialysate port 110b; f) Disconnect the lower dialysate connector 903 from the lower (arterial) dialysate port 110a; g) Place a disinfected port cap (not shown) over the dialysate port 110a; h) Disconnect the arterial, or lower, header cleaner 210b from the arterial end (12a) of the dialyzer 98. i) Loosen the header cleaner 210a by turning the thumb wheel or coupling arm 220; j) Place a disinfected cap (not shown) over the arterial blood port; k) After the dialyzer 98 is removed, the header cleaner connections on the system may be surface disinfected with 1% Renalin® solution or full-strength Actril® Cold Sterilant.

Cleaning and Sanitizing the System

Preferably, the system is regularly cleaned and sanitized to stay in proper working order. Follow the steps below to clean and sanitize the system.

Figure 22:
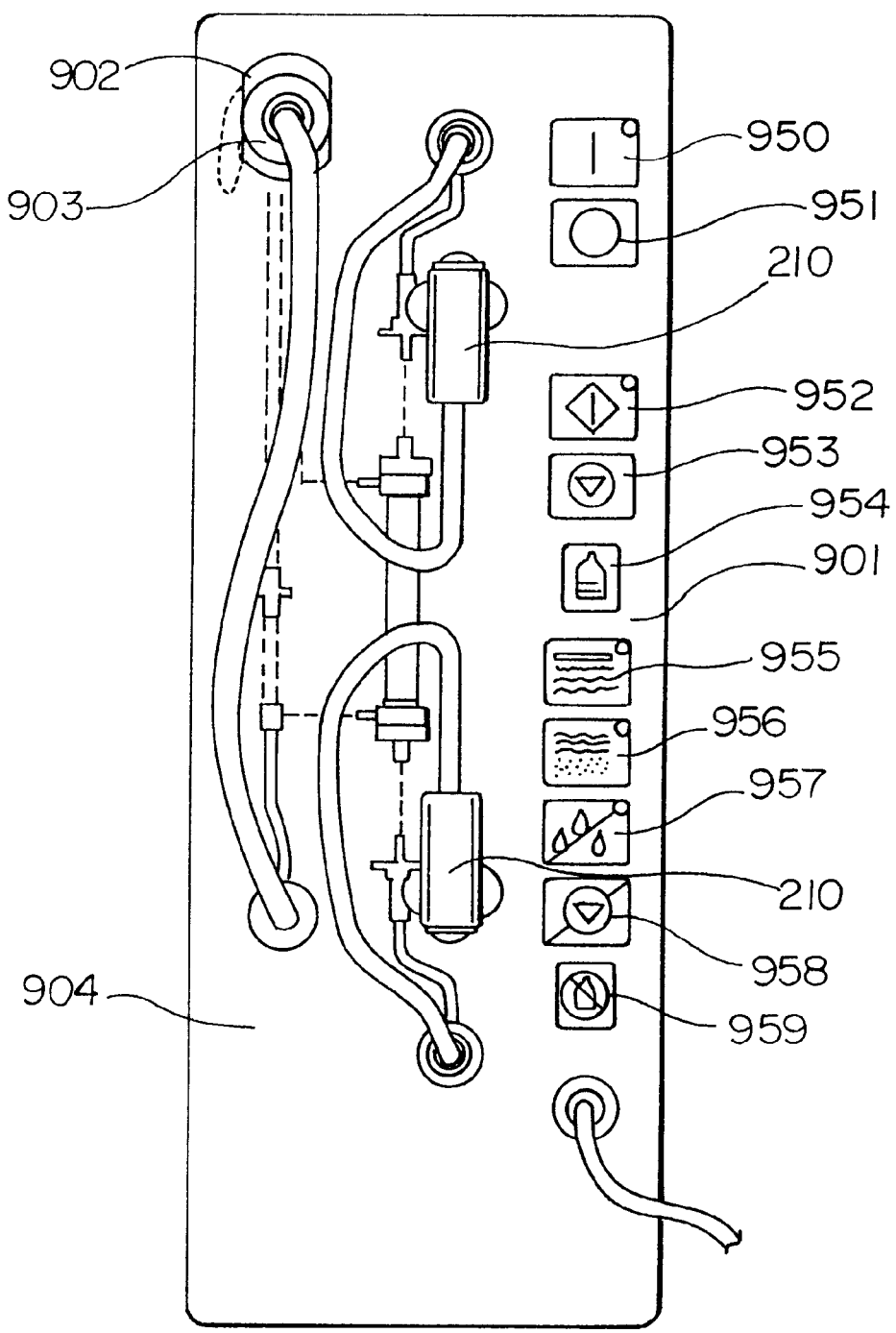
FIG. 22 is a front view of the present invention in the storage or cleaning position showing the control panel.

Before cleaning and/or sanitizing the system, configure the system's front panel connections as shown in FIGS. 21 and 22. A series of dotted lines are pictured on the front panel 901 of the system to indicate the proper connections. FIGS. 21 and 22 show the correct way to configure the system for cleaning, sanitizing and rinsing.

The step-by step procedure is as follows: a) Attach the upper header cleaner 210b to the upper precleaner header needle port 906b; b) Attach the lower header cleaner 210a to the lower precleaner header needle port 906a; c) Attach the dialysate shunt 415 to the lower dialysate tubing connector 903, the dialysate shunt 415 is attached to a chain on the front panel 901 of the system; d) Insert the other end of the shunt 415 into the upper dialysate port connector 902.

Sanitizing the System

The system is preferably sanitized once a day. After the system sanitize cycle runs, the system preferably should sit for at least 6 hours. Preferably, the sanitation cycle is performed at the end of the day. Before sanitizing the system, confirm that all connections are secure, that the disinfectant bottle contains chemical 932 and is connected to the system, and that the LED on the On button 950 is lit, indicating the system is ready for use.

To run the system sanitize cycle: a) Press the System Sanitize button 956 to start the sanitize cycle, the LED on the System Sanitize button 956 will light continuously and the sanitize cycle takes about 2 minutes b) When the sanitize cycle is finished, the LED on the System Sanitize button 956 will turn off, the system will sound a cycle complete alarm and the LED on the System Rinse button 957 will start to flash; c) Turn off the unit by pressing the Off button 951 on the front panel 901, and allow the unit to sit for at least six hours (The system may be sanitized at the end of the day and allowed it to sit overnight); d) After the 6 hour dwell time is up, press the On button 950 on the front panel 901, the LED on the System Rinse button 957 will begin to flash (A rinse cycle must be completed before the machine is ready to clean dialyzers); e) Press the System Rinse button 957, the LED on the System Rinse button 957 will stop flashing and light continuously during the 3 minute rinse cycle; f) When the rinse cycle is finished, the LED will turn off and a cycle complete alarm will sound indicating that the system is now ready for use.

The system sanitize cycle may be stopped by pressing the System Stop button 958. The cycle may be restarted by pressing the System Sanitize button 956.

Cleaning the System

The system is preferably cleaned at least once a week. After the system clean cycle runs, the system must sit for at least 8 hours. Preferably, the system clean cycle is performed at the end of the work week. Cleaner 934 may be left in the system for several days, if necessary. Before cleaning the system, confirm that all connections are secure, that the cleaner bottle contains cleaning fluid 934, and that the LED on the On button 950 is lit, indicating the system is ready for use.

To run the system clean cycle: a) Find the quick connect fitting 907 on the end of the cleaner uptake tubing 907 and plug the fitting into the cleaner port 905 on the front of the machine 901 (See FIG. 21); b) Press the System Clean button 955 to start the clean cycle, the LED on the System Clean button 955 will light continuously while the cycle runs for about 1.5 minutes; c) When the system clean cycle is finished, the LED on the System Clean button 955 will turn off, the system will sound a cycle complete alarm, and the LED on the System Rinse button 957 will start to flash; d) Turn off the unit by pressing the Off button 951 on the front panel, then allow the unit to sit for at least 8 hours; e) After the 8 hour dwell time is up, press the On button 950 on the front panel 901 of the unit and the LED on the System Rinse button 957 will begin to flash; f) Disconnect the quick connect coupling 907 from the cleaner port 905; g) Press the System Rinse button 957 and the LED on the System Rinse button 957 will stop flashing and light continuously during the 3 minute rinse cycle; h) When the rinse cycle is finished, the LED will turn off and a cycle complete alarm will sound; i) Press the System Sanitize button 956 to run a sanitize cycle, the LED on the System Sanitize button 956 will light continuously for about 2 minutes while the cycle runs; j) When the sanitize cycle is finished, the system will sound a cycle complete alarm and the LED on the System Sanitize button 956 will turn off and the LED on the System Rinse button 957 will start to flash; k) Allow the unit to sit for 10 minutes before rinsing to provide low-level disinfection of the system; l) Press the System Rinse button 957 to activate the 3 minute rinse cycle; m) When the cycle is finished, the LED will turn off and a cycle complete alarm will sound. The system is now ready for use.

The system clean cycle may be stopped by pressing the System Stop button 958. Pressing the System Clean button 955 will restart the cycle.

Changing the System Fluids
The Add Chemical indicator 954

The Add Chemical indicator 954 flashes when the system does not sense cleaning fluid 934 or chemical 932. This usually means that the bottle(s) are empty, or are not connected to the machine correctly. The Add Chemical indicator 954 may flash during the dialyzer clean, system clean or the system sanitize cycles.

During the dialyzer clean cycle, the system cleans blood and debris from the dialyzer 98 before reprocessing. The system has two header cleaners 210*a*, 210*b* that attach to the blood ports of the dialyzer 98. The header cleaners 210 clean the dialyzer headers 106 and blood path with a special cleaning injector or needle 38, 238. At the same time, the system pumps fluid through the dialyzer's dialysate ports 110*a*, 110*b* to clean the rest of the dialyzer 98. Dialyzers cleaned with the system must be reprocessed before use.

If the Add chemical indicator flashes during the system clean cycle, the system does not sense any cleaning fluid 934. This means that the bottle is either empty or is not plugged into the purple cleaner port 905 on the front panel 901 of the machine. Replace the cleaning fluid bottle if necessary, and connect it to the purple cleaner port 905.

If the Add chemical indicator 954 flashes during the System sanitize cycle, the system does not sense any chemical 932. Check the chemical bottle and replace, if necessary.

The Disconnect Chemical Indicator 959

The Disconnect Chemical 959 indicator flashes if the cleaner uptake tubing remains connected to the cleaner port 905 after the system clean cycle if attached during a rinse cycle.

Replacing the Chemical Bottle

FIG. 20 indicates how to connect the chemical bottle. Replace the chemical bottle by a) removing the cap from new jug, b) placing a new jug next to the empty jug, c) unscrewing the cap with draw tube 931 from the empty jug and carefully transferring the draw tube 931 to the new jug without dripping.

Replacing the Cleaning Fluid Bottle

FIG. 21 indicates how to connect the cleaning fluid bottle. Replace the cleaning fluid bottle by a) removing the packing cap from the new jug of cleaning fluid, b) placing the new jug of cleaning fluid next to the empty jug, c) unscrewing the cap from the empty jug of cleaning fluid d) removing the cap with the attached chemical draw tube 933 and uptake tubing and transferring the draw tube 933 and uptake tube to the new jug, e) locating the quick connect fitting 907 on the end of the cleaning fluid tubing, f) plugging the fitting 907 into the purple cleaner port 905 on the front 901 of the machine.

Although the description of the preferred embodiment has been presented, it is contemplated that various changes, including those mentioned above, could be made without deviating from the spirit of the present invention. It is therefore desired that the present embodiment be considered in all respects as illustrative, not restrictive, and that reference be made to the appended claims rather than to the foregoing description to indicate the scope of the invention.

We claim:

1. A method of precleaning a header cap of a previously used dialyzer comprising:
    (a) providing a precleaner header selectively coupled to at least one dialyzer header cap of the previously used dialyzer, said precleaner header including a needle having an inlet in fluid communication with a source of cleaning fluid and an outlet in fluid communication with the header cap;
    (b) introducing an incoming stream of cleaning fluid into said needle at a pressure above ambient pressure;
    (c) introducing an incoming stream of air at a pressure above ambient pressure into said incoming stream of cleaning fluid;
    (d) causing said incoming stream of cleaning fluid containing air to discharge into the dialyzer header of the previously used dialyzer thereby causing said incoming stream of cleaning fluid containing air to circulate therewith in;
    (e) forming a waste stream within said dialyzer header; and
    (f) draining said waste stream from said dialyzer header through said precleaner header.

2. The method of claim 1 wherein said incoming stream is comprised of a pulsating stream.

3. The method of claim 2 wherein said pulsating stream comprises a solution and air.

4. The method of claim 1 wherein said incoming stream is rotatably circulated therewith in.

5. The method of claim 1 further comprising reverse flushing the dialyzer.

6. The method of claim 5 wherein said reverse flushing the dialyzer occurs before said causing said incoming stream to discharge into the dialyzer header.

7. The method of claim 1 further comprising flushing the dialyzer using a cross flow arrangement.

8. The method of claim 7 wherein said flushing the dialyzer using a cross flow arrangement occurs after said causing said incoming stream to discharge into the dialyzer header.

9. The method of claim 1 further comprising flushing the dialyzer from an arterial dialyzer header cap to a venous dialyzer header cap.

10. The method of claim 9 wherein said flushing the dialyzer from the arterial dialyzer header cap to the venous dialyzer header cap occurs after said causing said incoming stream to discharge into the dialyzer header.

11. The method of claim 1 further comprising:
    (a) reverse flushing the dialyzer;
    (b) reverse flushing the dialyzer while said causing said incoming stream to discharge into the dialyzer header;
    (c) flushing the dialyzer using a cross flow arrangement; and (d) flushing the dialyzer from an arterial dialyzer header cap to a venous dialyzer header cap.

12. The method of claim 11 wherein (a) first said reverse flushing the dialyzer; then (b) said reverse flushing the dialyzer while said causing said incoming stream to discharge into the dialyzer header; then (c) said flushing the dialyzer using a cross flow arrangement; and then (d) said flushing the dialyzer from an arterial dialyzer header cap to a venous dialyzer header cap.

13. The method of claim 1 further comprising priming the dialyzer.

14. The method of claim 1 further comprising reverse ultrafiltration of the dialyzer.

15. The method of claim 1 further comprising reverse ultrafiltration of the dialyzer and simultaneously flushing the dialyzer through the precleaner header.

16. The method of claim 1 further comprising through fiber flushing of the dialyzer.

17. The method of claim 1 further comprising full flushing the dialyzer.

18. The method of claim 1 further comprising disinfectant exposure of the dialyzer.

19. The method of claim 1 further comprising:

(a) priming the dialyzer;

(b) reverse ultrafiltration of the dialyzer;

(c) reverse ultrafiltration of the dialyzer and simultaneously flushing the dialyzer through the precleaner header;

(d) through fiber flushing of the dialyzer;

(e) full flushing the dialyzer; and (f) disinfectant exposure of the dialyzer.

* * * * *

UNITED STATES PATENT AND TRADEMARK OFFICE
CERTIFICATE OF CORRECTION

PATENT NO. : 6,192,900 B1
DATED : February 27, 2001
INVENTOR(S) : Arnal et al.

Page 1 of 1

It is certified that error appears in the above-identified patent and that said Letters Patent is hereby corrected as shown below:

Column 4,
Line 20, delete "therewith" and substitute -- therewithin -- therefor.

Column 5,
Line 34, delete "through" and substitute -- thorough -- therefor.

Column 7,
Line 51, delete "of the" therefor.

Column 9,
Line 35, delete "wastestream" and substitute -- waste stream -- therefor.

Column 10,
Line 33, delete "is" therefor.

Column 19,
Line 35, delete "receipt" and substitute -- receptacle -- therefor.

Column 25,
Line 20, delete "through" and substitute -- thorough -- therefor.

Column 30,
Lines 33 and 43, delete "therewith in" and substitute -- therewithin -- therefor.

Column 32,
Line 13, delete "through" and substitute -- thorough -- therefor.

Signed and Sealed this

Eleventh Day of December, 2001

Attest:

NICHOLAS P. GODICI
*Attesting Officer*  *Acting Director of the United States Patent and Trademark Office*